(12) United States Patent
Van Calenbergh et al.

(10) Patent No.: US 7,638,505 B2
(45) Date of Patent: Dec. 29, 2009

(54) ORGANOPHOSPHORIC DERIVATIVES USEFUL AS ANTI-PARASITIC AGENTS

(75) Inventors: Serge Van Calenbergh, De Pinte (BE); Timothy Haemers, Mariakerke (BE); Vincent Devreux, Waregem (BE); Hassan Jomaa, Giessen (DE); Jochen Wiesner, Giessen (DE)

(73) Assignee: Universiteit Gent (BE)

( * ) Notice: Subject to any disclaimer, the term of this patent is extended or adjusted under 35 U.S.C. 154(b) by 0 days.

(21) Appl. No.: 12/158,973

(22) PCT Filed: Dec. 22, 2006

(86) PCT No.: PCT/EP2006/012521

§ 371 (c)(1),
(2), (4) Date: Jun. 23, 2008

(87) PCT Pub. No.: WO2007/071453

PCT Pub. Date: Jun. 28, 2007

(65) Prior Publication Data

US 2008/0312190 A1   Dec. 18, 2008

(30) Foreign Application Priority Data

Dec. 23, 2005  (GB) ................. 0526655.6

(51) Int. Cl.
*A01N 57/00* (2006.01)
(52) U.S. Cl. .................................................. 514/114
(58) Field of Classification Search ............. 514/114
See application file for complete search history.

(56) References Cited

FOREIGN PATENT DOCUMENTS

WO   WO 2005/048715   6/2008

OTHER PUBLICATIONS

Haemers et al., "Synthesis of α-Aryl-Substituted and Conformationally Restricted Fosmidomycin Analogues as Promising Antimalarials," *European Journal of Organic Chemistry*, 3856-3863, 2006.

Haemers et al., "Synthesis of α-Substituted Fosmidomycin Analogues as Highly Potent *Plasmodium falciparum* Growth Inhibitors," *Bioorganic & Medicinal Chemistry Letters*, 16: 1888-1891, 2006.

Kurz et al., "Synthesis and Antimalarial Activity of Chain Substituted Pivaloyloxymethyl Ester Analogues of Fosmidomycin and FR900098," *Bioorganic & Medicinal Chemistry Letters*, 14: 5121-5135, 2006.

Silber et al., "AFMoC Enhances Predictivity of 3D QSAR: A Case Study with DOXP-reductoisomerase," *Journal of Medicinal Chemistry*, vol. 48: 3547-3563, 2005.

International Search Report (PCT/EP2006/012521) mailed Apr. 23, 2007.

Written Opinion of the International Searching Authority (PCT/EP2006/012521) mailed Apr. 23, 2007.

Response to the Written Opinion mailed Apr. 23, 2007 (PCT/EP2006/012521) dated Oct. 23, 2007.

Written Opinion of the International Preliminary Examining Authority (PCT/EP2006/012521) mailed Jan. 24, 2008.

Response to the Second Written Opinion mailed Jan. 24, 2008 (PCT/EP2006/012521) dated Feb. 25, 2008.

International Preliminary Report on Patentability (PCT/EP2006/012521) mailed Mar. 27, 2008.

Official Communication for European Patent Application No. 06 847 002.0, dated Jul. 22, 2009.

*Primary Examiner*—Raymond J Henley, III
(74) *Attorney, Agent, or Firm*—Clark & Elbing LLP

(57) ABSTRACT

The present invention relates to novel phosphonic acid compounds having the structural formula (I): wherein: (a) R is a group of 1 to 5 substituents independently selected from the group consisting of fluoro, chloro, bromo, $C_{1-4}$ alkoxy, $C_{1-4}$ alkyl, hydroxy, formyl, trifluoromethoxy, phenyl, heterocyclic, heterocyclic-substituted methyl, aminomethyl, hydroxy methyl, bromomethyl, sulfonyl chloride, acetyl chloride, nitroso and cyano, (b) $R_1$ is selected from the group consisting of hydrogen, $C_{1-7}$ alkyl, $C_{3-10}$ cycloalkyl, aryl, arylalkyl and heterocyclic, and (c) $R_2$ is selected from the group consisting of hydroxy and hydroxy-protecting groups, and stereoisomer, solvates and salts thereof. These compounds are useful as anti-infectious and anti-parasitic agents, in particular anti-malaria agents.

19 Claims, No Drawings

ORGANOPHOSPHORIC DERIVATIVES USEFUL AS ANTI-PARASITIC AGENTS

CROSS-REFERENCE TO RELATED APPLICATIONS

This application is the U.S. National Stage of International Application No. PCT/EP2006/012521, filed Dec. 22, 2006 which claims the benefit of GB 0526655.6, filed Dec. 23, 2005.

FIELD OF THE INVENTION

The present invention relates to novel substituted organophosphoric derivatives being useful as anti-infectious, in particular anti-parasitic agents, especially against malaria, as well as to methods for producing said derivatives. The invention also relates to pharmaceutical compositions including a therapeutically effective amount of said novel substituted organophosphoric derivatives, and to methods of treatment of infectious diseases.

BACKGROUND OF THE INVENTION

Malaria is estimated to kill more than one million people annually, especially among children under six years of age. As a result of the resurgence of malaria and increased resistance to prevalent anti-malaria agents such as chloroquine, there is an urgent need for new efficient chemotherapeutics against this disease. Drug development has shifted toward targeting specific proteins that are unique and critical for cellular growth and survival of the parasite. Recently, the presence of a mevalonate-independent pathway for isoprenoid biosynthesis in Plasmodium falciparum was discovered. 1-deoxy-D-xylulose-5-phosphate (hereinafter abbreviated as DOXP) reducto-isomerase plays an essential role in this non-mevalonate pathway, which is absent in humans. Previous studies demonstrated that fosmidomycin exerts potent anti-malaria activity by inhibition of DOXP reducto-isomerase (hereinafter abbreviated as DXR), the second enzyme in the reaction cascade. In recent clinical trials conducted in Gabon and Thailand, fosmidomycin proved to be efficient in the treatment of patients suffering from acute, uncomplicated Plasmodium falciparum malaria. Fosmidomycin however has the disadvantages of a short plasma half-life and a moderate resorption rate. The acetyl derivative of fosmidomycin, also known as FR900098, was shown to be approximately twice more active than fosmidomycin against Plasmodium falciparum in vitro as well as in a Plasmodium vinckei mouse model.

British Patent No. 1,467,304 discloses N-(3-aminopropyl)-aminoalkane-phosphonic acid esters having the structural formula:
$(PO_3R_1R_2)$—$(CR_3R_4)$—$(CH_2)_a$—$(CHR_6)_b$—$CHR_5$—NH—$(CH_2)_3$—$NH_2$ wherein $R_1$ and $R_2$ are both alkyl, a=0-2 and b=0-1, which are made by reacting an aminoalkanephosphonic acid ester having the structural formula: $(PO_3R_1R_2)$—$(CR_3R_4)$—$(CH_2)_a$—$(CHR_6)_b$—$CHR_5$—$NH_2$ with acrylonitrile, followed by catalytic hydrogenation.

U.S. Pat. No. 6,638,957 discloses compounds wherein the nitrogen atom of a 5- to 7-membered nitrogen-oxygen heterocycle is linked to an organophosphorus group $POR_9R_{10}$ (wherein each of $R_9$ and $R_{10}$ may be hydrogen) via a linker B being an alkenylene group optionally substituted with hydroxy, halogen or oxo. U.S. Pat. No. 6,638,957 additionally discloses 4 individual compounds where a p-substituted phenyl group is present in a position of the organophosphorus group.

U.S. Pat. No. 6,680,308 discloses organophosphorous compounds having the structural formula $R_1R_2N$-A-$POR_3R_4$ wherein:
each of $R_1$ and $R_2$ may be hydrogen, alkyl, hydroxyalkyl, alkenyl, alkynyl, aryl, acyl, cycloalkyl, aralkyl, heterocyclic, halogen, $OX_1$ or $OX_2$,
each of $X_1$ and $X_2$ may be hydrogen, alkyl, hydroxyalkyl, alkenyl, alkynyl, aryl, acyl, cycloalkyl, aralkyl or heterocyclic,
A is alkylene, alkenylene or hydroxyalkylene, and
each of $R_3$ and $R_4$ may be hydrogen, alkyl, hydroxyalkyl, alkenyl, alkynyl, aryl, acyl, cycloalkyl, aralkyl, heterocyclic or halogen.

A is preferably a chain of 3 carbon atoms, and acyl may originate from a carboxylic, carbonic, carbamic or imidic acid or thioacid. In particular, U.S. Pat. No. 6,680,308 discloses:
3-(N-hydroxyamino)-propylphosphonic acid diethylester,
3-(N-hydroxyamino)-propylphosphonic acid,
3-(N-formylhydroxyamino)-propylphosphonic acid diethylester,
3-(N-acetylhydroxyamino)-propylphosphonic acid diethylester,
3-(N-formylhydroxyamino)-propylphosphonic acid monosodium salt, and
3-(N-acetylhydroxyamino)-propylphosphonic acid monosodium salt.

U.S. Pat. No. 6,534,489 discloses organo-phosphorous compounds having the structural formula $R_1R_2N$-A-$POR_3R_4$ wherein:
each of $R_1$, $R_2$, $R_3$ and $R_4$ is as defined in U.S. Pat. No. 6,680,308, and
A is a $C_{2-5}$ alkylene group substituted with at least one $C_{3-8}$ cycloalkyl-$C_{0-9}$ alkyl group.

The only individual species exemplified in U.S. Pat. No. 6,534,489 are those wherein:
A is a trimethylene group substituted, but not in a position of the organophosphorus group, with phenylethyl, cyclohexylethyl or pyridylethyl
$R_1$ is acetyl, and
$R_2$ is hydroxy.

WO 2005/048715 discloses organophosphorous compounds having the structural formula $R_1R_2N$—$CH_2)_2$—$CHCy$-$POR_3R_4$ wherein:
Cy is a (optionally substituted with alkyl, alkoxy, cycloalkyl-$C_{0-9}$ alkyl, cycloalkyl-$C_{0-9}$ alkyloxy, acyl, hydroxy, halogen or trifluoromethyl) $C_{5-8}$ mono- or bicyclic cycloalkyl group, wherein said cycloalkyl group may be unsaturated with one or more double or triple bonds and wherein 1 to 4 carbon atoms of said cycloalkyl group may be replaced with N, O or S; and
each of $R_1$ and $R_2$ may be hydrogen, amino, alkyl, alkoxy, cycloalkyl, cycloalkyl-$C_{0-9}$ alkyl, cycloalkyl-$C_{0-9}$ alkyloxy, acyl, heterocyclic, hydroxy, halogen, trifluoromethyl, $NHX_1$, $NHX_2$, $OX_1$ or $OX_2$, but and $R_2$ are not both hydrogen,
each of $R_3$ and $R_4$ may be hydrogen, alkyl, alkoxy, cycloalkyl, acyl, cycloalkyl-$C_{0-9}$ alkyl, cycloalkyl-$C_{0-9}$ alkyloxy, heterocyclic, hydroxy, halogen, trifluoromethyl, $OX_3$ or $OX_4$, and
each of $X_1$, $X_2$, $X_3$ and $X_4$ may be hydrogen, halogen, alkyl, cycloalkyl, cycloalkyl-$C_{0-9}$ alkyl, cycloalkyl-$C_{0-9}$ alkyloxy or heterocyclic.

The cycloakyl group Cy may be aromatic and such aromatic cyclic group may further include substituents such as nitro, trifluoromethyl and phenyl residues; particularly preferred are aromatics substituted with one or more alkyl groups such as methyl, ethyl, propyl or isopropyl. Other preferred cycloalkyl groups include furanyl (page 10 line 2), indolyl and benzidinyl.

Individual species described in WO 2005/048715 together with their biological data include the following:
α-phenyl-fosmidomycin diethanolammonium salt,
α-phenyl-FR900098 diethanolammonium salt,
[3-(hydroxy-formyl-amino)-1-(p-fluorophenyl)-propyl] phosphonic acid di-(2,2-dimethylpropionic acid) ester,
[3-(hydroxy-formyl-amino)-1-(o-fluorophenyl)-propyl] phosphonic acid di-(2,2-dimethylpropionic acid) ester,
[3-(hydroxy-formyl-amino)-1-(o,p-dichlorophenyl)-propyl] phosphonic acid di-(2,2-dimethylpropionic acid) ester,
[3-(hydroxy-formyl-amino)-1-(o,o-dichlorophenyl)-propyl] phosphonic acid di-(2,2-dimethylpropionic acid) ester,
[3-(hydroxy-formyl-amino)-1-(o-toluoyl)-propyl] phosphonic acid di-(2,2-dimethylpropionic acid) ester,
[3-(hydroxy-formyl-amino)-1-(p-toluoyl)-propyl] phosphonic acid di-(2,2-dimethylpropionic acid) ester,
[3-(hydroxy-formyl-amino)-1-(o,o-xylyl)-propyl] phosphonic acid di-(2,2-dimethylpropionic acid) ester,
[3-(hydroxy-formyl-amino)-1-(p-biphenyl)-propyl] phosphonic acid di-(2,2-dimethylpropionic acid) ester,
[3-(benzyloxy-formyl-amino)-1-naphthyl-propyl] phosphonic acid di-(2,2-dimethylpropionic acid) ester,
[3-(benzyloxy-formyl-amino)-1-phenyl-propyl] phosphonic acid diethyl ester,
[3-(benzyloxy-acetyl-amino)-1-phenyl-propyl] phosphonic acid diethyl ester,
[3-(benzyloxy-formyl-amino)-1-phenyl-propyl] phosphonic acid di-(2,2-dimethylpropionic acid) ester,
[3-(benzyloxy-acetyl-amino)-1-phenyl-propyl] phosphonic acid di-(2,2-dimethylpropionic acid) ester,
[3-hydroxy-formyl-amino)-1-phenyl-propyl] phosphonic acid di-(2,2-dimethylpropionic acid) ester, and
[3-hydroxy-acetyl-amino)-1-phenyl-propyl] phosphonic acid di-(2,2-dimethylpropionic acid) ester.

The biological data (measured against *Plasmodium falciparum* strain Dd2) for the 17 above compounds, especially in the Desjardins test procedure, show that:
the $IC_{50}$ value of α-phenyl-fosmidomycin diethanolammonium salt is 4.5 times less than fosmidomycin, but the $IC_{50}$ value of α-phenyl-FR900098 diethanol-ammonium salt is higher than FR900098; and
the $IC_{50}$ value of α-phenyl-fosmidomycin di-(2,2-dimethylpropionic acid) esters is not significantly changed when the α-phenyl group is substituted with one or two fluoro, chloro or methyl groups; it is however disadvantageously increased for the o,o-dichlorophenyl and p-biphenyl substituents.

Therefore there is a regular need in the art for novel compounds having significant and specific anti-parasitic properties without having the drawbacks of known effective anti-parasitic agents. There is a regular need in the art for effective anti-parasitic agents having improved metabolisation and/or pharmacokinetic behaviour and which therefore can be more easily formulated into effective dosage forms. There is also a need in the art for such novel compounds exhibiting a longer plasma half-life and a significantly improved resorption rate. There is also a need in the art for such novel compounds which can be easily produced in good yield and purity from commercially available materials through a limited number of fully reproducible synthetic process steps.

SUMMARY OF THE INVENTION

The present invention relates to the unexpected finding that certain α-phenyl organophosphoric derivatives having a specific substitution pattern on said phenyl ring are able to display specific and anti-infectious, in particular, anti-parasitic, activity. An advantage of some embodiments of the present invention is that they display specific better anti-infectious, in particular, anti-parasitic, activity than similar known compounds. The α-phenyl derivatives of the invention can be easily produced in good yield and purity from a cinnamaldehyde having a specific substitution pattern on the phenyl ring through a limited number of fully reproducible synthetic process steps. It is another aspect of the invention to provide a method allowing a broad range of substituted alpha-phenyl fosmidomycin derivatives. Said method comprises the step of reacting an alpha-tributylstannyl propenyl phosphonate synthon with an appropriately substituted aryl iodide or heteoaryl iodide. The present invention also relates to pharmaceutical compositions comprising a therapeutically effective amount of such novel organo-phosphoric derivatives, and optionally one or more pharmaceutically acceptable carriers. The present invention also relates to the use of such organophosphoric derivatives for making a medicament for treating or preventing infectious, e.g. parasitic, bacterial or fungal, disorders (in particular malaria) by the administration of said medicament to a patient in need thereof. Optionally said medicament can be administered in combination with one or more other drugs such as, but not limited to, other anti-infectious or anti-parasitic agents. In particular, this invention relates to such drug combinations having synergistic activity.

DEFINITIONS

As used herein, and unless otherwise stated, the term "$C_{1-7}$ alkyl" means straight and branched chain saturated acyclic hydrocarbon monovalent groups having from 1 to 7 carbon atoms such as, for example, methyl, ethyl, propyl, n-butyl, 1-methylethyl (isopropyl), 2-methylpropyl (isobutyl), 1,1-dimethylethyl (ter-butyl), 2-methylbutyl, n-pentyl, dimethylpropyl, n-hexyl, 2-methylpentyl, 3-methylpentyl, n-heptyl and the like; said $C_{1-7}$ alkyl group may further optionally include one or more suitable substituents independently selected from the group consisting of amino, halogen, hydroxy, sulfhydryl, trifluoromethyl, methoxy and the like.

As used herein, and unless otherwise stated, the terms "cycloaliphatic" and "$C_{3-10}$ cycloalkyl" refer to a mono- or polycyclic saturated hydrocarbon monovalent group having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent group having from 7 to 10 carbon atoms such as, for instance, norbornyl, fenchyl, trimethyltricycloheptyl or adamantyl.

As used herein, the term "$C_{3-10}$ cycloalkyl-alkyl" refers to an aliphatic saturated hydrocarbon monovalent group (preferably a $C_{1-7}$ alkyl such as defined above) to which a $C_{3-10}$ cycloalkyl (such as defined above) is linked such as, but not limited to, cyclohexylmethyl, cyclopentylmethyl and the like.

As used herein, and unless otherwise stated, the terms "aromatic" and "aryl" designate any mono- or polycyclic aromatic monovalent hydro-carbon group having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups (the latter being as defined above) such as, for instance, indanyl, tetrahydronaphthyl, fluorenyl and the like, all of the said groups being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, and unless otherwise stated, the term "heterocyclic" means a mono- or polycyclic, saturated or mono-unsaturated or poly-unsaturated monovalent hydrocarbon group having from 2 up to 15 carbon atoms and including one or more heteroatoms in one or more rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including groups wherein a heterocyclic ring is fused to one or more aromatic hydrocarbon rings for instance in the form of benzo-fused, dibenzo-fused or naphtho-fused heterocyclic groups; within this definition are included heterocyclic groups such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepinyl, benzodioxepinyl, benzodithiepinyl, benzoxazocinyl, benzothiazocinyl, benzodiazocinyl, benzoxathiocinyl, benzo-dioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypoxanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzocarbazolyl, dibenzoacridinyl, dibenzophenazinyl, dibenzothiepinyl, dibenzooxepinyl, dibenzopyranonyl, dibenzoquinoxalinyl, dibenzothiazepinyl, dibenzoiso-quinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphtho-pyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzo-dihydrofuryl, benzothiopyronyl, benzothiopyranyl, benzoxazinyl, benzoxazolyl, benzodioxolyl, benzodioxanyl, benzothiadiazolyl, benzotriazinyl, benzo-thiazolyl, benzoxazolyl, phenothioxinyl, phenothiazolyl, phenothienyl (benzothiofuranyl), phenopyronyl, phenoxazolyl, pyridinyli, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphthothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimidazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzo-carbazolyl, benzochromonyl, benziso-alloxazinyl, benzocoumarinyl, thiocoumarinyl, phenometoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof, wherein each carbon atom of said heterocyclic ring may be independently substituted with a substituent selected from the group consisting of halogen, nitro, $C_{1-7}$ alkyl (such as above defined, in particular methyl), $C_{3-7}$ alkenyl, trifluoromethyl, $C_{3-10}$ cycloalkyl, aryl, arylalkyl, alkylaryl, hydroxyl, sulfhydryl, $C_{1-7}$ alkoxy (such as above defined, in particular methoxy), aryloxy, arylalkyloxy, thio $C_{1-7}$ alkyl, thio $C_{3-10}$ cycloalkyl, thioaryl, arylalkylthio, cyano, carboxylic acid or esters thereof; depending upon the number of unsaturations in each of said rings, heterocyclic groups may be sub-divided into heteroaromatic (or "heteroaryl") groups and non-aromatic heterocyclic groups; when a heteroatom of the said non-aromatic heterocyclic group is nitrogen, the latter may be substituted with a substituent selected from the group consisting of $C_{1-7}$ alkyl, $C_{3-10}$ cycloalkyl, aryl, arylalkyl and alkylaryl (each of said groups being as defined herein).

As used herein, and unless otherwise stated, the term "$C_{1-7}$ alkoxy" refer to substituents wherein a $C_{1-7}$ alkyl group is attached to an oxygen atom through a single bond, such as but not limited to methoxy, ethoxy, propoxy, butoxy, pentoxy, isopropoxy, sec-butoxy, tert-butoxy, isopentoxy, and the like.

As used herein, and unless otherwise stated, the term "halogen" means any atom selected from the group consisting of fluoro, chloro, bromo and iodo.

As used herein, and unless otherwise stated, the term "arylalkyl" refers to an aliphatic saturated hydrocarbon monovalent group (preferably a $C_{1-7}$ alkyl such as defined above) onto which an aryl group (such as defined above) is attached, and wherein the said aliphatic or aryl groups may be optionally substituted with one or more substituents independently selected from the group consisting of halogen, amino, hydroxyl, sulfhydryl, $C_{1-7}$ alkyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, and the like.

As used herein, and unless otherwise stated, the term "acyl" refers to a substituent derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, wherein said acids comprise an aliphatic, aromatic or heterocyclic group in the molecule. A more specific kind of "acyl" group within the scope of the above definition refers to a carbonyl (oxo) group adjacent to a $C_{1-7}$ alkyl, a $C_{3-10}$ cycloalkyl, an aryl, an arylalkyl or a heterocyclic group, all of them being such as herein defined. Suitable examples of acyl groups are to be found below.

Acyl groups originating from aliphatic or cycloaliphatic monocarboxylic acids are designated herein as aliphatic or cycloaliphatic acyl groups and include, but are not limited to, the following:
- alkanoyl (for example formyl, acetyl, propionyl, butyryl, isobutyryl, valeryl, isovaleryl, pivaloyl and the like);
- cycloalkanoyl (for example cyclobutanecarbonyl, cyclopentanecarbonyl, cyclohexanecarbonyl, 1-adamantanecarbonyl and the like);
- cycloalkyl-alkanoyl (for example cyclohexylacetyl, cyclopentylacetyl and the like);
- alkenoyl (for example acryloyl, methacryloyl, crotonoyl and the like);
- alkylthioalkanoyl (for example methylthioacetyl, ethylthioacetyl and the like);
- alkoxycarbonyl (for example methoxycarbonyl, ethoxycarbonyl, propoxycarbonyl, isopropoxycarbonyl, butoxycarbonyl, isobutoxycarbonyl and the like);
- alkylcarbamoyl (for example methylcarbamoyl and the like);
- (N-alkyl)-thiocarbamoyl (e.g. N-methyl-thiocarbamoyl and the like);
- alkylcarbamidoyl (e.g. methylcarbamidoyl and the like); and
- alkoxalyl (for example methoxalyl, ethoxalyl, propoxalyl and the like);

Acyl groups may also originate from aromatic monocarboxylic acids and include, but are not limited to, the following:
- aroyl (e.g. benzoyl, toluoyl, xyloyl, 1-naphthoyl, 2-naphthoyl and the like);
- aralkanoyl (for example phenylacetyl and the like);
- aralkenoyl (for example cinnamoyl and the like);
- aryloxyalkanoyl (for example phenoxyacetyl and the like);
- arylthioalkanoyl (for example phenylthioacetyl and the like);
- arylaminoalkanoyl (for example N-phenylglycyl, and the like);
- aryloxycarbonyl (for example phenoxycarbonyl, naphthyloxycarbonyl and the like);
- aralkoxycarbonyl (for example benzyloxycarbonyl and the like);
- arylcarbamoyl (for example phenylcarbamoyl, naphthylcarbamoyl and the like);
- arylglyoxyloyl (for example phenylglyoxyloyl and the like).
- arylthiocarbamoyl (for example phenylthiocarbamoyl and the like); and
- arylcarbamidoyl (for example phenylcarbamidoyl and the like).

Acyl groups may also originate from an heterocyclic monocarboxylic acids and include, but are not limited to, the following:
- heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenoyl, furoyl, pyrrolecarbonyl, nicotinoyl and the like);
- heterocyclic-alkanoyl in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiopheneneacetyl, furylacetyl, imidazolylpropionyl, tetrazolylacetyl, 2-(2-amino-4-thiazolyl)-2-methoxyiminoacetyl and the like).

As used herein, "Het" refers to a 5- or 6-membered heteroaromatic ring which comprises 1, 2 or 3 heteroatoms independently selected from the group consisting of O, N and S.

As used herein and unless otherwise stated, the term "stereoisomer" refers to all possible different isomeric as well as conformational forms which the compounds of this invention may possess, in particular all possible stereochemically and conformationally isomeric forms, all diastereomers, enantiomers and/or conformers of the basic molecular structure.

As used herein and unless otherwise stated, the term "enantiomer" means each individual optically active form of a compound of this invention, having an optical purity or enantiomeric excess (as may be determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols, ketones, esters and the like.

DETAILED DESCRIPTION OF THE INVENTION

In a first aspect, the present invention relates to a family of novel phosphonic acid compounds having the structural formula (I):

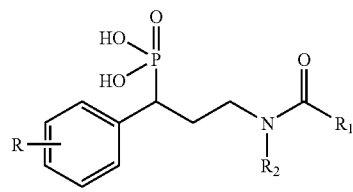

wherein:
R is a group of 1 to 5 substituents independently selected from the group consisting of halogen, $C_{1-4}$ alkoxy, $C_{1-4}$ alkyl, hydroxy, formyl, trifluoromethoxy, phenyl, heterocyclic (in particular pyrrolyl and pyrrolidinyl), heterocyclic-substituted methyl (in particular piperidinylmethyl, piperazinylmethyl and morpholinylmethyl), aminomethyl, hydroxymethyl, bromomethyl, sulfonyl chloride, acetyl chloride, nitroso, nitro, amino, trifluoromethyl and cyano, R₁ is selected from the group consisting of hydrogen, $C_{1-7}$ alkyl, $C_{3-10}$ cycloalkyl, aryl, arylalkyl and heterocyclic, and R₂ is selected from the group consisting of hydroxy and hydroxy-protecting groups, stereoisomers thereof, solvates thereof, pro-drugs thereof, or salts thereof.

Within this broad acceptance of the invention, each generic term such as, but not limited to, "$C_{1-4}$ alkoxy", "$C_{1-7}$ alkyl", "$C_{3-10}$ cycloalkyl", "hete-rocyclic", "arylalkyl" and "aryl" may, independently from each other, be understood according to any of the particular meanings thereof indicated in the above definitions.

A first embodiment of this aspect of the invention relates to compounds wherein R is a group of two or more substituents independently selected from the group consisting of fluoro, chloro, bromo, methoxy, nitroso and cyano.

Another embodiment of this aspect of the invention relates to such compounds wherein R is a group of two or more substituents, such as broadly defined in the above structural formula, wherein at least two such substituents are adjacent.

Another embodiment of this aspect of the invention relates to such compounds wherein R is a group of two identical substituents, such as broadly defined in the above structural formula; for instance said identical and possibly adjacent substituents may be chloro.

Another embodiment of this aspect of the invention relates to such compounds wherein R is a group of two different substituents such as broadly defined in the above structural formula. Another embodiment of this invention relates to such compounds wherein R is a group of five fluoro substituents.

Another embodiment of this invention relates to such compounds wherein R is a single substituent, such as broadly defined in the above structural formula. Said single substituent may advantageously be in a para position on the phenyl ring. Whether or not in a para position, said single substituent may advantageously be methoxy or chloro.

A second embodiment of this aspect of the invention relates to compounds wherein R₁ is such that, together with the adjacent carbonyl moiety, it forms an acyl group derived from an aliphatic, cycloaliphatic, aromatic or hereocyclic monocarboxylic acid. In view of the commercial availability of starting materials for an acylation step, a preferred but non limiting embodiment of this aspect of the invention relates to compounds wherein R₁ is selected from the group consisting of hydrogen, methyl, imidazolyl, triazolyl, benzyl, p-toluoyl, 1-naphthyl, 2-naphthyl, 4-morpholinyl, 1-piperidinyl, 1-imidazolidinyl, 1-pyrrolidinyl, 2-thiazolyl, 1-methyl-1H-pyrrole-2-yl, 2-furanyl, 3-furanyl, 3-pyridinyl, 4-pyridinyl, 2-thienyl, cyclobutyl, cyclopentyl, cyclohexyl, 1-adamantyl, and 2-norbornyl.

Another embodiment of this aspect of the invention relates to compounds wherein R₂ is a suitable hydroxy-protecting group. Such suitable hydroxy-protecting groups are well known in the art and are preferably selected from the group consisting of arylcarbonyl, alkylcarbonyl and aryl-alkylcarbonyl. A few non-limiting examples of such suitable hydroxy-protecting groups include benzyloxy, benzyloxycarbonyl (which may be introduced by reaction with benzyl chloroformate under alcaline conditions, e.g. making use of sodium hydroxide or hydrogenocarbonate) and 9-fluorenylmethoxycarbonyl (which may be introduced by reaction with 9-fluorenylmethyl chloroformate). Another example of a suitable hydroxy-protecting group is tert-butoxycarbonyl which may be introduced by reaction with di-tert-butyl dicarbonate under alcaline conditions. Other suitable hydroxy-protecting groups include triphenylmethyl (trityl) and trifluoroacetyl groups.

For pharmaceutical use, especially for the formulation of suitably bioavailable drug formulations, it may be preferred that the compound of the invention is present in the form of a non-toxic addition salt, more preferably a pharmaceutically acceptable salt, of a compound defined according to the above structural formula.

The latter form includes any therapeutically active non-toxic addition salt which the compounds of this invention are able to form with a salt-forming agent. Such addition salts may conveniently be obtained by treating the organophosphoric acid derivatives of the invention with an appropriate salt-forming base, following conventional procedures in the art. Examples of appropriate salt-forming bases include, for instance, inorganic bases like metallic hydroxides such as, but not limited to, hydroxides of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, lutidine, N,N'-dibenzylethylenediamine, chloroprocaine, choline, diethanol-amine, ethylenediamine, N-methylglucamine, procaine and the like.

For certain applications, it may be preferred that the compound of the invention be present in the form of an ester of a compound defined according to the above structural formula, i.e. a phosphonic acid ester. Such form in fact may also be a final intermediate in the synthetic procedure of said compound. Suitable esters include any ester which can be formed from or hydrolysed into the corresponding phosphonic acid derivative by using procedures conventional in the art, such as but not limited to a methyl or ethyl ester.

An advantage of the present invention is that compounds defined according to the above structural formula are easily accessible in good yield and purity through one or more synthetic schemes involving a limited number of process steps. A first exemplary but non-limiting method for preparing such compounds comprises one or more of the following steps, preferably performed in the following sequence of steps:

a step of reacting said R-substituted cinnamaldehyde, wherein R is a group of two or more substituents independently selected from the group consisting of fluoro, chloro, bromo, methoxy, nitroso and cyano, with a suitable amount (preferably an at least stoeichiometric amount) of a trialkyl phosphite in the presence of a suitable amount of a phenol to produce an acetal-phosphonic acid ester intermediate, a step of deprotecting said acetal-phosphonate intermediate under acidic conditions to produce the corresponding aldehyde-phosphonic acid ester intermediate, a step of reacting said aldehyde-phosphonic acid ester intermediate with a suitable amount (preferably an at least stoeichiometric amount) of an hydroxylamine, e.g. benzylhydroxylamine, to produce the corresponding oxime-phosphonic acid ester intermediate, a step of reducing said oxime-phosphonic acid ester intermediate to produce the corresponding benzyloxyamino derivative, a step of reacting said benzyloxyamino derivative with a suitable amount (preferably an at least stoeichiometric amount) of an activated carbonyl compound for producing the corresponding N-benzyloxyacetamide or N-benzyloxyformamide derivative; said activated carbonyl compound may suitably be selected from the group consisting of carboxylic acid chlorides, carboxylic acid anhydrides, carbamic acid chlorides, chloroformates, imidic acid chlorides, 1,1'-carbonyldiimidazole, 1,1'-carbonylditriazole, and mixtures thereof, and a combination of a carboxylic acid with 1,1'-carbonyldiimidazole or a N-acyl thiazolidine-2-thione.

Representative examples of optionally substituted cinnamaldehydes suitable as starting materials for the reaction of the first step include, but are not limited to, cinnamaldehyde, 4-bromocinnamaldehyde, 2-methoxycinnamaldehyde, 4-methoxy-cinnamaldehyde, 3-chlorocinnamaldehyde, 4-chlorocinnamaldehyde, 4-fluoro-cinnamaldehyde, 2-nitrocinnamaldehyde, 4-nitrocinnamaldehyde, and 4-cyanocinnamaldehyde.

Suitable experimental conditions, such as but not limited to, temperature, pressure and optional catalyst, for performing each of said above synthesis steps are well known in the art. In particular, suitable experimental conditions and reactive agents for performing the last mentioned step are well known in the art and, depending upon the selected activated carbonyl compound and the desired type of derivative (acetyl or formyl), may be tailored at will without undue experimentation.

When some final compounds of the invention defined according to the above structural formula are desired, e.g. when $R_2$ is hydroxy, this first above-referred general synthetic method preferably further comprises a step for selectively deprotecting the hydroxylamino group of the N-benzyloxy-acetamide or N-benzyloxyformamide derivative resulting from the previous step, without affecting any of the other functional groups being present in said intermediate derivative. For instance the hydroxylamino-protecting group (e.g., but not limited to, benzyl) may suitably be removed by deprotection methods conventional in the art such as, but not limited to:

when the protecting group is a benzyl group, cleavage of the benzylic ether function by hydrogenolysis, e.g. using $H_2$, Pd—C at about 25° C., or under strongly acidic conditions (e.g. making use of bromhydric acid), or when the protecting group is a tert-butoxycarbonyl group, by treatment with an acid, e.g. using aqueous hydrochloric acid or trifluoroacetic acid, under conditions mild enough to avoid further cleavage of the molecule, or when the protecting group is a 9-fluorenylmethoxycarbonyl group, by treatment with a base such as piperidine.

An advantage of the first method for preparing the compounds of this invention is that the required R-substituted cinnamaldehyde starting material either is commercially available or can easily be made, whatever the meaning of the group R of substituents, by using synthetic schemes and methods well known in the art.

A second exemplary but non-limiting method for preparing the compounds of this invention makes use of a R-substituted benzylphosphonic acid ester (wherein R is as defined in the above structural formula) as a starting material and comprises one or more of the following steps, preferably performed in the following sequence of steps:

reacting said R-substituted benzylphosphonic acid ester with a suitable amount (preferably an at least stoeichiometric amount) of an allyl halide, e.g. allyl bromide, preferably in the presence of a suitable amount of an alkyl lithium such as, but not limited to n-butyl lithium, to produce an R-substituted 1-arylbut-3-enylphosphonic acid ester;

converting the terminal alkenyl moiety of said R-substituted 1-arylbut-3-enylphosphonic acid ester into a terminal aldehyde moiety to produce the corresponding aldehyde phosphonic acid ester intermediate which can then be treated in a the same manner and with the same sequence of steps as in the first above-described synthetic method.

An advantage of the second synthetic method for preparing the compounds of this invention is that the required R-substituted benzyl-phosphonic acid ester (wherein R is as defined in the above structural formula) starting material either is commercially available or can easily be made, whatever the meaning of the group R of substituents, by using synthetic schemes and methods well known in the art.

A third exemplary but non-limiting method for preparing the compounds of this invention makes use of a alpha-tributylstannyl propenyl phosphonate intermediate or synthon according to the following formula:

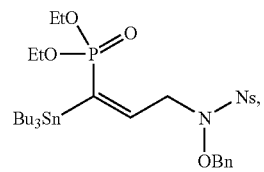

and comprises one or more of the following steps, preferably performed in the following sequence of steps:

reacting said alpha-tributylstannyl propenyl phosphonate synthon with a suitable amount (preferably an at least stoeichiolmetric amount) of an aryl or heteroaryl iodide to produce a 1-(R-substituted (hetero)aryl),3-(N-benzyloxy-2-nitrobenzenesulfonamido)-prop-1-enylphosphonic acid dialkyl ester;

converting the alkenyl moiety of the said 1-(R-substituted aryl),3-(N-benzyloxy-2-nitrobenzenesulfonamido)-prop-1-enylphosphonic acid dialkyl ester to produce the corresponding N-protected and O-protected propylphosphonic ester intermediate;

removing the N-protecting group, e.g. the nitrobenzenesulfonamido group, of said N-protected and O-protected propylphosphonic ester intermediate followed by acylation thereof, for example but not limited to formylation or acetylation;

removing the O-protecting group, i.e. the benzyl group, of the acylated product from the previous step by using any known method such as, but not limited to, reduction or acidic treatment; and hydrolysing the resulting phosphonic acid ester.

Suitable aryl and heteroaryl iodides suitable for the performance of this third method include, but are not limited to, 2,6-diodo-4-nitroaniline, 2-iodoaniline, 3-iodoaniline, 4-iodoaniline, 4-iodoanisole, 3-iodoanisole, 2-iodoanisole, iodobenzene, 1-iodo-4-nitrobenzene, 4-iodophenol, 3-iodophenol, 2-iodotoluene, 3-iodotoluene, 4-iodotoluene, 1-chloro-4-iodobenzene, 5-iodovanillin, 1-iodo-2-nitrobenzene, 1-iodo-3-nitrobenzene, 2,4,6-triodophenol, 2,6-diodo-4-nitrophenol, 1,4-dichloro-2-iodobenzene, 1,2-dichloro-3-iodobenzene, 2-iodobenzyl alcohol, 3-iodobenzyl alcohol, 1,3-dichloro-5-iodobenzene, 1-fluoro-4-iodobenzene, 1-fluoro-3-iodo-benzene, 1-fluoro-2-iodobenzene, pipsyl chloride, 1-chloro-3-iodobenzene, 1-bromo-2-iodobenzene, 4-iodobenzotrifluoride, 3-iodobenzotrifluoride, 2-iodobenzotrifluoride, 1-bromo-3-fluoro-4-iodobenzene, 1-bromo-2-fluoro-4-iodobenzene, 5-bromo-2-iodo-toluene, 1-ethyl-2-iodobenzene, 1-ethyl-4-iodobenzene, 1-tert-butyl-4-iodobenzene, 5-iodo-m-xylene, 4-iodo-m-xylene, 2-iodo-m-xylene, 4-iodo-o-xylene, 3-iodo-o-xylene, 3-iodo-4-nitroanisole, 4-iodobenzyl bromide, 2,4,6- trimethyliodobenzene, 1-(4-iodophenyl)pyrrole, 1-(4-iodobenzyl)morpholine, 1-(4-iodobenzyl)piperidine, 1-(4-iodobenzyl)-4-methylpiperazine, 1-(4-iodophenyl)pyrrolidine, 1,3-diiodobenzene, 4-iodobenzoyl chloride, 1-iodonaphthalene, 3-iodobenzylamine, 2-iodobenzaldehyde, 2-iodobiphenyl, 3-iodobenzonitrile, 2-fluoro-6-iodobenzonitrile, 1-(4-iodophenyl)-1H-pyrazole, 5-iodo-1H-indole, 4-fluoro-2-iodo-1-methylbenzene, 1-iodo-2-(trifluoro-methoxy)-benzene, 1-iodo-4-(trifluoromethoxy)benzene, 4-butyl-1-iodo-2-methyl-benzene and the like.

An advantage of this third method resides in the alpha-tributylstannyl propenyl phosphonate intermediate that is a common intermediate to a wide variety of final compounds in a late stage of the synthetic pathway. This advantage is highly relevant when the N-deprotection/acylation step is performed prior to the introduction of the alpha-tributylstannyl functionality.

In another embodiment, the method for obtaining the compounds of the present invention comprises the step of purifying the final compound on a CF11-cellulose column. Said embodiment is based on the finding that such technique achieves high yield with this type of phosphonic acid molecules. The method also allows to purify the phosphonic acid molecules as salts such as but not limited to ammonium salts. It is another advantage of this embodiment that it is a feasible method for larger scale purifications.

In another aspect, based on the fact that the above-defined novel organophosphoric derivatives exhibit biologically-active properties, the present invention relates to a pharmaceutical composition comprising a therapeutic effective amount of a compound defined by the above structural formula (with any of the available individual meanings for each of R, $R_1$ and $R_2$), and optionally one or more pharmaceutically acceptable carriers or excipients. Said pharmaceutical composition may comprise a novel organophosphoric derivative of the invention as the single bio-active ingredient, or as a bio-active ingredient in combination with one or more other drugs in a combined preparation for a so-called combination therapy.

Another embodiment of this aspect of the invention relates to the various precursor or so-called "pro-drug" forms of the compounds of the present invention. It may be desirable to formulate the compounds of the present invention in the form of a chemical species which when delivered to the body of a human or higher mammal will undergo a chemical reaction catalyzed by the normal function of the body, inter alia, enzymes present in the stomach and/or in blood serum of the patient, and/or in the targeted parasite or bacteria, said chemical reaction having the effect of releasing a therapeutically effective amount of the compound as defined herein. The term "pro-drug" thus relates to these species which are converted in vivo to the active pharmaceutical ingredient.

The pro-drugs of the present invention can have any form suitable for the formulator, for example, esters are common pro-drug forms. In the present case, however, the pro-drug may necessarily exist in a form wherein a covalent bond is cleaved by the action of an enzyme present at the target locus. For example, a C—C covalent bond and/or a P—N covalent bond may be selectively cleaved by one or more enzymes at said target locus and, therefore, a pro-drug in a form other than an easily hydrolysable precursor, inter alia esters, amides, and the like, may also be suitably used for therapeutic purpose.

For the purposes of the present invention the term "therapeutically suitable pro-drug" is defined herein as a compound modified in such a way as to be transformed in vivo into the therapeutically active form, whether by way of a single or by multiple biological transformations, when brought into contact with one or more tissues of a human being or other mammal to which said modified compound has been administered, and this in vivo transformation being effected without undue toxicity, irritation, or allergic response in said human being or other mammal, and while achieving the intended therapeutic outcome.

The term "pharmaceutically acceptable carrier or excipient" as used herein in relation to pharmaceutical compositions and combined preparations means any material or substance with which the bio-active principle(s), i.e. the organophosphoric derivative and the said one or more other drugs, may be formulated in order to facilitate application or dissemination to the locus to be treated, for instance by dissolving, dispersing or diffusing the said composition, and/or to facilitate its storage, transport or handling without impairing its effectiveness. The pharmaceutically acceptable excipient or carrier may be a solid or a liquid or a gas which has been compressed to form a liquid, i.e. the compositions of this invention can suitably be used in the form of concentrates, emulsions, solutions, granulates, dusts, sprays, aerosols, pellets or powders, but are not limited thereto.

Suitable pharmaceutical carriers or excipients for use in the pharmaceutical compositions of this invention, and their formulation methods, are well known to those skilled in the art. There is no particular restriction to their selection within the present invention although, in case of a low or very low water-solubility of the organophosphoric derivative of this invention, special attention must be paid to the selection of suitable carrier combinations that can assist in a proper formulation in view of the expected time release profile. Suitable pharmaceutical carriers or excipients include additives such as, but not limited to, wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided that the same are consistent with standard pharmaceutical practice, i.e. carriers and additives which do not create severe and/or permanent damage to the mammal, in particular the human being, to be treated with said medicament. The pharmaceutical compositions of the present invention may be prepared by any method well known in the art, for instance by homogeneously mixing, dissolving, spray-drying, coating and/or grinding the bio-active ingredient(s), in a one-step or a multi-steps procedure, with the selected carrier material(s) and, where appropriate, the other additives such as surface-active agents. The pharmaceutical compositions of the present invention may also be prepared by micronisation, for instance in view to obtain them in the form of microspheres usually having a diameter of about 1 to about 10 µm, namely for the manufacture of microcapsules for controlled or sustained release of the said biologically-active ingredient(s).

Suitable surface-active agents useful as a pharmaceutically acceptable carrier or excipient in the pharmaceutical compositions of the present invention include non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, non-substituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, non-substituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalene-sulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as, but not limited to, phosphatidyl-ethanolamine, phosphatidylserine, phosphatidylglycerine, lysolecithin, cardiolipin, dioctanylphosphatidylcholine, dipalmitoylphoshatidylcholine, and mixtures thereof in any suitable proportions.

Suitable non-ionic surfactants useful as pharmaceutically acceptable carriers or excipients in the pharmaceutical compositions of the present invention include, but are not limited to, polyethoxylated and polypropoxylated derivatives of alkylphenols, fatty alcohols, fatty acids, aliphatic amines or amides containing at least 12 carbon atoms in the molecule, alkylarene-sulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants include, but are not limited to, water-soluble adducts of polyethylene oxide with poylypropylene glycol, ethylenediaminopolypropylene glycol containing 1 to 10 carbon atoms in the alkyl chain, which adducts may contain about 20 to 250 ethyleneglycol ether groups and/or about 10 to 100 propyleneglycol ether groups. Such compounds usually contain from 1 to 5 ethyleneglycol units per propyleneglycol unit. Representative examples of such non-ionic surfactants are nonylphenol-polyethoxyethanol, castor oil polyglycolic ethers, polypropylene/polyethylene oxide adducts, tributyl-phenoxypolyethoxyethanol, polyethyleneglycolof various molecular weights, and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants useful as pharmaceutically acceptable carriers or excipients in the pharmaceutical compositions of the present invention include, but are not limited to, quaternary ammonium salts, preferably halides, having four hydrocarbon radicals optionally substituted with halo, phenyl, substituted phenyl and/or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated $C_1$-$C_4$ alkyl, benzyl and/or hydroxy-lower $C_1$-$C_4$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ edition (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents in particular include, but are not limited to, highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to about 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include, but are not limited to, additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as, but not limited to, silicates, diatomaceous earth, magnesium oxide or aluminum oxide; densification agents such as magnesium salts; and mixtures thereof.

Additional carriers or excipients may be included in order to control the duration of action of the biologically-active ingredient(s) into the compositions and combined preparations of the invention. Control release compositions may thus be achieved by selecting appropriate polymer carriers such as for example, but are not limited to, polyesters, polyaminoacids, polyvinylpyrrolidone, ethylene-vinyl acetate copolymers, methylcellulose, carboxymethyl-cellulose, protamine sulfate, and mixtures thereof in any suitable proportions. The rate of drug release and/or duration of action may also be effectively controlled by incorporating the biologically-active ingredient of this invention into particles, e.g. microcapsules, of a polymeric substance such as hydrogels, polylactic acid, hydroxymethyl-cellulose, polymethyl methacrylate and one or more of the other above-described polymers. Such methods include colloid drug delivery systems such as, but not limited to, liposomes, microspheres, microemulsions, nanoparticles, nanocapsules and the like. Depending on the route of administration and the dosage form, the pharmaceutical composition or combined preparation of the invention may also require protective coatings of the types well known in the art.

Pharmaceutical forms suitable for injectable use include sterile aqueous solutions or dispersions and sterile powders for the extemporaneous preparation thereof. Typical carriers or excipients for this purpose therefore include biocompatible aqueous buffers, ethanol, glycerol, propylene glycol, polyethylene glycol, complexing agents such as, but not limited to, cyclodextrins, maltodextrins and the like, and mixtures thereof in any suitable proportions.

In another embodiment, this invention provides combinations, preferably synergistic combinations, of one or more organophosphoric derivatives represented by the above structural formula (with any of the available individual meanings for each of R, $R_1$ and $R_2$) with one or more biologically-active drugs being preferably selected from the group consisting of anti-infectious, in particular anti-parasitic, drugs. As is conventional in the art, the evaluation of a synergistic effect in a drug combination may be made by analysing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively. As will be explained in more detail herein-below, this principle may be applied to a number of desirable effects such as, but not limited to, an activity against parasitic or other infections. For instance the present invention relates to a pharmaceutical composition or combined preparation having synergistic effects against parasitic or other infections, but is not limited thereto.

In yet another embodiment, this invention provides the use of a organophosphoric derivative represented by the above structural formula (with any of the available individual meanings for each of R, $R_1$ and $R_2$) for the manufacture of a medicament for preventing or treating a parasitic or infectious disease or disorder. Such diseases and disorders include, but are not limited to, those in which a pathologic condition develops in a human being due to parasitic, bacterial or fungal action. A non limiting but most illustrative example of such infectious diseases and disorders is malaria.

In view of the above methods of treatment or prevention, the aforementioned compounds of the invention or pharmaceutical compositions (formulations) thereof may be administered by any conventional method including oral and parenteral (e.g. subcutaneous, intraperitoneal, intravascular or intramuscular) injection. The treatment may consist of a single dose or a plurality of doses of the biologically-active ingredient over a predetermined period of time.

Thus, the present invention involves a method of treating a patient suffering from an infection-related, preferably parasite-related, disorder by the administration of a therapeutically effective amount of one or more of the novel organophosphoric compounds described herein, or a pro-drug form thereof. The invention is therefore useful for, but is not limited to, the treatment of malaria in a patient, preferably a human being, in need thereof. Besides being useful for human treatment, the novel organophosphoric compounds of the present invention are also useful for the treatment of higher mammals, including pets and cattle such as, but not limited to, horses, dogs, cats, sheep and pigs.

The term "therapeutically-effective" as used herein refers to an amount of the biologically-active agent for use in anti-infection, e.g. anti-parasitic, therapy which achieves improvement in the severity of the symptoms of the relevant disorder, as may be determined by any practical or reproducible method known in the art. For oral administration, the pharmaceutical composition of this invention may be in the form of a dosage unit containing a predetermined amount of the biologically-active ingredient. Non-limiting examples of such dosage units are tablets or capsules. The therapeutically active amount of the active compound that can be administered and the dosage regimen for treating the relevant parasitic or infectious disease condition with a compound and/or pharmaceutical composition of this invention depends on a variety of factors, including the age, weight, sex and medical condition of the patient, the severity of the disease, the route and frequency of administration, and the particular compound used, and thus may vary in accordance with said factors.

The pharmaceutical composition of this invention may thus contain the biologically-active ingredient of this invention in a range from about 0.1 to about 2000 mg, preferably about 0.5 to 500 mg and more preferably about 1 to 100 mg per dosage unit. A daily dose of about 0.01 to 100 mg/kg body weight, preferably about 0.1 to 20 mg/kg body weight and more preferably about 0.1 to 10 mg/kg body weight, may be appropriate for administration to a human being. The daily dose may suitably be administered in one to four sub-doses per day. For veterinary purpose, the effective dose will be adapted to the relevant animal species, taking into account knowledge standard in the art.

The following examples are provided for illustration of the invention without limiting its scope in any way, and will be explained with reference to the following schemes.

EXAMPLE 1

Preparation of Organophosphoric Acid Compounds

A. Using the Aldehyde Synthon Route

Retro-synthetic analysis toward the synthesis of the desired phosphonic acid compounds is depicted in scheme 1 below, wherein Ar designates an aryl group. 3-aryl-3-phosphoryl-propanal was found to be a convenient precursor for this synthetic method.

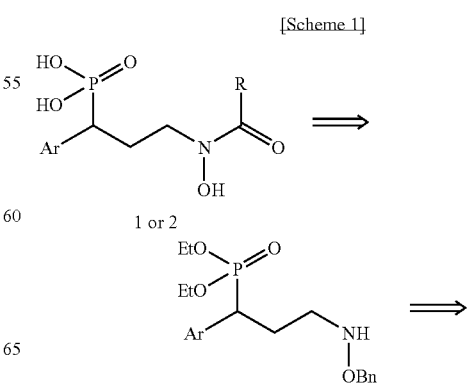

-continued

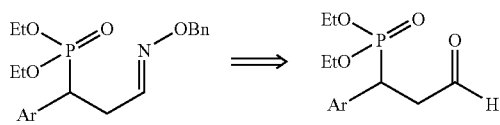

More specifically, two synthetic pathways toward the aldehyde synthon were explored, as shown in scheme 2 below. The first route started from allyl bromide which upon Arbusow reaction with the appropriate diethyl benzyl-phosphonate in the presence of n-BuLi, afforded intermediates 4a,b in 97% and 33% yield, respectively. Oxidation of 4a,b to the vicinal cis-diol with osmium tetraoxide in the presence of 4-methylmorpholine N-oxide was more preferable than an ozonolytic reaction. The vicinal diol was subsequently cleaved by sodium periodate, thus providing aldehydes 7a,b which were used in the next step without further purification.

When the desired benzylphosphonate was not commercially available, an alternative strategy to prepare the desired aldehydes was followed. A 1,4-addition of triethyl phosphite to the appropriately substituted cinnamaldehyde in the presence of phenol gave the acetals 6c-e in 70-85% yield, depending upon the one or more substituent(s) being present on the phenyl ring. Subsequent deprotection afforded in 76-83% yield the corresponding aldehydes, which were stable enough to be purified by flash chromatography. If necessary, other substituted cinnamaldehydes than those used herein may be prepared, using synthesis procedures described in the literature such as, but not limited to, a palladium-catalyzed synthesis from acrolein diethyl acetal and the corresponding aryl or heteroaryl iodide.

[Scheme 2]

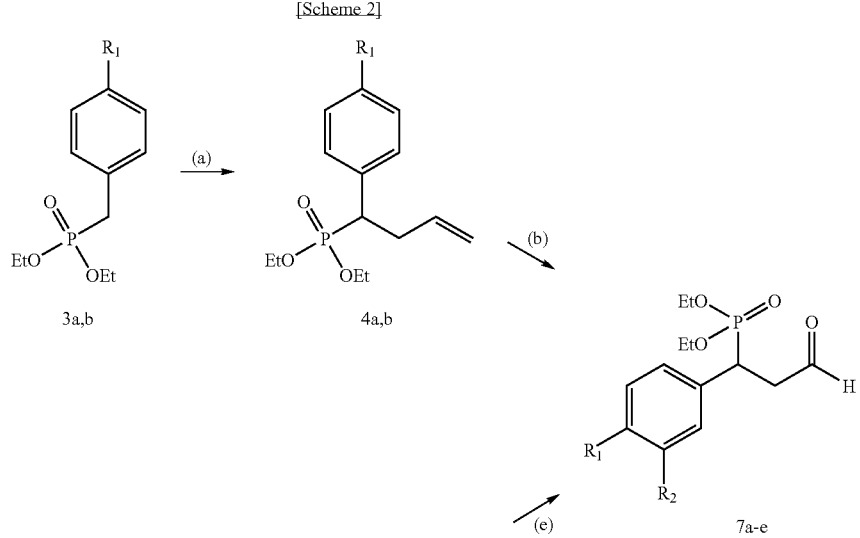

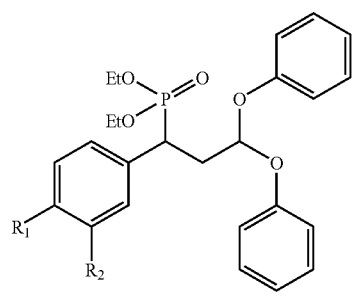

-continued

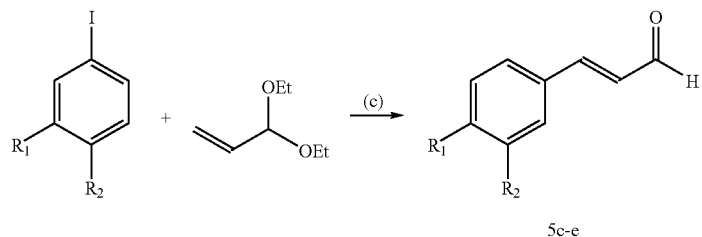

a: $R_1 = H; R_2 = H$
b: $R_1 = Me; R_2 = H$
c: $R_1 = OMe; R_2 = H$
d: $R_1 = Cl; R_2 = H$
e: $R_1 = Cl; R_2 = Cl$

The remainder of the synthesis is depicted in scheme 3 below, which will be explained in further details.

Treatment of 7a-e with O-benzylhydroxylamine yielded (67-92%) oximes 8a-e, which appeared as geometric isomers as revealed by NMR. O-benzyloximes 8a-e were reduced with sodium cyanoborohydride to produce benzyloxyamines 9a-e in 91-96% yield. Acetylation of 9a-e with acetyl chloride afforded 11a-e in good yield. Compounds 9c,e were then formylated by means of a mixture of formic acid and 1,1'-carbonyl-diimidazole. Subsequent benzyl deprotection by catalytic hydrogenation gave 12c,e and 13a-e, which occurred as mixtures of two hydroxamic acid isomers (syn and anti). Compounds 12c,e and 13a-e were finally deprotected with TMSBr in $CH_2Cl_2$ to afford pure 1c,e and 2a-e after purification by reversed phase high performance liquid chromatography (HPLC).

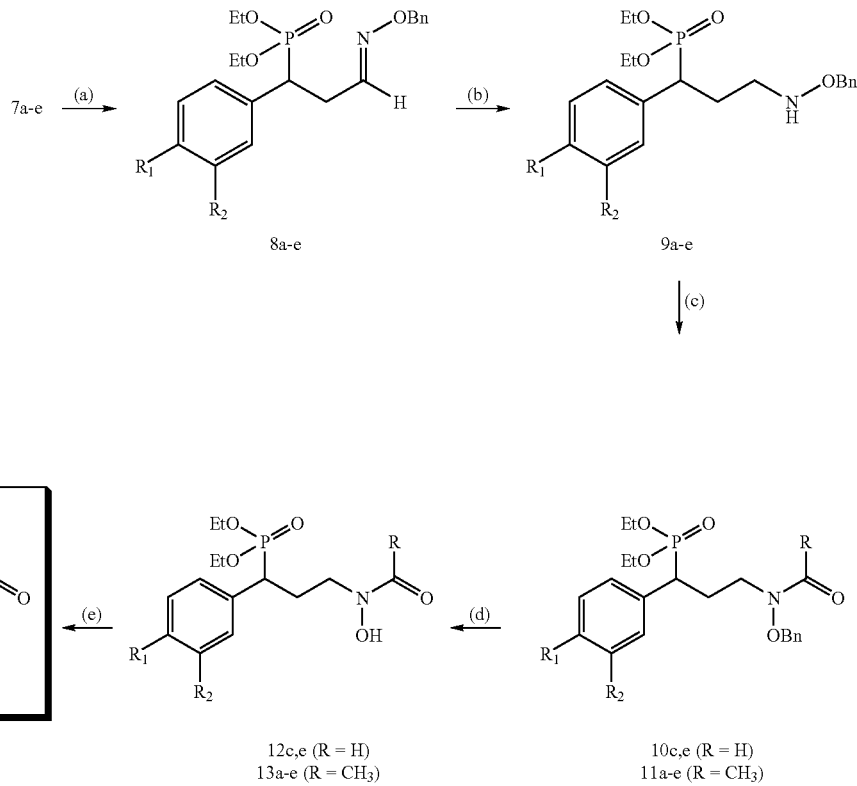

The following is a detailed description of experimental conditions used in the generally outlined schemes above. All reactions were carried out under inert ($N_2$) atmosphere. Precoated Merck silica gel $F_{254}$ plates and pre-coated Macherey-Nagel (Duren, Germany) silica gel $F_{254}$ plates were used for thin layer chromatography (TLC) and spots were examined under UV light at 254 nm and revealed by a phosphomolybdic-cerium sulphate solution, a iodine vapour or a dinitrophenol solution. Column chromatography was performed on Uetikon silica (0.2-0.06 mm) and ICN silica gel (63-200 μM). NMR spectra were obtained with a Varian Mercury 300 spectrometer. Chemical shifts are given in parts per million (ppm) (δ relative to residual solvent peak, in the case of DMSO-$d_6$ 2.54 ppm for $^1H$ and 40.5 ppm for $^{13}C$, in the case of $CDCl_3$ 7.26 ppm for $^1H$ and 77.4 ppm for $^{13}C$ and in the case of acetone 2.05 ppm for $^1H$ and 29.84 and 206.26 ppm for $^{13}C$. Coupling constants are expressed in Hz. Abbreviations used are: s=singlet, d=doublet, t=triplet, q=quartet, m=multiplet, br=broad. All signals assigned to hydroxyl and to amino groups were exchangeable with $D_2O$. Mass spectra and exact mass measurements were performed on a quadrupole/orthogonal-acceleration time-of-flight (Q/oaTOF) tandem mass spectrometer (qT of 2, available from Micromass, Manchester, United Kingdom) equipped with a standard electro-spray ionization (ESI) interface. Samples were infused in an acetonitrile/water (1:1) mixture at 3 μL/minute. Most chemicals were obtained from Sigma-Aldrich or Acros Organics and were used without further purification.

Diethyl 1-phenylbut-3-enylphosphonate (4a)

To a stirred solution of 3a (12 mL, 57.4 mmol) in dry THF (100 mL), cooled at −50 to −70° C., was added under $N_2$ at atmosphere a 1.6 M solution of nBuLi (39 mL, 63.2 mmol) in hexane. After stirring for 15 minutes at the same temperature allyl bromide (5 mL, 57.4 mmol) was added. One hour after this addition the reaction mixture was refluxed for 2 hours. After cooling to room temperature the reaction mixture was evaporated in vacuo, and the resulting oil was diluted with toluene (200 mL), washed with 10% $NH_4Cl$ (200 mL) and water (200 mL), dried over $MgSO_4$ and concentrated in vacuo. Purification of the residue by flash chromatography (n-hexane/ethyl acetate volume ratio 8:2 then 7:3 and then 6:4) yielded compound 4a as a transparent oil (97%) which was characterised as follows.

$^1$H-NMR (300 MHz, $CDCl_3$) δ: 1.06 (3H, t, $J_{HH}$=7.0 Hz, $OCH_2CH_3$); 1.25 (3H, t, $J_{HH}$=7.0 Hz, $OCH_2CH_3$); 2.61-2.74 (1H, m, allyl $CH_2$); 2.76-2.88 (1H, m, allyl $CH_2$); 3.05 (1H, ddd, $J_{HP}$=22.0 Hz, $J_{HH}$=4.4 Hz en $J_{HH}$=11.1 Hz, CHP); 3.62-3.75 (1H, m, $OCH_2CH_3$); 3.80-3.93 (1H, m, $OCH_2CH_3$); 3.95-4.09 (2H, m, $OCH_2CH_3$); 4.85-4.89 (1H, m, CH=$CH_2$, cis); 4.93-5.00 (1H, m, CH=$CH_2$, $_{trans}$); 5.51-5.65 (1H, m, CH=$CH_2$), 7.17-7.30 (5H, m, arom. H);

$^{13}$C-NMR (75 MHz, $CDCl_3$) δ: 16.46 (d, $^3J_{CP}$=5.7 Hz, $OCH_2CH_3$); 16.63 (d, $^3J_{CP}$=6.0 Hz, $OCH_2CH_3$); 34.26 (d, $^2J_{CP}$=2.9, $CH_2$CHP); 44.81 (d, $^1J_{CP}$=137.1 Hz, CHP); 62.00 (d, $^2J_{CP}$=7.2 Hz, $OCH_2CH_3$); 62.77 (d, $^2J_{CP}$=7.2 Hz, $OCH_2CH_3$); 117.03; 127.34; 128.62; 129.55; 135.56; 135.82; and (ESI-MS): Calculated for $C_{14}H_{22}O_3P$ [M+H]$^+$: 269.1306. Found: 269.1292.

Diethyl 1-p-tolylbut-3-enylphosphonate (4b)

The same procedure as described herein-above for intermediate 4a was used to produce the title compound (yield: 33%) which was characterised as follows:

$^1$H-NMR (300 MHz, aceton-$d_6$) δ: 1.06 (3H, t, $J_{HH}$=7.3 Hz, $OCH_2CH_3$); 1.25 (3H, t, $J_{HH}$=7.0 Hz, $OCH_2CH_3$); 2.29 (3H, s, p-$CH_3$); 2.56-2.68 (1H, m, allyl $CH_2$); 2.70-2.83 (1H, m, allyl $CH_2$); 3.10 (1H, ddd, $J_{HP}$=22.0 Hz, $J_{HH}$=4.1 Hz en $J_{HH}$=11.1 Hz, CHP); 3.65-3.78 (1H, m, $OCH_2CH_3$); 3.79-3.92 (1H, m, $OCH_2CH_3$); 3.96-4.09 (2H, m, $OCH_2CH_3$); 4.83-4.88 (1H, m, CH=$CH_2$, cis); 4.93-5.00 (1H, m, CH=$CH_2$, $_{trans}$); 5.56-5.69 (1H, m, CH=$CH_2$), 7.11-7.14 (2H, m, arom. H); and 7.22-7.25 (2H, m, arom. H);

$^{13}$C-NMR (75 MHz, aceton-$d_6$) δ: 15.94 (d, $^3J_{CP}$=5.5 Hz, $OCH_2CH_3$); 16.12 (d, $^3J_{CP}$=5.7 Hz, $OCH_2CH_3$); 20.38 (p-$CH_3$); 34.35 (d, $^2J_{CP}$=2.6, $CH_2$CHP); 43.80 (d, $^1J_{CP}$=137.4 Hz, CHP); 61.38 (d, $^2J_{CP}$=7.2 Hz, $OCH_2CH_3$); 61.99 (d, $^2J_{CP}$=6.9 Hz, $OCH_2CH_3$); 116.11; 128.99; 129.58; 133.40; 136.15; and 136.43; and ESI-MS: Calculated for $C_{15}H_{24}O_3P$ [M+H]$^+$: 283.146. Found: 283.10.

(E)-3-(4-chlorophenyl)acrylaldehyde (5d)

To a stirred solution of 1-chloro-4-iodobenzene (2 g, 8.39 mmol) in DMF (30 mL) were added acrolein diethyl acetal (3.84 mL, 8.39 mmol), n-$Bu_4$NOAc (5.06 g, 16.8 mmol), $K_2CO_3$ (1.74 g, 12.6 mmol), KCl (0.63 g, 8.39 mmol) and Pd(OAc)$_2$ (0.056 g, 0.25 mmol). The mixture was stirred for 1.5 hour at 90° C. After cooling, 2 N HCl was slowly added and the reaction mixture was stirred at room temperature for 10 minutes. Subsequently, it was diluted with ether (200 mL) and washed with water (200 mL). The organic layer was dried over $MgSO_4$ and concentrated under reduced pressure. The residue was purified by flash chromatography (n-hexane/ethyl acetate mixture in a volume ratio 8:2) to give intermediate 5d (74% yield) which was characterised as follows:

$^1$H-NMR (300 MHz, $CDCl_3$) δ: 6.67 (1H, dd, CHC(O)H, J=7.6 and 16.1 Hz); 7.42 (1H, d, J=16.1 Hz, CH=CHC(O)H); 7.44 (4H, m, arom. H), and 9.69 (1H, d, J=7.6 Hz, C(O)H);

$^{13}$C-NMR (75 MHz, $CDCl_3$) δ: 129.19 (=CH), 129.65 (=CH), 129.83 (=CH), 132.73 (=C), 137.48 (=C), and 151.20 (=CH), 193.53 (C=O); and ESI-MS: Calculated for $C_9H_8ClO$ [M+H]$^+$: 167.0264. Found: 167.1

(E)-3-(3,4-Dichlorophenyl)acrylaldehyde (5e)

The same synthetic procedure as described for intermediate 5d, but starting from 1,2-dichloro-4-iodobenzene gave 58% of the title compound which was characterised as follows:

$^1$H-NMR (300 MHz, $CDCl_3$) δ: 6.68 (1H, dd, CHC(O)H, J=7.3 and 16.1 Hz); 7.37 (1H, d, J=16.1 Hz, CH=CHC(O)H); 7.45 (3H, m, arom. H), and 9.71 (1H, d, J=7.3 Hz, C(O)H);

$^{13}$C-NMR (75 MHz, $CDCl_3$) δ: 127.42 (=CH), 130.12 (=CH), 130.26 (=CH), 131.36 (=CH), 133.80 (=C), 134.22 (=C), 135.48 (=C); 149.56 (=CH); and 193.14 (C=O); and ESI-MS): Calculated for $C_9H_7Cl_2O$ [M+H]$^+$: 200.9874. Found: 200.1.

General Method for the Synthesis of Intermediates 6c-e

A mixture of the appropriate acryl aldehyde (6.17 mmol), triethylphosphite (1.34 mL, 7.71 mmol) and phenol (1.54 g, 16 mmol) was heated to 100° C. After 24 hours, TLC analysis (hexane/ethyl acetate mixture in a 6:4 volume ratio) indicated that the reaction was completed. The reaction mixture was subsequently evaporated, and the crude product was purified by flash chromatography using a hexane/ethyl acetate mixture in a 6:4 volume ratio. After evaporation of the pure fractions, the desired acetals 6c-e were obtained in the form of slightly yellow oils.

Diethyl 1-(4-methoxyphenyl)-3,3-diphenoxypropylphosphonate (6c)

(yield: 81%) was characterised as follows:
$^1$H-NMR (300 MHz, CDCl$_3$) δ: 1.08 (3H, t, $J_{HH}$=7.0 Hz, OCH$_2$CH$_3$); 1.25 (3H, t, $J_{HH}$=7.0 Hz, OCH$_2$CH$_3$); 2.45-2.59 (1H, m, PCHCH$_2$); 2.68-2.79 (1H, m, PCHCH$_2$); 3.36 (1H, ddd, $J_{HP}$=22.4 Hz, $J_{HH}$=4.6 Hz and $J_{HH}$=10.9 Hz, CHP); 3.64-3.75 (1H, m, OCH$_2$CH$_3$); 3.80 (3H, s, OCH$_3$); 3.83-3.96 (1H, m, OCH$_2$CH$_3$); 3.97-4.10 (2H, m, OCH$_2$CH$_3$); 5.61 (1H, dd, $J_{HH}$=7.3 Hz and $J_{HH}$=3.8 Hz, CH(OPh)$_2$); 6.81-6.92 (6H, m, arom. H); 6.95-7.02 (1H, m, arom. H); and 7.18-7.30 (7H, m, arom. H);
$^{13}$C-NMR (75 MHz, CDCl$_3$) δ: 16.45 (d, $^3J_{CP}$=7.2 Hz, OCH$_2$CH$_3$); 16.53 (d, $^3J_{CP}$=6.1 Hz, OCH$_2$CH$_3$); 34.89 (PCHCH$_2$); 39.51 (d, $^1J_{CP}$=140.2 Hz, CHP); 55.31 (OCH$_3$); 62.07 (d, $^2J_{CP}$=7.2 Hz, OCH$_2$CH$_3$); 62.93 (d, $^2J_{CP}$=7.2 Hz, OCH$_2$CH$_3$); 99.60 (d, $^3J_{CP}$=16.7 Hz, CH(OPh)$_2$); 114.36 (d, =CH); 117.58 (=CH); 117.73 (=CH); 122.68 (=CH); 122.81 (=CH); 127.15 (d, =C); 129.71 (=CH); 129.72 (=CH); 130.44 (d, =CH); 156.18 (=C); 156.31 (=C); and 159.22 (d, =C);
$^{31}$P-NMR (120 MHz, CDCl$_3$) δ=29.09; and
ESI-MS: Calculated for C$_{26}$H$_{32}$O$_6$P [M+H]$^+$: 471.1937. Found: 471.2.

Diethyl 1-(4-chlorophenyl)-3,3-diphenoxypropylphosphonate (6d)

(yield: 85%) was characterised as follows:
$^1$H-NMR (300 MHz, CDCl$_3$) δ: 1.09 (3H, t, $J_{HH}$=7.0 Hz, OCH$_2$CH$_3$); 1.25 (3H, t, $J_{HH}$=7.0 Hz, OCH$_2$CH$_3$); 2.46-2.60 (1H, m, PCHCH$_2$); 2.71-2.83 (1H, m, PCHCH$_2$); 3.41 (1H, ddd, $J_{HP}$=22.6 Hz, $J_{HH}$=4.7 Hz and $J_{HH}$=10.6 Hz, CHP); 3.67-3.80 (1H, m, OCH$_2$CH$_3$); 3.85-3.96 (1H, m, OCH$_2$CH$_3$); 3.98-4.11 (2H, m, OCH$_2$CH$_3$); 5.63 (1H, ddd, $J_{HH}$=7.3 Hz and $J_{HH}$=4.4 Hz, $J_{HP}$=0.88 Hz, CH(OPh)$_2$); 6.81-6.92 (4H, m, arom. H); 6.96-7.02 (2H, m, arom. H); and 7.18-7.26 (8H, m, arom. H);
$^{13}$C-NMR (75 MHz, CDCl$_3$) δ: 16.46 (d, $^3J_{CP}$=5.8 Hz, OCH$_2$CH$_3$); 16.56 (d, $^3J_{CP}$=6.1 Hz, OCH$_2$CH$_3$); 34.70 (PCHCH$_2$); 39.88 (d, $^1J_{CP}$=139.9 Hz, CHP); 62.39 (d, $^2J_{CP}$=7.5 Hz, OCH$_2$CH$_3$); 63.13 (d, $^2J_{CP}$=7.2 Hz, OCH$_2$CH$_3$); 99.47 (d, $^3J_{CP}$=16.7 Hz, CH(OPh)$_2$); 117.67 (=CH); 117.73 (=CH); 122.91 (d, =CH); 129.13 (=CH); 129.16 (=CH); 129.79 (=CH); 129.81 (=CH); 130.77 (d, =CH); 133.67 (=C); 134.24 (=Oq); 156.09 (=C); and 156.11 (=C); and
ESI-MS: Calculated for C$_{25}$H$_{28}$ClO$_5$PNa [M+Na]$^+$: 497.126. Found: 497.126.

Diethyl 1-(3,4-dichlorophenyl)-3,3-diphenoxypropylphosphonate (6e)

(yield: 70%) was characterised as follows:
$^1$H-NMR (300 MHz, CDCl$_3$) δ: 1.13 (3H, t, $J_{HH}$=7.0 Hz, OCH$_2$CH$_3$); 1.25 (3H, t, $J_{HH}$=7.0 Hz, OCH$_2$CH$_3$); 2.43-2.57 (1H, m, PCHCH$_2$); 2.70-2.82 (1H, m, PCHCH$_2$); 3.38 (1H, ddd, $J_{HP}$=22.7 Hz, $J_{HH}$=4.7 Hz and $J_{HH}$=10.3 Hz, CHP); 3.74-3.87 (1H, m, OCH$_2$CH$_3$); 3.89-3.99 (1H, m, OCH$_2$CH$_3$); 3.99-4.12 (2H, m, OCH$_2$CH$_3$); 5.66 (1H, dd, $J_{HH}$=6.8 Hz and $J_{HH}$=4.4 Hz, CH(OPh)$_2$); 6.84-6.92 (3H, m, arom. H); 6.97-7.03 (2H, m, arom. H); 7.18-7.27 (6H, m, arom. H); and 7.37-7.45 (2H, m, arom. H);
$^{13}$C-NMR (75 MHz, CDCl$_3$) δ: 16.51 (app t, $^3J_{CP}$=5.8 Hz, OCH$_2$CH$_3$); 34.61 (d, PCHCH$_2$); 39.70 (d, $^1J_{CP}$=139.9 Hz, CHP); 62.57 (d, $^2J_{CP}$=7.2 Hz, OCH$_2$CH$_3$); 63.16 (d, $^2J_{CP}$=6.6 Hz, OCH$_2$CH$_3$); 99.34 (d, $^3J_{CP}$=15.8 Hz, CH(OPh)$_2$); 117.66 (=CH); 117.68 (=CH); 122.99 (=CH); 123.01 (=CH); 128.75 (d, =CH); 129.83 (=CH); 129.85 (=CH); 130.81 (d, =CH); 131.29 (d, =CH); 131.87 (d, =C); 133.01 (d, =C); 136.27 (d, =C); 155.95 (=C); and 156.04 (=C); and
ESI-MS: Calculated for C$_{25}$H$_{27}$Cl$_2$O$_5$PNa [M+Na]$^+$: 531.0871. Found: 531.0872.

General Method for the Synthesis of Intermediates 7a,b

To a mixture of alkene 4a or 4b (6.56 mmol) and 4-methylmorpholine N-oxide (0.92 g, 7.87 mmol) in dioxane (40 mL) was added an aqueous 1% solution of OsO$_4$ (99.1 mg, 0.39 mmol). After stirring overnight at room temperature and protected from light, the starting material was completely converted according to TLC. Then sodium periodate (2.24 g, 10.5 mmol) was added in small portions. After completion of the reaction (2 hours), the mixture was diluted with ethyl acetate (100 mL), filtered through Celite, and solids were washed with ethyl acetate. The combined filtrates were washed with saturated aqueous NaCl (100 mL), dried over MgSO$_4$, and evaporated under vacuum to yield crude 7a or 7b, which were used in the next step without further purification.

General Method for the Synthesis of Intermediates 7c-e

Acetals 6c-e (5.0 mmol) obtained in the previous step were hydrolysed by treatment with a mixture of water (7 mL), acetone (35 mL) and 2 N HCl (8 mL). After heating to 60-70° C. for 3 to 4 hours, TLC analysis (ethyl acetate) confirmed that the reaction was completed. Solvents were evaporated under vacuum, and the residue was dissolved in ethyl acetate (200 mL) and transferred to a separation funnel where it was washed twice with water (200 mL). The organic layer was dried with MgSO$_4$ and evaporated. The residue was purified by flash chromatography using ethyl acetate as an eluent, yielding 7c-e as transparent oils.

Diethyl 2-formyl-1-(4-methoxyphenyl)ethylphosphonate (7c)

(yield: 77%) was characterised as follows:
$^1$H-NMR (300 MHz, CDCl$_3$) δ: 1.12 (3H, t, $J_{HH}$=7.0 Hz, OCH$_2$CH$_3$); 1.27 (3H, t, $J_{HH}$=7.0 Hz, OCH$_2$CH$_3$); 2.99-3.20 (2H, m, PCHCH$_2$); 3.66 (1H, ddd, $J_{HP}$=22.6 Hz, $J_{HH}$=5.3 Hz and $J_{HH}$=9.1 Hz, CHP); 3.71-3.80 (1H, m, OCH$_2$CH$_3$); 3.78 (3H, s, OCH$_3$); 3.82-3.95 (1H, m, OCH$_2$CH$_3$); 3.97-4.09 (2H, m, OCH$_2$CH$_3$); 6.83-6.86 (2H, m, arom. H); 7.25-7.29 (2H, m, arom. H); and 9.66 (1H, app q, HC=O);
$^{13}$C-NMR (75 MHz, CDCl$_3$) δ: 16.57 (app t, $^3J_{CP}$=6.9 Hz, OCH$_2$CH$_3$); 37.32 (d, $^1J_{CP}$=142.2 Hz, CHP); 44.34 (PCHCH$_2$); 55.46 (OCH$_3$); 62.36 (d, $^2J_{CP}$=7.2 Hz, OCH$_2$CH$_3$); 63.16 (d, $^2J_{CP}$=6.9 Hz, OCH$_2$CH$_3$); 114.33 (d, $^4J_{CP}$=2.3 Hz, =C$_m$H); 127.14 (d, $^2J_{CP}$=7.2 Hz, =C$_i$); 130.35

(d, $^3J_{CP}$=6.6 Hz, =C$_o$H); 159.18 (d, $^5J_{CP}$=3.2 Hz, =C$_p$); and 199.41 (d, $^3J_{CP}$=15.8 Hz, HC=O);

$^{31}$P-NMR (120 MHz, CDCl$_3$) δ=28.49; and

ESI-MS: Calculated for C$_{14}$H$_{22}$O$_5$P [M+H]$^+$: 301.1205. Found: 301.1206.

Diethyl 1-(4-chlorophenyl)-2-formylethylphosphonate (7d)

(yield: 83%) was characterised as follows:

$^1$H-NMR (300 MHz, CDCl$_3$) δ: 1.13 (3H, t, J$_{HH}$=7.0 Hz, OCH$_2$CH$_3$); 1.27 (3H, t, J$_{HH}$=7.0 Hz, OCH$_2$CH$_3$); 3.00-3.23 (2H, m, PCHCH$_2$); 3.69 (1H, ddd, J$_{HP}$=22.7 Hz, J$_{HH}$=4.7 Hz and J$_{HH}$=9.4 Hz, CHP); 3.72-3.82 (1H, m, OCH$_2$CH$_3$); 3.83-3.96 (1H, m, OCH$_2$CH$_3$); 3.97-4.09 (2H, m, OCH$_2$CH$_3$); 7.28 (4H, s, arom. H); and 9.65-9.66 (1H, m, HC=O);

$^{13}$C-NMR (75 MHz, CDCl$_3$) δ: 16.43 (app t, $^3J_{CP}$=6.1 Hz, OCH$_2$CH$_3$); 37.30 (d, $^1J_{CP}$=142.2 Hz, CHP); 44.01 (PCHCH$_2$); 62.84 (d, $^2J_{CP}$=7.5 Hz, OCH$_2$CH$_3$); 63.44 (d, $^2J_{CP}$=7.2 Hz, OCH$_2$CH$_3$); 129.06 (d, $^4J_{CP}$=2.6 Hz, =C$_m$H); 130.63 (d, $^3J_{CP}$=6.3 Hz, =C$_o$H); 133.75 (d, $^5J_{CP}$=5.5 Hz, =C$_p$); 133.92 (d, $^2J_{CP}$=7.2 Hz, =C$_i$); and 198.55 (d, $^3J_{CP}$=15.8 Hz, HC=O); and ESI-MS: Calculated for C$_{13}$H$_{18}$ClO$_4$P [M+H]$^+$: 305.0710. Found: 305.0702.

Diethyl 1-(3,4-dichlorophenyl)-2-formylethylphosphonate (7e)

(yield: 76%) was characterised as follows:

$^1$H-NMR (300 MHz, CDCl$_3$) δ: 1.11 (3H, t, J$_{HH}$=7.0 Hz, OCH$_2$CH$_3$); 1.23 (3H, t, J$_{HH}$=7.0 Hz, OCH$_2$CH$_3$); 2.95-3.20 (2H, m, PCHCH$_2$); 3.62 (1H, ddd, J$_{HP}$=22.7 Hz, J$_{HH}$=4.7 Hz and J$_{HH}$=9.7 Hz, CHP); 3.74-3.83 (1H, m, OCH$_2$CH$_3$); 3.84-3.95 (1H, m, OCH$_2$CH$_3$); 3.96-4.07 (2H, m, OCH$_2$CH$_3$); 7.12-7.40 (4H, m, arom. H); and 9.61-9.62 (3H, m, HC=O);

$^{13}$C-NMR (75 MHz, CDCl$_3$) δ: 16.54 (app t, $^3J_{CP}$=6.2 Hz, OCH$_2$CH$_3$); 37.20 (d, $^1J_{CP}$=141.9 Hz, CHP); 44.09 (d, $^2J_{CP}$=2.3 Hz, PCHCH$_2$); 62.75 (d, $^2J_{CP}$=7.2 Hz, OCH$_2$CH$_3$); 63.34 (d, $^2J_{CP}$=6.9 Hz, OCH$_2$CH$_3$); 128.70 (d, $^3J_{CP}$=6.3 Hz, =C$_o$H); 130.75 (d, $^4J_{CP}$=2.6 Hz, =C$_m$H); 131.15 (d, $^3J_{CP}$=6.9 Hz, =COH); 131.95 (d, $^5J_{CP}$=3.7 Hz, =C$_p$); 132.92 (d, $^4J_{CP}$=2.9 Hz, =C$_m$); 136.03 (d, $^2J_{CP}$=7.2 Hz, =C$_i$); and 198.13 (d, $^3J_{CP}$=15.0 Hz, HC=O); and ESI-MS: Calculated for C$_{13}$H$_{18}$Cl$_2$O$_4$P [M+H]$^+$: 339.03204. Found: 339.0325.

General Method for the Synthesis of Intermediates 8a-e

A mixture of an aldehyde 7a-e (3.86 mmol) obtained in the previous step, and O-benzylhydroxylamine hydrochloride (0.61 g, 3.86 mmol) in a pyridine/ethanol (1:1) mixture (14 mL) was stirred for 1.5 hour to 6 hours at room temperature under nitrogen atmosphere. After the solvent was removed by evaporation, the residue was co-evaporated three times with toluene and subsequently submitted to chromatography on a silica gel column (n-hexane/ethyl acetate mixture in a volume ratio ranging from 6:4 to 1:1) to give a mixture of benzyloximes 8a-e in the form of transparent oils.

(E)-Diethyl 3-(benzyloxy)imino-1-phenylpropylphosphonate (8a)

(yield: 82%) was prepared from 6a and was characterised as follows:

$^1$H-NMR (300 MHz, CDCl$_3$) δ: 1.09 (3H, t, J$_{HH}$=7.0 Hz, OCH$_2$CH$_3$); 1.27 (3H, dt, J$_{HH}$=7.0 Hz, J$_{HP}$=4.4 Hz, OCH$_2$CH$_3$); 2.79-3.15 (2H, m, CHPCH$_2$); 3.16-3.33 (1H, m, PCH); 3.64-3.78 (1H, m, OCH$_2$CH$_3$); 3.82-3.94 (1H, m, OCH$_2$CH$_3$); 3.95-4.10 (2H, m, OCH$_2$CH$_3$); 4.98 (1H, s, OCH$_2$Ph); 5.08 (1H, s, OCH$_2$Ph); 6.56 (1H, t, J$_{HH}$=5.0 Hz, HC=N); and 7.24-7.33 (10H, m, arom. H);

$^{13}$C-NMR (75 MHz, CDCl$_3$) δ: 16.46 (d, $^3J_{CP}$=5.8 Hz, OCH$_2$CH$_3$); 16.63 (d, $^3J_{CP}$=7.2 Hz, OCH$_2$CH$_3$); 26.68 (d, CH$_2$CHP); 30.33 (d, $^2J_{CP}$=2.3 Hz, CH$_2$CHP); 41.73 (d, $^1J_{CP}$=139.8 Hz, CHP); 42.55 (d, $^1J_{CP}$=139.1 Hz, CHP); 62.26 (d, $^2J_{CP}$=4.9 Hz, OCH$_2$CH$_3$); 62.36 (d, $^2J_{CP}$=4.9 Hz, OCH$_2$CH$_3$); 63.00 (d, $^2J_{CP}$=2.9 Hz, OCH$_2$CH$_3$); 63.09 (d, $^2J_{CP}$=2.9 Hz, OCH$_2$CH$_3$); 75.87 (OCH$_2$Ph); 76.14 (OCH$_2$Ph); 127.75 (m, arom. C); 128.03 (d, arom. C); 128.28 (d, arom. C); 128.60 (d, arom. C); 128.85 (m, arom. C); 129.43 (m, arom. C); 135.11 (m, arom. C); 137.89 (d, arom. C); 148.83 (d, $^3J_{CP}$=16.7 Hz, HC=N); and 149.37 (d, $^3J_{CP}$=15.8 Hz, HC=N); and ESI-MS: Calculated for C$_{20}$H$_{27}$NO$_4$P [M+H]$^+$: 376.1678. Found: 376.1670.

(E)-Diethyl 3-(benzyloxy)imino-1-p-tolylpropylphosphonate (8b)

(yield: 82%) was prepared from 6b and was characterised as follows:

$^1$H-NMR (300 MHz, CDCl$_3$) δ: 1.05 (3H, t, J$_{HH}$=7.0 Hz, OCH$_2$CH$_3$); 1.20 (3H, dt, J$_{HH}$=7.0 Hz, J$_{HP}$=4.4 Hz, OCH$_2$CH$_3$); 2.25 (3H, s, p-CH$_3$); 2.69-3.05 (2H, m, CHPCH$_2$); 3.06-3.22 (1H, m, PCH); 3.59-3.74 (1H, m, OCH$_2$CH$_3$); 3.77-3.88 (1H, m, OCH$_2$CH$_3$); 3.90-4.03 (2H, m, OCH$_2$CH$_3$); 4.92 (1H, s, OCH$_2$Ph); 5.02 (1H, s, OCH$_2$Ph); 6.49 (1H, t, J$_{HH}$=5.0 Hz, HC=N); and 7.02-7.29 (9H, m, arom. H);

$^{13}$C-NMR (75 MHz, CDCl$_3$) δ: 15.24 (d, $^3J_{CP}$=5.8 Hz, OCH$_2$CH$_3$); 15.39 (d, $^3J_{CP}$=6.1 Hz, OCH$_2$CH$_3$); 20.08 (p-CH$_3$); 25.46 (d, CH$_2$CHP); 29.08 (d, CH$_2$CHP); 40.04 (d, $^1J_{CP}$=139.6 Hz, CHP); 40.88 (d, $^1J_{CP}$=139.3 Hz, CHP); 60.99 (d, $^2J_{CP}$=7.2 Hz, OCH$_2$CH$_3$); 61.06 (d, $^2J_{CP}$=7.2 Hz, OCH$_2$CH$_3$); 61.70 (d, $^2J_{CP}$=6.9 Hz, OCH$_2$CH$_3$); 61.73 (d, $^2J_{CP}$=6.9 Hz, OCH$_2$CH$_3$); 74.57 (OCH$_2$Ph); 74.85 (OCH$_2$Ph); 126.74 (d, arom. C); 127.01 (d, arom. C); 127.32 (d, arom. C); 127.99 (m, arom. C); 128.32 (m, arom. C); 130.63 (m, arom. C); 136.10 (m, arom. C); 136.68 (d, arom. C); 147.76 (d, $^3J_{CP}$=17.0 Hz, HC=N); and 148.25 (d, $^3J_{CP}$=15.8 Hz, HC=N); and ESI-MS: Calculated for C$_{21}$H$_{29}$NO$_4$P [M+H]$^+$: 390.1834. Found: 390.2.

(E)-diethyl 3-(benzyloxy)imino-1-(4-methoxyphenyl)propylphosphonate (8c)

(yield: 67%) was characterised as follows:

$^1$H-NMR (300 MHz, CDCl$_3$) δ: 1.11 (3H, t, J$_{HH}$=7.0 Hz, OCH$_2$CH$_3$); 1.26 (3H, dt, J$_{HH}$=7.0 Hz, J$_{HP}$=4.4 Hz, OCH$_2$CH$_3$); 2.73-3.11 (2H, m, CHPCH$_2$); 3.12-3.27 (1H, m, PCH); 3.66-3.80 (1H, m, OCH$_2$CH$_3$); 3.77 and 3.83 (3H, 2×s, OCH$_3$, isomers); 3.82-3.94 (1H, m, OCH$_2$CH$_3$); 3.96-4.08 (2H, m, OCH$_2$CH$_3$); 4.98 (1H, s, OCH$_2$Ph); 5.08 (1H, s, OCH$_2$Ph); 6.55 (1H, t, J$_{HH}$=5.0 Hz, HC=N); 6.80-6.85 (2H, m, arom. H); and 7.19-7.34 (7H, m, arom. H);

$^{13}$C-NMR (75 MHz, CDCl$_3$) δ: 16.52 (d, $^3J_{CP}$=5.8 Hz, OCH$_2$CH$_3$); 16.64 (d, $^3J_{CP}$=5.6 Hz, OCH$_2$CH$_3$); 26.75 (d, CH$_2$CHP); 30.42 (d, CH$_2$CHP); 40.83 (d, $^1J_{CP}$=140.2 Hz, CHP); 41.64 (d, $^1J_{CP}$=139.9 Hz, CHP); 55.43 (OCH$_3$); 62.20 (d, $^2J_{CP}$=7.2 Hz, OCH$_2$CH$_3$); 62.27 (d, $^2J_{CP}$=7.2 Hz,

OCH$_2$CH$_3$); 62.94 (d, $^2J_{CP}$=6.9 Hz, OCH$_2$CH$_3$); 62.98 (d, $^2J_{CP}$=6.9 Hz, OCH$_2$CH$_3$); 75.81 (OCH$_2$Ph); 76.11 (OCH$_2$Ph); 114.27 (t, =CH); 126.72-127.11 (m, =C); 127.96 and 128.00 (d, =CH); 128.21 and 128.29 (d, =CH); 128.55 and 128.58 (d, =CH); 130.32-130.55 (m, =CH); 137.84 and 138.102 (d, =C); 148.94 (d, $^3J_{CP}$=17.3 Hz, HC=N); 149.46 (d, $^3J_{CP}$=16.1 Hz, HC=N); and 159.10-159.21 (m, =C); and ESI-MS: Calculated for C$_{21}$H$_{29}$NO$_5$P [M+H]$^+$: 406.1783. Found: 406.1793.

(E)-diethyl 3-(benzyloxy)imino-1-(4-chlorophenyl) propylphosphonate (8d)

(yield: 85% was characterised as follows:

$^1$H-NMR (300 MHz, CDCl$_3$) δ: 1.13 (3H, t, J$_{HH}$=7.0 Hz, OCH$_2$CH$_3$); 1.27 (3H, dt, J$_{HH}$=7.0 Hz, J$_{HP}$=3.8 Hz, OCH$_2$CH$_3$); 2.74-3.08 (2H, m, CHPCH$_2$); 3.18-3.32 (1H, m, PCH); 3.74-3.85 (1H, m, OCH$_2$CH$_3$); 3.86-3.96 (1H, m, OCH$_2$CH$_3$); 3.97-4.09 (2H, m, OCH$_2$CH$_3$); 4.97 (1H, s, OCH$_2$Ph); 5.08 (1H, s, OCH$_2$Ph); 6.54 (1H, t, J$_{HH}$=5.0 Hz, HC=N); and 7.19-7.35 (9H, m, arom. H);

$^{13}$C-NMR (75 MHz, CDCl$_3$) δ: 16.51 (d, $^3J_{CP}$=5.8 Hz, OCH$_2$CH$_3$); 16.62 (d, $^3J_{CP}$=6.9 Hz, OCH$_2$CH$_3$); 26.60 (d, $^2J_{CP}$=2.0 Hz, CH$_2$CHP); 30.26 (d, $^2J_{CP}$=2.0 Hz, CH$_2$CHP); 41.19 (d, J$_{CP}$=139.9 Hz, CHP); 41.80 (d, $^1J_{CP}$=139.6 Hz, CHP); 62.44 (d, $^2J_{CP}$=7.2 Hz, OCH$_2$CH$_3$); 62.50 (d, $^2J_{CP}$=7.2 Hz, OCH$_2$CH$_3$); 63.09 (d, $^2J_{CP}$=7.2 Hz, OCH$_2$CH$_3$); 75.89 (OCH$_2$Ph); 76.24 (OCH$_2$Ph); 128.02-128.11 (m, arom. =CH); 128.28 (=CH); 128.57-128.61 (m, =CH); 128.94-129.05 (m, =CH); 130.60-130.87 (m, =CH); 133.50-133.64 (m, =C); 133.70-134.02 (m, =C); 137.77-137.95 (m, =C); 148.21 (d, $^3J_{CP}$=17.0 Hz, HC=N); and 148.81 (d, $^3J_{CP}$=15.6 Hz, HC=N); and ESI-MS: Calculated for C$_{20}$H$_{26}$ClNO$_4$P [M+H]$^+$: 410.1288. Found: 410.1284.

(E)-diethyl 3-(benzyloxy)imino-1-(3,4-dichlorophenyl)propylphosphonate (8e)

(yield: 92% was characterised as follows:

$^1$H-NMR (300 MHz, CDCl$_3$) δ: 1.17 (3H, dt, J$_{HH}$=7.0 Hz, J$_{HP}$=1.47 Hz, OCH$_2$CH$_3$); 1.28 (3H, dt, J$_{HH}$=7.0 Hz, J$_{HP}$=3.2 Hz, OCH$_2$CH$_3$); 2.72-3.05 (2H, m, CHPCH$_2$); 3.17-3.32 (1H, m, PCH); 3.81-3.90 (1H, m, OCH$_2$CH$_3$); 3.93-3.98 (1H, m, OCH$_2$CH$_3$); 3.99-4.10 (2H, m, OCH$_2$CH$_3$); 4.97 (1H, s, OCH$_2$Ph); 5.08 (1H, s, OCH$_2$Ph); 6.55 (1H, t, J$_{HH}$=5.3 Hz, HC=N); and 7.11-7.39 (8H, m, arom. H); and ESI-MS: Calculated for C$_{20}$H$_{25}$Cl$_2$NO$_4$P [M+H]$^+$: 444.090. Found: 444.091.

General Procedure for the Synthesis of 9a-e

Sodium cyanoborohydride (12.95 mmol, 0.81 g) was added to a solution of the relevant O-benzyloxime 8a-e (2.59 mmol) obtained in the previous step in methanol (15 mL). Two drops of methyl orange indicator were added followed by drop-wise addition of concentrated hydrochloric acid, until the solution remained pink and milky for at least half an hour. The reaction mixture was stirred for 3 to 16 hours at room temperature. The solvent was removed under vacuum. The residue was taken up in CH$_2$Cl$_2$ (100 mL) and washed until alkaline with 1 M potassium hydroxide solution and extracted thrice with CH$_2$Cl$_2$ (3×100 mL). The combined organic extracts were dried MgSO$_4$, filtered and the solvent was removed. The residue was brought on silica column and eluted with CH$_2$Cl$_2$/MeOH mixture in a volume ratio 95:5 or n-hexane/ethyl acetate mixture in a 4:6 volume ratio. After evaporation of the appropriate fractions, the desired O-benzyloxyamine 9a-e were obtained as clear oils.

Diethyl 3-(benzyloxyamino)-1-phenylpropylphosphonate (9a)

(yield: 96%) was characterised as follows:

$^1$H-NMR (300 MHz, CDCl$_3$) δ: 1.09 (3H, dt, J$_{HH}$=7.0 Hz and J$_{HP}$=0.6 Hz, OCH$_2$CH$_3$); 1.27 (3H, t, J$_{HH}$=7.0 Hz, OCH$_2$CH$_3$); 2.14-2.30 (1H, m, CH$_2$CHP); 2.38-2.53 (1H, m, CH$_2$CHP); 2.81-2.90 (1H, m, CH$_2$N); 2.93-3.05 (1H, m, CH$_2$N); 3.25 (1H, ddd, J$_{HP}$=22.0 Hz, J$_{HH}$=4.7 Hz and J$_{HH}$=10.8 Hz, CHP); 3.64-3.79 (1H, m, OCH$_2$CH$_3$); 3.85-3.97 (1H, m, OCH$_2$CH$_3$); 3.99-4.14 (2H, m, OCH$_2$CH$_3$); 4.81 (2H, app s, PhCH$_2$O); and 7.22-7.37 (10H, m, arom. H);

$^{13}$C-NMR (75 MHz, CDCl$_3$) δ: 16.48 (d, $^3J_{CP}$=5.7 Hz, OCH$_2$CH$_3$); 16.64 (d, $^3J_{CP}$=6.0 Hz, OCH$_2$CH$_3$); 26.99 (CH$_2$CHP); 42.18 (d, $^1J_{CP}$=138.5 Hz, CHP); 49.42 (d, $^3J_{CP}$=15.3 Hz, NCH$_2$); 61.28 (d, $^2J_{CP}$=7.2 Hz, OCH$_2$CH$_3$); 63.02 (d, $^2J_{CP}$=6.9 Hz, OCH$_2$CH$_3$); 76.64 (OCH$_2$Ph); 127.61 (J$_{CP}$=3.2 Hz, =CH); 128.49 (=CH); 128.71 (=CH); 128.87 (J$_{CP}$=2.6 Hz, =CH); 128.93 (=CH); 129.48 (d, J$_{CP}$=6.6 Hz, =CH); 135.65 (d, J$_{CP}$=6.9 Hz, =C); and 136.72 (=C); and ESI-MS: Calculated for C$_{20}$H$_{27}$NO$_4$P [M−H]$^−$: 376.1676. Found: 376.1677.

Diethyl 3-(benzyloxyamino)-1-p-tolylpropylphosphonate (9b)

(yield: 95%) was characterised as follows:

$^1$H-NMR (300 MHz, CDCl$_3$) δ: 1.06 (3H, m, OCH$_2$CH$_3$); 1.25 (3H, m, OCH$_2$CH$_3$); 2.11-2.24 (1H, m, CH$_2$CHP); 2.25 (3H, s, p-CH$_3$); 2.38-2.87 (1H, m, CH$_2$CHP); 2.89 (1H, m, CH$_2$N); 2.96 (1H, m, CH$_2$N); 3.15 (1H, ddd, J$_{HP}$=22.4 Hz, J$_{HH}$=4.4 Hz and J$_{HH}$=11.4 Hz, CHP); 3.60-3.76 (1H, m, OCH$_2$CH$_3$); 3.78-3.89 (1H, m, OCH$_2$CH$_3$); 3.90-4.05 (2H, m, OCH$_2$CH$_3$); 4.69 (2H, app s, PhCH$_2$O); 7.03-7.13 (2H, m, arom. H); and 7.26-7.31 (7H, m, arom. H);

$^{13}$C-NMR (75 MHz, CDCl$_3$) δ: 16.52 (d, $^3J_{CP}$=5.7 Hz, OCH$_2$CH$_3$); 16.67 (d, $^3J_{CP}$=6.1 Hz, OCH$_2$CH$_3$); 21.34 (p-CH$_3$); 27.60 (d, $^2J_{CP}$=too small for detection, CH$_2$CHP); 41.71 (d, $^1J_{CP}$=139.0 Hz, CHP); 49.75 (d, $^3J_{CP}$=15.8 Hz, NCH$_2$); 61.05 (d, $^2J_{CP}$=7.2 Hz, OCH$_2$CH$_3$); 62.80 (d, $^2J_{CP}$=6.9 Hz, OCH$_2$CH$_3$); 76.60 (OCH$_2$Ph); 128.13 (=CH); 128.64 (d, =CH); 129.31 (=CH); 129.40 (=CH); 129.52 (=CH); 132.65 (d, J$_{CP}$=6.9 Hz, =C); 137.07 (d, J$_{CP}$=3.5 Hz, =C); and 137.76 (=C); and ESI-MS: Calculated for C$_{21}$H$_{31}$NO$_4$P [M+H]$^+$: 392.1991. Found: 392.3.

Diethyl 3-(benzyloxyamino)-1-(4-methoxyphenyl) propylphosphonate (9c)

(yield: 95%) was characterised as follows:

$^1$H-NMR (300 MHz, CDCl$_3$) δ: 1.10 (3H, t, J$_{HH}$=7.0 Hz, OCH$_2$CH$_3$); 1.27 (3H, t, J$_{HH}$=7.0 Hz, OCH$_2$CH$_3$); 2.03-2.19 (1H, m, CH$_2$CHP); 2.29-2.43 (1H, m, CH$_2$CHP); 2.71-2.80 (1H, m, CH$_2$N); 2.87-2.96 (1H, m, CH$_2$N); 3.18 (1H, ddd, J$_{HP}$=22.6 Hz, J$_{HH}$=3.8 Hz and J$_{HH}$=11.1 Hz, CHP); 3.65-3.80 (1H, m, OCH$_2$CH$_3$); 3.78 (OCH$_3$); 3.83-3.93 (1H, m, OCH$_2$CH$_3$); 3.96-4.12 (2H, m, OCH$_2$CH$_3$); 4.69 (2H, app s, PhCH$_2$O); 6.82-6.86 (2H, m, arom. H); and 7.21-7.34 (7H, m, arom. H);

$^{13}$C-NMR (75 MHz, CDCl$_3$) δ: 16.54 (d, $^3J_{CP}$=5.8 Hz, OCH$_2$CH$_3$); 16.67 (d, $^3J_{CP}$=6.3 Hz, OCH$_2$CH$_3$); 27.77 (d, CH$_2$CHP); 41.23 (d, $^1J_{CP}$=139.6 Hz, CHP); 49.77 (d, $^3J_{CP}$=15.8 Hz, NCH$_2$); 55.54 (OCH$_3$); 61.98 (d, $^2J_{CP}$=7.5 Hz, OCH$_2$CH$_3$); 62.77 (d, $^2J_{CP}$=7.2 Hz, OCH$_2$CH$_3$); 76.60 (OCH$_2$Ph); 114.20 (d, $J_{CP}$=0.03 Hz, =CH); 127.74 (d, $J_{CP}$=7.2 Hz, =C); 128.07 (=CH); 128.60 (=CH); 129.26 (d, $J_{CP}$=4.9 Hz, =CH); 131.50 (d, $J_{CP}$=6.9 Hz, =CH); 137.93 (=C); and 158.97 (d, $J_{CP}$=3.2 Hz, =C);

$^{31}$P-NMR (120 MHz, CDCl$_3$) δ=30.20; and

ESI-MS: Calculated for C$_{21}$H$_{31}$NO$_5$P [M+H]$^+$: 408.1940. Found: 408.1932.

Diethyl 3-(benzyloxyamino)-1-(4-chlorophenyl)propylphosphonate (9d)

(yield: 93%) was characterised as follows:

$^1$H-NMR (300 MHz, CDCl$_3$) δ: 1.14 (3H, t, $J_{HH}$=7.0 Hz, OCH$_2$CH$_3$); 1.26 (3H, dt, $J_{HH}$=7.0 Hz, $J_{HP}$=1.76 Hz, OCH$_2$CH$_3$); 2.14-2.30 (1H, m, CH$_2$CHP); 2.42-2.59 (1H, m, CH$_2$CHP); 2.95-3.00 (1H, m, CH$_2$N); 3.01-3.12 (1H, m, CH$_2$N); 3.32 (1H, ddd, $J_{HP}$=22.7 Hz, $J_{HH}$=4.7 Hz and $J_{HH}$=10.3 Hz, CHP); 3.73-3.87 (1H, m, OCH$_2$CH$_3$); 3.89-3.96 (1H, m, OCH$_2$CH$_3$); 3.97-4.12 (2H, m, OCH$_2$CH$_3$); 4.94 (2H, s, PhCH$_2$O); and 7.18-7.38 (9H, m, arom. H);

$^{13}$C-NMR (75 MHz, CDCl$_3$) δ: 16.54 (app t, $^3J_{CP}$=6.3 Hz, OCH$_2$CH$_3$); 25.75 (m, CH$_2$CHP); 41.45 (d, $^1J_{CP}$=138.8 Hz, CHP); 48.67 (d, $^3J_{CP}$=13.5 Hz, NCH$_2$); 62.83 (d, $^2J_{CP}$=7.2 Hz, OCH$_2$CH$_3$); 63.24 (d, $^2J_{CP}$=7.2 Hz, OCH$_2$CH$_3$); 77.44 (OCH$_2$Ph); 128.70-128.92 (m, =CH); 129.13-129.16 (m, =CH); 129.16-129.30 (m, =CH); 129.41 (m, =CH); 130.68-130.77 (m, =CH); 133.76 (=C); 133.89 (=C); and 133.99 (=C); and ESI-MS: Calculated for C$_{20}$H$_{28}$ClNO$_4$P [M+H]$^+$: 412.1445. Found: 412.1312.

Diethyl 3-(benzyloxyamino)-1-(3,4-dichlorophenyl)propylphosphonate (9e)

(yield: 91%) was characterised as follows:

$^1$H-NMR (300 MHz, CDCl$_3$) δ: 1.16 (3H, t, $J_{HH}$=7.0 Hz, OCH$_2$CH$_3$); 1.28 (3H, t, $J_{HH}$=7.0 Hz, OCH$_2$CH$_3$); 1.97-2.13 (1H, m, CH$_2$CHP); 2.28-2.42 (1H, m, CH$_2$CHP); 2.64-2.74 (1H, m, CH$_2$N); 2.85-2.93 (1H, m, CH$_2$N); 3.20 (1H, ddd, $J_{HP}$=22.6 Hz, $J_{HH}$=4.1 Hz and $J_{HH}$=11.1 Hz, CHP); 3.77-3.89 (1H, m, OCH$_2$CH$_3$); 3.91-3.99 (1H, m, OCH$_2$CH$_3$); 3.99-4.13 (2H, m, OCH$_2$CH$_3$); 4.61-4.70 (2H, m, PhCH$_2$O); 7.13-7.17 (1H, m, arom. H); and 7.26-7.40 (7H, m, arom. H);

$^{13}$C-NMR (75 MHz, CDCl$_3$) δ: 16.56 (d, $^3J_{CP}$=7.8 Hz, OCH$_2$CH$_3$); 16.64 (d, $^3J_{CP}$=8.1 Hz, OCH$_2$CH$_3$); 27.73 (d, $^2J_{CP}$=2.9 Hz, CH$_2$CHP); 41.35 (d, $^1J_{CP}$=139.6 Hz, CHP); 49.48 (d, $^3J_{CP}$=15.3 Hz, NCH$_2$); 62.36 (d, $^2J_{CP}$=6.9 Hz, OCH$_2$CH$_3$); 62.88 (d, $^2J_{CP}$=6.9 Hz, OCH$_2$CH$_3$); 77.88 (OCH$_2$Ph); 128.13 (=CH); 128.61 (=CH); 128.63 (=CH); 128.87 (d, $J_{CP}$=6.6 Hz, =CH); 130.65 (d, $J_{CP}$=2.6 Hz, =CH); 131.42 (d, $J_{CP}$=6.9 Hz, =CH); 131.53 (=C); 132.74 (d, $J_{CP}$=2.9 Hz, =C); 136.73 (d, $J_{CP}$=6.9 Hz, =C); and 137.88 (=C); and ESI-MS: Calculated for C$_{20}$H$_{27}$Cl$_2$NO$_4$P [M+H]$^+$: 446.1055. Found: 446.1060.

General Method for Synthesis of Intermediates 10c,e

In a three-neck flask containing a solution of formic acid (0.61 mmol, 30 μl) in 0.6 mL CH$_2$Cl$_2$ was added 1,1'-carbonyl-diimidazole (0.64 mmol, 0.10 g). After 20 minutes benzyloxyamines 9c,e (0.61 mmol) obtained in the previous step were dissolved in 1 mL CH$_2$Cl$_2$ and were transferred to the three-neck flask. After 5 hours the mixture was partitioned between water (70 mL) and CH$_2$Cl$_2$ (70 mL). The water layer was extracted twice with CH$_2$Cl$_2$ (70 mL). The combined organic layers were dried with MgSO$_4$ and evaporated in vacuo and the residue was purified by flash chromatography (n-pentane/acetone mixture in a 6:4 volume ratio) to provide intermediates 10c,e in the form of transparent oils.

Diethyl 3-(N-(benzyloxy)formamido)-1-(4-methoxyphenyl)propylphosphonate (10c)

(yield: 79%) was characterised as follows:

$^1$H-NMR (300 MHz, CDCl$_3$) δ: 1.09 (3H, t, $J_{HH}$=7.0 Hz, OCH$_2$CH$_3$); 1.26 (3H, t, $J_{HH}$=7.0 Hz, OCH$_2$CH$_3$); 2.17 (1H, m, CH$_2$CHP); 2.41-2.49 (1H, m, CH$_2$CHP); 3.00 (1H, ddd, $J_{HP}$=22.9 Hz, $J_{HH}$=3.8 Hz and $J_{HH}$=11.4 Hz, CHP); 3.40 (1H, m, CH$_2$N); 3.55 (1H, m, CH$_2$N); 3.62-3.80 (1H, m, OCH$_2$CH$_3$); 3.82-3.96 (1H, m, OCH$_2$CH$_3$); 3.94 (OCH$_3$); 3.97-4.11 (2H, m, OCH$_2$CH$_3$); 4.74 and 4.94 (2H, 2×br s, PhCH$_2$O); 6.84-7.36 (9H, m, arom. H); and 8.16 (1H, br s, HC=O);

$^{13}$C-NMR (75 MHz, CDCl$_3$) δ: 16.50 (d, $^3J_{CP}$=5.0 Hz, OCH$_2$CH$_3$); 16.63 (d, $^3J_{CP}$=5.8 Hz, OCH$_2$CH$_3$); 27.39 (m, CH$_2$CHP); =/–40 (d, $^1J_{CP}$=/–140 Hz, CHP); 42.60 (m, NCH$_2$); 55.47 (OCH$_3$); 62.14 (d, $^2J_{CP}$=7.2 Hz, OCH$_2$CH$_3$); 63.94 (d, $^2J_{CP}$=7.2 Hz, OCH$_2$CH$_3$); 77.45 (OCH$_2$Ph); 114.36 (arom. C); 126.80 (arom. C); 128.93 (arom. C); 129.32 (arom. C); 129.66 (arom. C); 130.50 (arom. C); 158.50 (arom. C); 159.21 (arom. C); and 163.27 (m, HC=O); and ESI-MS: Calculated for C$_{22}$H$_{31}$NO$_6$P [M+H]$^+$: 436.1889. Found: 436.1888.

Diethyl 3-(N-(benzyloxy)formamido)-1-(3,4-dichlorophenyl)propylphosphonate (10e)

(yield: 85%) was characterised as follows:

$^1$H-NMR (300 MHz, CDCl$_3$) δ: 1.14 (3H, t, $J_{HH}$=7.0 Hz, OCH$_2$CH$_3$); 1.27 (3H, t, $J_{HH}$=7.0 Hz, OCH$_2$CH$_3$); 2.07-2.21 (1H, m, CH$_2$CHP); 2.37-2.51 (1H, m, CH$_2$CHP); 3.00 (1H, ddd, $J_{HP}$=23.0 Hz, $J_{HH}$=4.1 Hz and $J_{HH}$=11.4 Hz, CHP); 3.23-3.38 (1H, m, CH$_2$N); 3.44-3.46 (1H, m, CH$_2$N); 3.78-3.88 (1H, m, OCH$_2$CH$_3$); 3.89-3.99 (1H, m, OCH$_2$CH$_3$); 3.99-4.11 (2H, m, OCH$_2$CH$_3$); 4.75 and 4.91 (2H, 2×br s, PhCH$_2$O); 7.12-7.40 (8H, m, arom. H); and 8.16 (1H, br s, HC=O);

$^{13}$C-NMR (75 MHz, CDCl$_3$) δ: 16.50 (d, $^3J_{CP}$=6.1 Hz, OCH$_2$CH$_3$); 16.61 (d, $^3J_{CP}$=6.1 Hz, OCH$_2$CH$_3$); 27.34 (m, CH$_2$CHP); 41.46 (d, $^1J_{CP}$=138.48 Hz, CHP); 42.50 (m, NCH$_2$); 62.59 (d, $^2J_{CP}$=7.2 Hz, OCH$_2$CH$_3$); 63.09 (d, $^2J_{CP}$=6.9 Hz, OCH$_2$CH$_3$); 78.29 (OCH$_2$Ph); 128.86 (arom. C); 128.95 (arom. C); 129.94 (arom. C); 129.69 (arom. C); 130.81 (arom. C); 131.24 (arom. C); 131.92 (arom. C); 132.93 (arom. C); 134.27 (arom. C); 135.87 (arom. C); and 163.32 (m, HC=O); and ESI-MS: Calculated for C$_{21}$H$_{27}$Cl$_2$NO$_5$P [M+H]$^+$: 474.1004. Found: 474.1000.

General Method for the Synthesis of Intermediates 11a-e

A solution of benzyloxyamines 9a-e (2.43 mmol) obtained in the previous step in CH$_2$Cl$_2$ (12 mL) containing (Et)$_3$N (1.03 mL, 7.23 mmol) was cooled in an ice bath, followed by addition of acetylchloride (0.21 mL, 2.91 mmol). After 1.5-2 hours the reaction mixture was diluted with CH$_2$Cl$_2$ (100 mL) and washed with water (100 mL). After drying of the organic layer with MgSO$_4$, the solvent was removed in vacuo and the crude reaction mixture was submitted to chromatography (CH$_2$Cl$_2$/MeOH mixture in a 95:5 volume ratio, or n-hexane/ethyl acetate in a volume ratio progressively ranging from 6:4 to 1:1). Intermediate compounds 11a-e were thus obtained in the form of transparent oils.

Diethyl 3-(N-(benzyloxy)acetamido)-1-phenylpropylphosphonate (11a)

(yield: 85%) was characterised as follows:

$^1$H-NMR (300 MHz, CDCl$_3$) δ: 1.05 (3H, t, J$_{HH}$=7.6 Hz, OCH$_2$CH$_3$); 1.25 (3H, t, J$_{HH}$=7.0 Hz, OCH$_2$CH$_3$); ); 2.00 (3H, s, CH$_3$C=O); 2.18-2.34 (1H, m, CH$_2$CHP); 2.37-2.51 (1H, m, CH$_2$CHP); 3.06 (1H, ddd, J$_{HP}$=23.0 Hz, J$_{HH}$=4.1 Hz and J$_{HH}$=11.4 Hz, CHP); 3.39-3.49 (1H, m, CH$_2$N); 3.54-3.61 (1H, m, CH$_2$N); 3.63-3.74 (1H, m, OCH$_2$CH$_3$); 3.79-3.95 (1H, m, OCH$_2$CH$_3$); 3.95-4.07 (2H, m, OCH$_2$CH$_3$); 4.67 (2H, m, PhCH$_2$O); and 7.22-7.36 (10H, m, arom. H);

$^{13}$C-NMR (75 MHz, CDCl$_3$) δ: 16.43 (d, $^3$J$_{CP}$=5.8 Hz, OCH$_2$CH$_3$); 16.60 (d, $^3$J$_{CP}$=6.0 Hz, OCH$_2$CH$_3$); 20.67 (CH$_3$C=O); 27.07 (CH$_2$CHP); 42.34 (d, $^1$J$_{CP}$=137.9 Hz, CHP); 44.01 (br m, NCH$_2$); 62.24 (d, $^2$J$_{CP}$=7.2 Hz, OCH$_2$CH$_3$); 62.98 (d, $^2$J$_{CP}$=7.2 Hz, OCH$_2$CH$_3$); 76.54 (OCH$_2$Ph); 127.62 (d, J$_{CP}$=3.2 Hz, =CH); 128.82 (d, J$_{CP}$=2.9 Hz, =CH); 128.89 (=CH); 129.16 (=CH); 129.41 (=CH); 129.52 (d, J$_{CP}$=6.6 Hz, =CH); 134.49 (=C); 135.27 (d, J$_{CP}$=7.2 Hz, =C); and 172.56 (CH$_3$C=O); and ESI-MS: Calculated for C$_{22}$H$_{31}$NO$_5$P [M+H]$^+$: 420.1940. Found: 420.1931.

Diethyl 3-(N-(benzyloxy)acetamido)-1-p-tolylpropylphosphonate (11b)

(yield: 60%) was characterised as follows:

$^1$H-NMR (300 MHz, CDCl$_3$) δ: 1.09 (3H, t, J$_{HH}$=7.0 Hz, OCH$_2$CH$_3$); 1.25 (3H, t, J$_{HH}$=7.0 Hz, OCH$_2$CH$_3$); 2.02 (3H, s, CH$_3$C=O); 2.21-2.30 (1H, m, CH$_2$CHP); 2.32 (p-CH$_3$); 2.39-2.46 (1H, m, CH$_2$CHP); 3.02 (1H, ddd, J$_{HP}$=22.9 Hz, J$_{HH}$=4.1 Hz and J$_{HH}$=11.7 Hz, CHP); 3.39-3.49 (1H, m, CH$_2$N); 3.60 (1H, m, CH$_2$N); 3.65-3.77 (1H, m, OCH$_2$CH$_3$); 3.81-3.92 (1H, m, OCH$_2$CH$_3$); 3.94-4.07 (2H, m, OCH$_2$CH$_3$); 4.69 (2H, m, PhCH$_2$O); and 7.11-7.38 (9H, m, arom. H);

$^{13}$C-NMR (75 MHz, CDCl$_3$) δ: 16.47 (d, $^3$J$_{CP}$=5.7 Hz, OCH$_2$CH$_3$); 16.62 (d, $^3$J$_{CP}$=6.0 Hz, OCH$_2$CH$_3$); 20.71 (CH$_3$C=O); 21.32 (p-CH$_3$); 27.05 (CH$_2$CHP); 41.86 (d, $^1$J$_{CP}$=138.5 Hz, CHP); 43.80 (br m, NCH$_2$); 62.13 (d, $^2$J$_{CP}$=7.2 Hz, OCH$_2$CH$_3$); 62.82 (d, $^2$J$_{CP}$=6.9 Hz, OCH$_2$CH$_3$); 76.49 (OCH$_2$Ph); 128.86 (=CH); 129.13 (=CH); 129.28 (=CH); 129.39 (d, J$_{CP}$=3.8 Hz, =CH); 129.52 (d, J$_{CP}$=2.6 Hz, =CH); 132.081 (d, J$_{CP}$=7.2 Hz, =C); 134.52 (=C); 137.17 (d, J$_{CP}$=3.4 Hz, =C); and 172.50 (CH$_3$C=O); and ESI-MS: Calculated for C$_{23}$H$_{33}$NO$_5$P [M+H]$^+$: 434.2096. Found: 434.3.

Diethyl 3-(N-(benzyloxy)acetamido)-1-(4-methoxyphenyl)propylphosphonate (11c)

(yield: 93%) was characterised as follows:

$^1$H-NMR (300 MHz, CDCl$_3$) δ: 1.09 (3H, t, J$_{HH}$=7.0 Hz, OCH$_2$CH$_3$); 1.26 (3H, t, J$_{HH}$=7.0 Hz, OCH$_2$CH$_3$); 2.02 (3H, s, CH$_3$C=O); 2.14-2.30 (1H, m, CH$_2$CHP); 2.36-2.50 (1H, m, CH$_2$CHP); 3.01 (1H, ddd, J$_{HP}$=22.9 Hz, J$_{HH}$=3.5 Hz and J$_{HH}$=11.4 Hz, CHP); 3.40-3.49 (1H, m, CH$_2$N); 3.56-3.63 (1H, m, CH$_2$N); 3.65-3.76 (1H, m, OCH$_2$CH$_3$); 3.80 (OCH$_3$); 3.83-3.92 (1H, m, OCH$_2$CH$_3$); 3.94-4.08 (2H, m, OCH$_2$CH$_3$); 4.7 (2H, m, PhCH$_2$O); and 6.84-7.38 (9H, m, arom. H);

$^{13}$C-NMR (75 MHz, CDCl$_3$) δ: 16.52 (d, $^3$J$_{CP}$=5.5 Hz, OCH$_2$CH$_3$); 16.64 (d, $^3$J$_{CP}$=5.8 Hz, OCH$_2$CH$_3$); 20.65 (CH$_3$C=O); 27.19 (CH$_2$CHP); 41.44 (d, $^1$J$_{CP}$=138.8 Hz, CHP); 44.00 (br m, NCH$_2$); 55.46 (OCH$_3$); 62.11 (d, $^2$J$_{CP}$=7.2 Hz, OCH$_2$CH$_3$); 62.85 (d, $^2$J$_{CP}$=6.9 Hz, OCH$_2$CH$_3$); 76.54 (OCH$_2$Ph); 114.24 (=CH); 127.13 (=C); 129.89 (=CH); 129.16 (=CH); 129.40 (=CH); 130.509 (d, =CH); 134.90 (=C); 159.07 (=C); and 172.00 (CH$_3$C=O);

$^{31}$P-NMR (120 MHz, CDCl$_3$) δ=29.48; and

ESI-MS: Calculated for C$_{23}$H$_{33}$NO$_6$P [M+H]$^+$: 450.2046. Found: 450.2043.

Diethyl 3-(N-(benzyloxy)acetamido)-1-(4-chlorophenyl)propylphosphonate (11d)

(yield: 95%) was characterised as follows:

$^1$H-NMR (300 MHz, CDCl$_3$) δ: 1.08 (3H, t, J$_{HH}$=7.0 Hz, OCH$_2$CH$_3$); 1.23 (3H, t, J$_{HH}$=7.0 Hz, OCH$_2$CH$_3$); ); 1.99 (3H, s, CH$_3$C=O); 2.09-2.27 (1H, m, CH$_2$CHP); 2.35-2.49 (1H, m, CH$_2$CHP); 3.01 (1H, ddd, J$_{HP}$=22.9 Hz, J$_{HH}$=3.8 Hz and J$_{HH}$=11.4 Hz, CHP); 3.37-3.46 (1H, m, CH$_2$N); 3.49-3.58 (1H, m, CH$_2$N); 3.66-3.79 (1H, m, OCH$_2$CH$_3$); 3.81-3.91 (1H, m, OCH$_2$CH$_3$); 3.93-4.06 (2H, m, OCH$_2$CH$_3$); 4.67 (2H, m, PhCH$_2$O); and 7.19-7.36 (9H, m, arom. H);

$^{13}$C-NMR (75 MHz, CDCl$_3$) δ: 16.48 (d, $^3$J$_{CP}$=5.8 Hz, OCH$_2$CH$_3$); 16.61 (d, $^3$J$_{CP}$=5.8 Hz, OCH$_2$CH$_3$); 20.65 (CH$_3$C=O); 27.02 (d, $^2$J$_{CP}$=2.3 Hz, CH$_2$CHP); 41.74 (d, $^1$J$_{CP}$=139.1 Hz, CHP); 43.80 (br d, NCH$_2$); 62.35 (d, $^2$J$_{CP}$=7.5 Hz, OCH$_2$CH$_3$); 62.96 (d, $^2$J$_{CP}$=7.2 Hz, OCH$_2$CH$_3$); 76.66 (OCH$_2$Ph); 128.92 (=CH); 128.97 (=CH); 129.23 (=CH); 129.39 (=CH); 130.83 (=CH); 133.44 (d, =C); 134.03 (d, =C); 134.43 (=C); and 172.53 (CH$_3$C=O); and ESI-MS: Calculated for C$_{22}$H$_{30}$ClNO$_5$P [M+H]$^+$: 454.1550. Found: 454.1552.

Diethyl 3-(N-(benzyloxy)acetamido)-1-(3,4-dichlorophenyl)propylphosphonate (11e)

(yield: 85%) was characterised as follows:

$^1$H-NMR (300 MHz, CDCl$_3$) δ: 1.14 (3H, t, J$_{HH}$=7.0 Hz, OCH$_2$CH$_3$); 1.26 (3H, t, J$_{HH}$=7.0 Hz, OCH$_2$CH$_3$); ); 2.02 (3H, s, CH$_3$C=O); 2.08-2.26 (1H, m, CH$_2$CHP); 2.35-2.49 (1H, m, CH$_2$CHP); 3.00 (1H, ddd, J$_{HP}$=23.0 Hz, J$_{HH}$=3.8 Hz and J$_{HH}$=11.1 Hz, CHP); 3.27-3.59 (2H, m, CH$_2$N); 3.75-3.86 (1H, m, OCH$_2$CH$_3$); 3.86-3.97 (1H, m, OCH$_2$CH$_3$); 3.97-4.11 (2H, m, OCH$_2$CH$_3$); 4.71 (2H, m, PhCH$_2$O); and 7.12-7.43 (8H, m, arom. H);

$^{13}$C-NMR (75 MHz, CDCl$_3$) δ: 16.48 (app t, $^3$J$_{CP}$=6.6 Hz, OCH$_2$CH$_3$); 20.62 (CH$_3$C=O); 27.01 (CH$_2$CHP); 41.66 (d, $^1$J$_{CP}$=139.1 Hz, CHP); 44.07 (br m, NCH$_2$); 62.52 (d, $^2$J$_{CP}$=7.2 Hz, OCH$_2$CH$_3$); 62.98 (d, $^2$J$_{CP}$=6.9 Hz, OCH$_2$CH$_3$); 76.80 (OCH$_2$Ph); 128.91 (=CH); 129.33 (=CH); 129.60 (=CH); 130.40 (=CH); 131.67 (=CH); 131.30 (=CH); 131.69 (d, =C); 132.78 (d, =C); 134.39 (=C); 136.10 (d, =C); and 172.54 (CH$_3$C=O); and ESI-MS: Calculated for C$_{22}$H$_{29}$Cl$_2$NO$_5$P [M+H]$^+$: 488.1161. Found: 488.1160.

General Method for the Benzyl Deprotection of Intermediates 10 and 11

A solution of intermediate compounds 10 or 11 (0.9 mmol) in methanol (8 mL) was hydrogenated at atmospheric pressure in the presence of 10% by weight on activated carbon (40 mg). After stirring for 5 hours, the reaction mixture was filtered over a Celite pad. The solvent was removed under vacuo and the crude mixture was purified by column chromatography ($CH_2Cl_2$/MeOH mixture in a 95:5 volume ratio).

Diethyl 3-(N-hydroxyformamido)-1-(4-methoxyphenyl)propylphosphonate (12c)

(yield: 25%) was characterised as follows:

$^1$H-NMR (300 MHz, $CDCl_3$) δ: 1.05-1.10 (3H, m, $OCH_2CH_3$); 1.17-1.23 (3H, m, $OCH_2CH_3$); 2.16 (1H, m, $CH_2CHP$); 2.53 (1H, m, $CH_2CHP$); 2.99-3.08 (1H, m, CHP); 3.24-3.30 (1H, m, $CH_2N$); 3.40-3.62 (1H, m, $CH_2N$); 3.66-3.71 (1H, m, $OCH_2CH_3$); 3.73 ($OCH_3$); 3.81-3.86 (1H, m, $OCH_2CH_3$); 3.91-3.99 (2H, m, $OCH_2CH_3$); 6.81-6.85 (2H, m, $H_m$); 7.17-7.19 (2H, m, $H_o$); 7.52 (1H, br s, HC=O); and 8.31 (1H, s, NOH);

$^{13}$C-NMR (75 MHz, $CDCl_3$) δ: 16.05 (d, $^3J_{CP}$=5.9 Hz, $OCH_2CH_3$); 16.15 (d, $^3J_{CP}$=5.9 Hz, $OCH_2CH_3$); 26.40 ($CH_2CHP$, major); 27.02 ($CH_2CHP$, minor); 39.56 (d, $^1J_{CP}$=139.2 Hz, CHP, major); 40.66 (d, $^1J_{CP}$=137.2 Hz, CHP, minor); 44.56 (d, $^3J_{CP}$=16.6 Hz, $NCH_2$, minor); 47.05 (d, $^3J_{CP}$=16.1 Hz, $NCH_2$, major); 55.03 ($OCH_3$); 62.07 (d, $^2J_{CP}$=6.9 Hz, $OCH_2CH_3$, major); 62.25 (d, $^2J_{CP}$=6.8 Hz, $OCH_2CH_3$, minor); 62.69 (d, $^2J_{CP}$=6.3 Hz, $OCH_2CH_3$, major); 62.83 (d, $^2J_{CP}$=5.9 Hz, $OCH_2CH_3$, minor); 113.89 (=$C_mH$, minor); 114.11 (=$C_mH$, major); 125.94 (d, $^2J_{CP}$=7.3 Hz, =$C_i$, major); 126.75 (d, $^2J_{CP}$=6.4 Hz, =$C_i$, minor); 130.05 (=$C_o$H); 158.77 (=$C_p$, minor); 158.90 (=$C_p$, major); 156.84 (C=O, major); 162.56 (C=O, minor); and ESI-MS: Calculated for $C_{15}H_{25}NO_6P$ [M+H]$^+$: 346.1420. Found: 346.1427.

Diethyl 3-(N-hydroxyformamido)-1-(3,4-dichlorophenyl)propylphosphonate (12e)

(Yield: 57%) was characterised as follows:

$^1$H-NMR (300 MHz, $CDCl_3$) δ: 1.09-1.24 (6H, m, $OCH_2CH_3$); 2.11 (1H, m, $CH_2CHP$); 2.46 (1H, m, $CH_2CHP$); 3.01-3.17 (1H, m, CHP); 3.22-3.35 (1H, m, $CH_2N$); 3.45-3.56 (1H, m, $CH_2N$); 3.77-4.04 (4H, m, $OCH_2CH_3$); 7.08 and 7.11 (1H, arom. H); 7.32-7.37 (2H, m, arom. H); and 7.55 (1H, br s, HC=O); 8.24 (1H, s, NOH);

$^{13}$C-NMR (75 MHz, $CDCl_3$) δ: 16.48 (app t, $^3J_{CP}$=5.8 Hz, $OCH_2CH_3$); 26.90 ($CH_2CHP$, major); 27.08 ($CH_2CHP$, minor); 40.09 (d, $^1J_{CP}$=139.3 Hz, CHP, major); 40.96 (d, $^1J_{CP}$=139.3 Hz, CHP, minor); 44.60 (d, $^3J_{CP}$=15.8 Hz, $NCH_2$, minor); 47.45 (d, $^3J_{CP}$=15.0 Hz, $NCH_2$, major); 62.84 (d, $^2J_{CP}$=6.9 Hz, $OCH_2CH_3$, major); 63.01 (d, $^2J_{CP}$=7.2 Hz, $OCH_2CH_3$, minor); 63.24 (d, $^2J_{CP}$=6.9 Hz, $OCH_2CH_3$, major); 63.32 (d, $^2J_{CP}$=6.1 Hz, $OCH_2CH_3$, minor); 128.81 (d, $J_{CP}$=6.3 Hz, =CH, major); 128.95 (d, $J_{CP}$=6.9 Hz, =CH, minor); 130.69 (=CH, minor); 130.91 (=CH, major); 131.14 (d, $J_{CP}$=6.9 Hz, =CH, major); 131.24 (d, $J_{CP}$=9.2 Hz, =CH, minor); 131.74 (d, $J_{CP}$=3.8, =C, minor); 131.98 (d, $J_{CP}$=3.8, =C, major); 132.70 (d, $J_{CP}$=2.6, =C, minor); 133.01 (d, $J_{CP}$=2.6, =C, major); 135.60 (d, $J_{CP}$=7.2, =C, major); 136.00 (d, $J_{CP}$=7.5, =C, minor); 157.37 (C=O, major); and 163.03 (C=O, minor); and ESI-MS: Calculated for $C_{14}H_{21}Cl_2NO_5P$ [M+H]$^+$: 384.0535. Found: 384.0530.

Diethyl 3-(N-hydroxyacetamido)-1-phenylpropylphosphonate (13a)

(yield: 62%) was characterised as follows:

$^1$H-NMR (300 MHz, $CDCl_3$) δ: 1.01 (3H, m, $OCH_2CH_3$); 1.19 (3H, m, $OCH_2CH_3$); 1.98 (3H, s, $CH_3C$=O); 2.20 (1H, m, $CH_2CHP$); 2.36 (1H, m, $CH_2CHP$); 3.04 (1H, m, CHP); 3.38 (1H, m, $CH_2N$); 3.62 (1H, m, $CH_2N$); 3.64 (1H, m, $OCH_2CH_3$); 3.78 (1H, m, $OCH_2CH_3$); 3.92 (2H, m, $OCH_2CH_3$); 7.23 (5H, m, arom. H); and 9.70 (1H, br s, NOH);

$^{13}$C-NMR (75 MHz, $CDCl_3$) δ: 16.46 ($OCH_2CH_3$); 20.65 ($CH_3C$=O); 27.34 ($CH_2CHP$); 42.11 (d, $^1J_{CP}$=137.7 Hz, CHP); 46.34 (d, $^3J_{CP}$=17.0 Hz, $NCH_2$); 62.57 ($OCH_2CH_3$); 63.21 ($OCH_2CH_3$); 127.66 (=CH); 128.80 (=CH); 129.38 (=CH); 135.43 (=C); and 172.90 (C=O); and ESI-MS): Calculated for $C_{15}H_{25}NO_5P$ [M+H]$^+$: 330.1470. Found: 330.1475.

Diethyl 3-(N-hydroxyacetamido)-1-p-tolylpropylphosphonate (13b)

(yield: 20%) was characterised as follows:

$^1$H-NMR (300 MHz, $CDCl_3$) δ: 1.03-1.25 (6H, m, $OCH_2CH_3$); 2.10 (3H, s, $CH_3C$=O); 2.25 (3H, s, p-$CH_3$); 2.20 (1H, m, $CH_2CHP$); 2.49 (1H, m, $CH_2CHP$); 2.95-3.07 (1H, m, CHP); 3.30 (1H, m, $CH_2N$); 3.47 (1H, m, $CH_2N$); 3.70-4.02 (4H, m, $OCH_2CH_3$); and 7.04-7.12 (4H, m, arom. H);

$^{13}$C-NMR (75 MHz, $CDCl_3$) δ: 16.50 ($OCH_2CH_3$); 20.66 ($CH_3C$=O); 21.31 (p-$CH_3$); 28.45 ($CH_2CHP$); 41.68 (d, $^1J_{CP}$=135.9 Hz, CHP); 46.74 (d, $^3J_{CP}$=11.2 Hz, $NCH_2$); 63.02 (d, $^2J_{CP}$=6.6 Hz, $OCH_2CH_3$); 63.31 (d, $^2J_{CP}$=7.8 Hz, $OCH_2CH_3$); 129.14 (=CH); 129.68 (=CH); 133.69 (=C); 137.34 (=C); and 172.90 (C=O); and ESI-MS: Calculated for $C_{16}H_{27}NO_5P$ [M+H]$^+$: 344.1627. Found: 344.2.

Diethyl 3-(N-hydroxyacetamido)-1-(4-methoxyphenyl)propylphosphonate (13c)

(yield: 82%) was characterised as follows:

$^1$H-NMR (300 MHz, $CDCl_3$) δ: 1.13 (3H, t, $J_{HH}$=7.0 Hz, $OCH_2CH_3$); 1.23 (3H, t, $J_{HH}$=6.7 Hz, $OCH_2CH_3$); 2.09 (3H, s, $CH_3C$=O); 2.17 (1H, m, $CH_2CHP$); 2.44 (1H, m, $CH_2CHP$); 3.04 (1H, app ddd, CHP); 3.36 (1H, m, $CH_2N$); 3.53 (1H, m, $CH_2N$); 3.77 (3H, s, $OCH_3$); 3.70-4.01 (4H, m, $OCH_2CH_3$); 6.82 (2H, d, $J_{CP}$=7.9 Hz, arom. H); and 7.19 (2H, d, $J_{CP}$=7.9 Hz, arom. H);

$^{13}$C-NMR (75 MHz, $CDCl_3$) δ: 16.52 ($OCH_2CH_3$); 20.70 ($CH_3C$=O); 27.93 ($CH_2CHP$); 41.22 (d, $^1J_{CP}$=138.2 Hz, CHP); 46.49 (d, $^3J_{CP}$=14.1 Hz, $NCH_2$); 62.64 ($OCH_2CH_3$); 63.23 ($OCH_2CH_3$); 114.27 (=CH); 127.66 (=C); 130.34 (d, $J_{CP}$=6.1 Hz, =CH); 159.08 (=C); and 172.45 (C=O); and ESI-MS: Calculated for $C_{16}H_{27}NO_6P$ [M+H]$^+$: 360.1576. Found: 360.1573.

Diethyl 3-(N-hydroxyacetamido)-1-(4-chlorophenyl)propylphosphonate 13d (yield: 70%) was characterised as follows:

$^1$H-NMR (300 MHz, CDCl$_3$) δ: 0.94 (3H, t, J$_{HH}$=7.0 Hz, OCH$_2$CH$_3$); 1.07 (3H, t, J$_{HH}$=7.0 Hz, OCH$_2$CH$_3$); 1.83 (3H, s, CH$_3$C=O); 2.00 (1H, m, CH$_2$CHP); 2.22 (1H, m, CH$_2$CHP); 2.88-2.98 (1H, app dd, CHP); 3.23 (1H, m, CH$_2$N); 3.38 (1H, m, CH$_2$N); 3.55-3.64 (1H, m, OCH$_2$CH$_3$); 3.67-3.75 (1H, m, OCH$_2$CH$_3$); 3.77-3.84 (2H, m, OCH$_2$CH$_3$); 7.09 (4H, m, arom. H); and 9.57 (1H, br s, NOH);

$^{13}$C-NMR (75 MHz, CDCl$_3$) δ: 16.29 (d, $^3$J$_{CP}$=5.8 Hz, OCH$_2$CH$_3$); 16.40 (d, $^3$J$_{CP}$=6.0 Hz, OCH$_2$CH$_3$); 20.35 (CH$_3$C=O); 26.98 (CH$_2$CHP); 41.27 (d, $^1$J$_{CP}$=138.8 Hz, CHP); 45.99 (d, $^3$J$_{CP}$=17.3 Hz, NCH$_2$); 62.55 (d, $^2$J$_{CP}$=7.5 Hz, OCH$_2$CH$_3$); 63.04 (d, $^2$J$_{CP}$=7.2 Hz, OCH$_2$CH$_3$); 128.75 (=CH); 130.68 (d, J$_{CP}$=6.6 Hz, =CH); 133.26 (d, J$_{CP}$=3.8 Hz, =C); 133.88 (d, J$_{CP}$=7.5 Hz, =C); and 172.01 (C=O); and ESI-MS: Calculated for C$_{15}$H$_{24}$ClNO$_5$P [M+H]$^+$: 364.1081. Found: 364.1080.

Diethyl 3-(N-hydroxyacetamido)-1-(3,4-dichlorophenyl)propylphosphonate (13e)

(yield: 62%) was characterised as follows:

$^1$H-NMR (300 MHz, CDCl$_3$) δ: 1.23 (6H, m, OCH$_2$CH$_3$); 1.87 (1H, m, CH$_2$CHP); 2.11 (3H, s, CH$_3$C=O); 2.49 (1H, m, CH$_2$CHP); 3.07 (1H, m, CHP); 3.40 (1H, m, CH$_2$N); 3.59 (1H, m, CH$_2$N); 3.98 (4H, m, OCH$_2$CH$_3$); 7.14 (1H, arom. H); 7.38 (2H, m, arom. H); and 9.45 (1H, br s, NOH);

$^{13}$C-NMR (75 MHz, CDCl$_3$) δ: 16.53 (OCH$_2$CH$_3$); 20.80 (CH$_3$C=O); 26.91 (CH$_2$CHP); 41.37 (d, $^1$J$_{CP}$=139.4 Hz, CHP); 46.34 (NCH$_2$); 63.17 (OCH$_2$CH$_3$); 63.47 (OCH$_2$CH$_3$); 128.78 (=CH); 130.71 (=CH); 131.26 (=CH); 131.81 (=C); 132.816 (=C); 136.87 (=C); and 172.73 (C=O); and ESI-MS: Calculated for C$_{15}$H$_{22}$Cl$_2$NO$_5$P [M+H]$^+$: 398.0691. Found: 398.0695.

General Method for the Phosphonate Deprotection

Esters 12 or 13 (0.84 mmol) obtained in the previous steps were dissolved in CH$_2$Cl$_2$ (10 mL) and treated drop-wise with TMSBr (3.36 mmol, 0.50 g) under nitrogen atmosphere. The reaction mixture was stirred for 2 hours at room temperature. After completion of the reaction the volatile compounds were removed in vacuo to give the corresponding phosphonic acids in almost quantitative yield. All final compounds were purified using a preparative HPLC system on a C18 column (5 μm; Phenomenex; Luna; 250×21.2 mm) with a linear gradient of acetonitrile in 5 mM NH$_4$OAc solution over 20 minutes at a flow rate of 17.5 mL/minute. The purity of all target compounds was assessed by analytical HPLC (5 μm; Phenomenex; C18(2); 250×4.6 mm) using the same gradient at a flow rate of 1 mL/minute. All final compounds were obtained as hygroscopic powders after lyophilisation, and characterised as follows.

3-(N-hydroxyformamido)-1-(4-methoxyphenyl)propylphosphonic acid (1c)

$^1$H NMR (300 MHz; D$_2$O) δ: 1.97-2.12 (1H, m, β-CH); 2.24-2.38 (1H, m, β-CH); 2.74 (1H, ddd, J$_{HP}$=21.9 Hz, J$_{HH}$=3.2 Hz and J$_{HH}$=15.8 Hz, α-CH); 3.13-3.47 (2H, m, γ-CH$_2$); 3.71 (3H, s, OCH$_3$); 6.83-6.87 (2H, m, arom. H); 7.12-7.15 (2H, m, arom. H); 7.38 and 8.08 (1H, 2×s, HC=O);

$^{13}$C NMR (75 MHz; D$_2$O) δ: 26.59 (s, β-CH$_2$); 42.37 (d, α-CH, $^1$J$_{CP}$=131.3 Hz); 48.87 (d, γ-CH$_2$, $^3$J$_{CP}$=17.3 Hz); 55.55 (s, OCH$_3$); 114.28 (d, J$_{CP}$=2.3 Hz, =CH); 130.33 (d, J$_{CP}$=6.1 Hz, =CH); 130.53 (d, J$_{CP}$=7.2 Hz, =C); 157.74 (d, J$_{CP}$=2.9 Hz, =C); 159.74 and 163.70 (2×s, C=O);

$^{31}$P NMR (121 MHz; D$_2$O) δ: 23.18 and 23.47 (major and minor isomer respectively); and ESI-MS: Calculated for C$_{11}$H$_{15}$NO$_6$P [M−H]$^-$: 288.0636. Found: 288.0630.

3-(N-hydroxyformamido)-1-(3,4-dichlorophenyl)propylphosphonic acid (1e)

$^1$H NMR (300 MHz; D$_2$O) δ: 1.93-2.15 (1H, m, β-CH); 2.24-2.38 (1H, m, β-CH); 2.73-2.87 (1H, m, α-CH); 3.17-3.47 (2H, m, γ-CH$_2$); 7.07-7.12 (1H, m, arom. H); 7.33-7.39 (2H, m, arom. H); 7.44 and 8.07 (1H, 2×s, HC=O);

$^{13}$C NMR (75 MHz; D$_2$O) δ: 26.49 (s, β-CH$_2$); 42.82 (d, α-CH, $^1$J$_{CP}$=129.6 Hz); 48.86 (d, γ-CH$_2$, $^3$J$_{CP}$=17.0 Hz); 128.92 (d, J$_{CP}$=5.8 Hz, =CH); 130.04 (d, J$_{CP}$=3.8 Hz, =C); 130.55 (d, J$_{CP}$=2.6 Hz, =CH); 130.73 (d, J$_{CP}$=6.0 Hz, =CH); 131.88 (d, J$_{CP}$=3.2 Hz, =C); 138.80 (d, J$_{CP}$=7.2 Hz, =C); 159.70 and 163.76 (2×s, C=O);

$^{31}$P NMR (121 MHz; D$_2$O) δ: 21.46 and 21.78 (major and minor isomer respectively); and ESI-MS): Calculated for C$_{10}$H$_{11}$Cl$_2$NO$_5$P [M−H]$^-$: 325.9751. Found: 325.9745.

3-(N-hydroxyacetamido)-1-phenylpropylphosphonic acid (2a)

$^1$H NMR (300 MHz; D$_2$O) δ: 1.57 and 1.90 (3H, 2×s, CH$_3$); 2.04-2.14 (1H, m, β-CH); 2.19-2.27 (1H, m, β-CH); 2.70-2.87 (1H, m, α-CH); 3.21-3.30 (1H, m, γ-CH); 3.38-3.53 (1H, m, γ-CH); and 7.16-7.27 (5H, m, arom. H);

$^{13}$C NMR (75 MHz; D$_2$O) δ: 19.35 (s, CH$_3$); 26.99 (s, —CH$_2$); 44.06 (d, α-CH, $^1$J$_{CP}$=129.3 Hz); 46.36 (d, γ-CH$_2$, $^3$J$_{CP}$=17.3 Hz); 126.59 (d, J$_{CP}$=too small for detection, =CH); 128.51 (d, J$_{CP}$=2.3 Hz, =CH); 129.29 (d, J$_{CP}$=5.8 Hz, =CH); 138.93 (m, J$_{CP}$=7.2 Hz, =C); and 173.72 (s, C=O); and ESI-MS: Calculated for C$_{11}$H$_{15}$NO$_5$P [M−H]$^-$: 272.0687. Found: 272.0684.

3-(N-hydroxyacetamido)-1-p-tolylpropylphosphonic acid (2b)

$^1$H NMR (300 MHz; D$_2$O) δ: 1.48 and 1.80 (3H, 2×s, minor and major CH$_3$); 1.84-2.04 (1H, m, β-CH); 2.10 (3H, s, p-CH$_3$); 2.15-2.32 (1H, m, β-CH); 2.58-2.70 (1H, m, α-CH); 3.12-3.20 (1H, m, γ-CH); 3.24-3.42 (1H, m, γ-CH); and 6.99-7.02 (4H, m, arom. H);

$^{13}$C NMR (75 MHz; D$_2$O) δ: 19.25 (s, CH$_3$); 20.15 (s, p-CH$_3$); 26.87 (s, β-CH$_2$); 43.50 (d, α-CH, $^1$J$_{CP}$=129.8 Hz); 46.30 (d, γ-CH$_2$, $^3$J$_{CP}$=17.6 Hz); 128.98 (d, J$_{CP}$=2.3 Hz, =CH); 129.12 (d, J$_{CP}$=6.0 Hz, =CH); 135.50 (d, J$_{CP}$=6.9 Hz, =C); 136.54 (m, J$_{CP}$=3.2 Hz, =C); and 173.60 (s, C=O); and ESI-MS): Calculated for C$_{12}$H$_{17}$NO$_5$P [M−H]$^-$: 286.0843. Found: 286.0839.

3-(N-hydroxyacetamido)-1-(4-methoxyphenyl)propylphosphonic acid (2c)

$^1$H NMR (300 MHz; D$_2$O) δ: 1.55 and 1.88 (3H, 2×s, minor and major CH$_3$); 1.98-2.11 (1H, m, β-CH); 2.15-2.35 (1H, m, β-CH); 2.67-2.84 (1H, m, α-CH); 3.23-3.34 (1H, m, γ-CH); 3.35-3.50 (1H, m, γ-CH); 3.70 (1H, s, OCH$_3$); 6.82-6.88 (2H, m, arom. H); and 7.11-7.17 (2H, m, arom. H);

$^{13}$C NMR (75 MHz; D$_2$O) δ: 19.33 (s, CH$_3$); 26.89 (s, —CH$_2$); 43.04 (d, α-CH, $^1J_{CP}$=131.3 Hz); 46.35 (d, γ-CH$_2$, $^3J_{CP}$=17.3 Hz); 55.55 (s, OCH$_3$); 114.16 (d, =CH); 130.32 (d, J$_{CP}$=6.1 Hz, =CH); 131.10 (d, J$_{CP}$=7.2 Hz, =C); 157.61 (m, =C); and 173.70 (s, C=O);

$^{31}$P NMR (121 MHz; D$_2$O) δ: 23.32 and 23.67 (minor and major isomer respectively); and ESI-MS: Calculated for C$_{12}$H$_{17}$NO$_6$P [M−H]$^-$: 302.0792. Found: 302.0794.

3-(N-hydroxyacetamido)-1-(4-chlorophenyl)propylphosphonic acid (2d)

$^1$H NMR (300 MHz; D$_2$O) δ: 1.58 and 1.87 (3H, 2×s, minor and major CH$_3$); 1.95-2.14 (1H, m, β-CH); 2.17-2.36 (1H, m, β-CH); 2.72-2.84 (1H, m, α-CH); 3.22-3.32 (1H, m, γ-CH); 3.35-3.50 (1H, m, γ-CH); 7.13-7.20 (2H, m, arom. H); and 7.20-7.28 (2H, m, arom. H);

$^{13}$C NMR (75 MHz; D$_2$O) δ: 19.28 (s, CH$_3$); 26.77 (s, —CH$_2$); 43.46 (d, α-CH, $^1J_{CP}$=129.6 Hz); 46.23 (d, γ-CH$_2$, $^3J_{CP}$=17.6 Hz); 128.40 (d, =CH); 130.65 (d, J$_{CP}$=5.8 Hz, =CH); 131.77 (d, =C); 137.24 (d, J$_{CP}$=7.2 Hz, =C); and 173.70 (s, C=O); and ESI-MS: Calculated for C$_{11}$H$_{14}$ClNO$_5$P [M−H]$^-$: 306.0297. Found: 306.0293.

3-(N-hydroxyacetamido)-1-(3,4-dichlorophenyl)propylphosphonic acid (2e)

$^1$H NMR (300 MHz; D$_2$O) δ: 1.61 and 1.86 (3H, 2×s, CH$_3$); 1.97-2.12 (1H, m, β-CH); 2.17-2.34 (1H, m, β-CH); 2.78 (1H, ddd, J$_{HP}$=21.8 Hz, J$_{HH}$=2.9 Hz and J$_{HH}$=12.3 Hz, α-CH); 3.25-3.34 (1H, m, γ-CH); 3.36-3.49 (1H, m, γ-CH); 7.06-7.13 (1H, m, arom. H); and 7.32-7.40 (2H, m, arom. H);

$^{13}$C NMR (75 MHz; D$_2$O) δ: 19.23 (s, CH$_3$); 26.68 (s, —CH$_2$); 43.36 (d, α-CH, $^1J_{CP}$=129.3 Hz); 48.86 (d, γ-CH$_2$, $^3J_{CP}$=17.0 Hz); 128.93 (d, J$_{CP}$=5.8 Hz, =CH); 129.78 (d, =C); 130.26 (d, =CH); 130.93 (d, J$_{CP}$=6.3 Hz, =CH); 131.51 (d, =C); 139.24 (d, J$_{CP}$=7.2 Hz, =C); and 173.70 (s, C=O);

$^{31}$P NMR (121 MHz; D$_2$O) δ: 21.51 and 21.90 (minor and major isomer respectively); and ESI-MS: Calculated for C$_{11}$H$_{13}$Cl$_2$NO$_5$P [M−H]$^-$: 339.9907. Found: 339.9901.

B. Using the Vinylic Tributyltin Synthon

An alternative convenient precursor for the desired phosphonic acid compounds is the tributyl stannyl propenyl phosphonate synthon (106) according to the following formula:

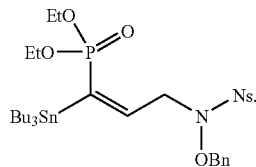

The synthesis of said synthon (see also steps a-c of sheme 4 here under) started with the conversion of tetrahydropyranyl-protected propargyl alcohol to diethyl 3-hydroxy-ethynylphosphonate. Subsequently, the 3-hydroxy group was displaced by a protected hydroxylamino under Mitsunobu conditions, which succeeded using N-benzyloxy-2-nitrobenzenesulfonamide. The 2-nitrobenzenesulfonamide (or Nosyl/Ns) moiety effectively enhanced the acidity of the proton on the nitrogen.

Subsequently, a palladium-catalyzed addition of tri-n-butyltin hydride (also referred to as Bu$_3$SnH) to the triple bond of compound 109 afforded tributyl stannyl propenyl phosphonate synthon (106) as the preferred single-trans regioisomer in an excellent yield of 90%. The trans stereochemistry was assigned using the $^3J_{PH}$ coupling constant in the $^1$H NMR spectrum (62.7 Hz), which is in accordance with the large coupling constant known for a vinylic proton trans to the phosphonate.

Step (d) in the synthetic route in scheme 4, is a Stille coupling reaction. Optimization of the Stille coupling on the organotin derivative 106 led us to obtain compounds 110f-g in good yields using a combination of Pd$_2$dba$_3$, tri(2-furyl)phosphine and anhydrous copper iodide in NMP. Under these conditions virtually no homo-coupling was detected and the stereochemistry of the double bond was retained. Treatment of a solution of 110f-g in acetonitrile containing 2% of DMSO and 4 eq. of K$_2$CO$_3$ with thophenol (3 eq.) and subsequent treatment with acetic anhydride (10 eq.) afforded 112f-g.

Alternatively, steps (d) and (e) (Scheme 1) can be interchanged. Compound 6 was first deprotected and acylated in situ to afford 111 in excellent yield. Subsequent Stille coupling using the above-mentioned conditions led to compounds 112a-e and 112h in good to excellent yields. The method proved compatible with a wide range of functionalities, including hetereoaromatic rings (112g-h).

Scheme 4 illustrates the synthesis of N-formyl fosmidomycin analogues in the vinylic tributyltin synthon route.

[Scheme 4]

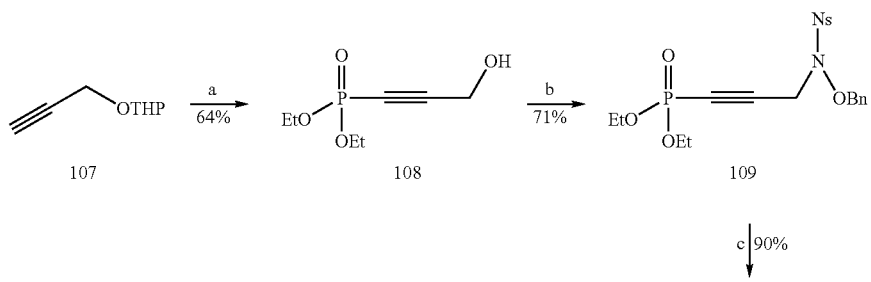

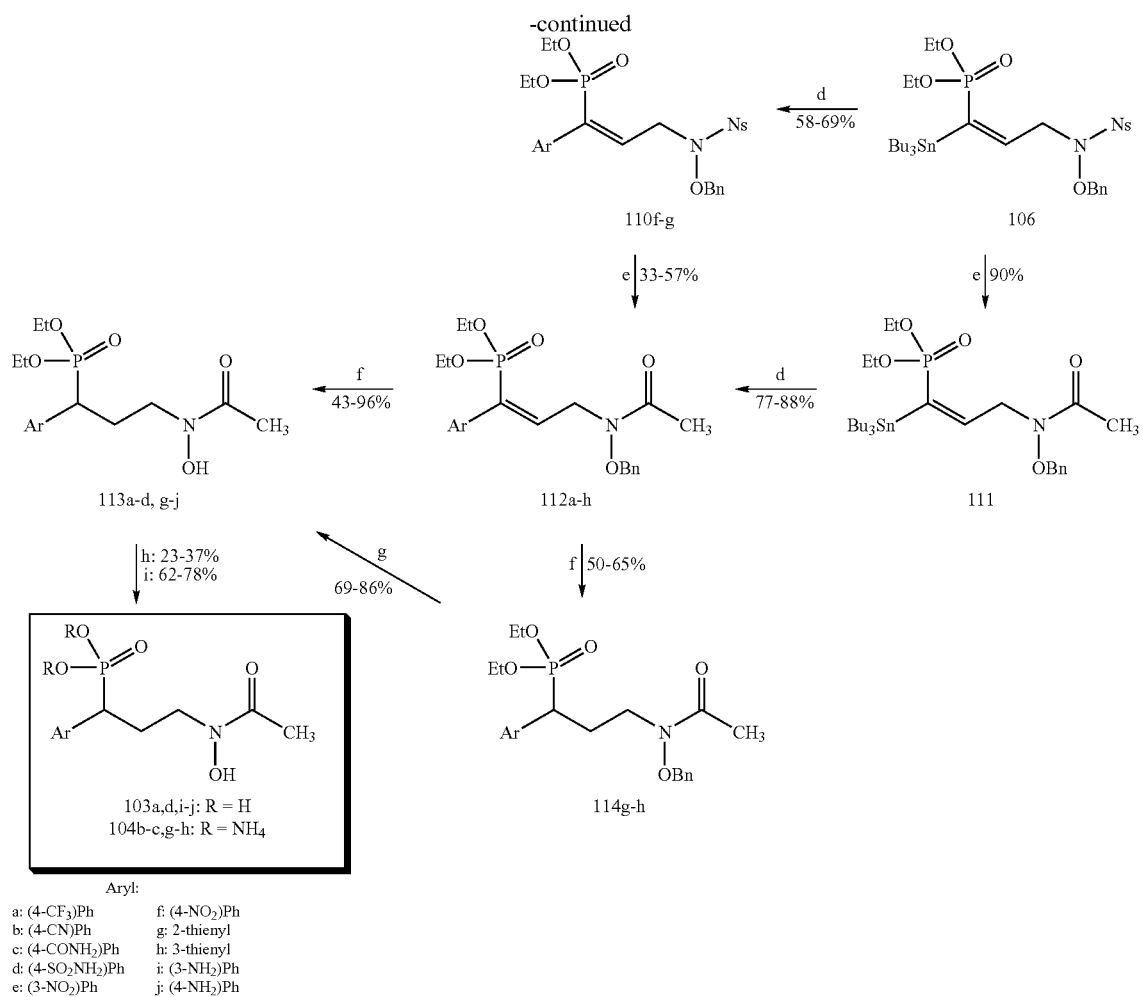

The reduction of the alpha,beta-unsaturated bond, combined with the removal of the benzyl protecting group on compounds 112a-f was accomplished using palladium on carbon (Pd/C) and anhydrous $Na_2CO_3$ in dry THF under positive $H_2$-pressure. Reaction times varied from 3 to 14 hours to afford compounds 113a-d and 113i-j in excellent yields. During this hydrogenation step little or no deoxygenation was observed. In case of the conversion of compound 112b, short reaction times were necessary to prevent reduction of the nitrile substituent on the phenyl group. Reduction of the nitro group in compounds 112e-f was unavoidable, resulting in amino compounds 113i-j. Furthermore, reduction of the 2-thienyl (112g) and 3-thienyl (112h) compounds was successfully accomplished using more than 1 equivalent of Pd/C. However, removal of the benzyl protecting group was not observed for the thienyl compounds, yielding the O-protected saturated compounds 114g-h. Subsequent removal of the O-benzyl group with boron trichloride ($BCl_3$) afforded compounds 113g-h in good to excellent yields. Finally, the alpha-aryl phosphonate esters 113a-d, g-j were hydrolyzed with trimethylsilyl bromide (TMSBr).

Two different methods were used for purification of the final compounds. The first, more traditional, method used for the purification of compounds 103a,d, and i-j, involved removal of the solvent, addition of water, lyophilization of the solution and purification of the solids via reversed phase chromatography. The second methodology comprised the steps of removal of the solvent, addition of water followed by dropwise addition of a 5% aqueous $NH_4OH$-solution until the pH reached 8 to 9. Subsequently the solution was lyophilized and the product was purification via column chromatography e.g. using Whatman CF11-cellulose. LC-MS analysis (Liquid Chromatography-Mass Spectrometry) of the crude solids before chromatographic purification only showed $NH_4Br$ (resulting from the reaction of TMSBr with $NH_4OH$) as a contaminant. CF11-cellulose proved very effective in separating this contaminant from compounds 104b-c and g-h in high yields due to the low affinity of the phosphonic acids for the stationary phase. Additionally the resulting bis-ammonium salts of the alpha-aryl-phosphonate showed excellent solubility in water.

Diethyl 3-hydroxy-propynylphosphonate (108)

A 1.6 M n-butyllithium solution in hexane (n-BuLi: 47.6 mL, 71.3 mmol) was added dropwise to a stirred solution of tetrahydro-2-(2-propynyloxy)-2H-pyran (7, 10 g, 71.3 mmol) in dry tetrahydrofurane (THF, 100 mL) at −78° C. After 30 min of stirring at the same temperature, a solution of diethylchlorophosphate (11.4 mL, 78.5 mmol) in dry THF (100 mL) was added drop-wise. The mixture was stirred for another 30 min at −78° C. The reaction was quenched with saturated aqueous NH₄Cl (100 mL) and the aqueous layer was extracted three times with diethyl ether (Et₂O, 100 mL). The combined organic layers were dried on anhydrous MgSO₄, filtered and the solvents were removed under reduced pressure. The residual oil was dissolved in MeOH (200 mL) and para toluenesulfonic acid (p-TsOH; 1.36 g, 7.13 mmol) was added. The reaction mixture was stirred overnight at room temperature. The solvent was removed under reduced pressure and the residual oil was purified by column chromatography using a mixture of pentane/acetone (volume ratio 3/2) yielding 8.75 g of a colorless oil (64%) which characterized as follows:

$R_f$ 0.30 (pentane/acetone: 3/2);
¹H NMR (300.13 MHz, CDCl₃) δ 1.36 (6H, td, J=7.1 and 0.6 Hz), 2.89 (1H, br s), 4.16 (4H, dq, J=8.3 and 7.0 Hz), 4.35 (2H, d, J=3.7 Hz);
¹³C NMR (75.47 MHz, CDCl₃) δ 16.0 (—CH₃, $^3J_{PC}$=7.1 Hz), 50.6 (—OCH₂, $^3J_{PC}$=4.4 Hz), 63.5 (—OCH₂, $^2J_{PC}$=5.5 Hz), 76.3 (≡C—P, $^1J_{PC}$=298.6 Hz), 100.0 (≡C, $^2J_{PC}$=50.5 Hz);
³¹P NMR (121.50 MHz, CDCl₃) δ −6.7;
ESMS found m/z 193 ([M]+H⁺).

Diethyl 3-[N-benzyloxy,N-(2-nitrobenzenesulfonyl) amino]-propynyl phosphonate (109)

To a stirred solution of diethyl 3-hydroxy-propynylphosphonate (108) (6.58 g), N-benzyloxy,N-(2-nitrobenzene)sulfonamide (11.5 g,) and triphenylphosphine (PPh₃) (9.8 g,) in dry THF (180 mL) was added a solution of DEAD (6.91 mL 85%,) in dry THF (90 mL) over 1 hour at room temperature. The mixture was stirred for 20 hours at room temperature. The solvent was removed under reduced pressure and the residual oil was purified by column chromatography in two sequential steps: on a first column the product was eluted using a mixture of pentane/CH₂Cl₂/acetone (volume ratio 2/7/1), and the resulting product was further purified on a second column after loading the product onto the column in Et₂O and elution with a mixture of CH₂Cl₂/acetone (volume ration 1/1). The method yielded 11.7 g of a thick amber oil (71%). The product was characterized as follows:

$R_f$ 0.40 (pentane/CH₂Cl₂/acetone: 2/7/1);
¹H NMR (300.13 MHz, CDCl₃) δ 1.29 (6H, dt, J=7.1 and 0.6 Hz), 3.99-4.06 (4H, m), 4.18 (2H, d, J=3.9 Hz), 5.15 (2H, s), 7.36-7.45 (5H, m), 7.56 (1H, dd, J=7.8 and 1.2 Hz), 7.67 (1H, app dt, J=7.7 and 1.3 Hz), 7.78 (1H, app dt, J=7.7 and 1.5 Hz), 8.04 (1H, dd, J=7.9 and 1.3 Hz);
¹³C NMR (75.47 MHz, CDCl₃) δ 16.0 (CH₃, $^4J_{PC}$=7.2 Hz), 43.1 (—NCH₂, $^3J_{PC}$=5.5 Hz), 63.3 (—OCH₂, $^3J_{PC}$=5.5 Hz), 76.1 (≡C—P, $^1J_{PC}$=293.7 Hz), 80.6 (—OCH₂), 91.9 (≡C, $^2J_{PC}$=51.0 Hz), 123.9 (≡CH), 126.0 (≡C), 128.7 (≡CH), 129.2 (≡CH), 129.9 (≡CH), 131.4 (≡CH), 133.2 (≡CH), 134.2 (≡C), 135.6 (≡CH), 149.5 (≡C);
³¹P NMR (121.50 MHz, CDCl₃) δ 8.2;
(ESI-MS): Calculated for C₂₀H₂₃N₂O₈PS ([M]+H⁺) 483.09911. Found 483.09654.

Diethyl (E)-3-[N-(benzyloxy),N-(2-nitrobenzenesulfonyl)amino]-1-(tributyl-stannyl)-propenylphosphonate (106)

To a solution of Diethyl 3-[N-benzyloxy,N-(2-nitrobenzenesulfonyl)amino]-propynylphosphonate (109) (10.4 g, 21.6 mmol) and Tetrakis(triphenylphosphine)-palladium(0) (Pd (PPh₃)₄) (474 mg, 0.430 mmol) in dry THF (100 mL) was added tributyltin hydride (BU₃SnH) (6.28 g, 21.6 mmol) over a period of 40 min at 0° C. The reaction mixture was stirred at 0° C. for one hour and was allowed to warm to room temperature over a period of time of 2 hours. The solvent was removed under reduced pressure and the crude oil was purified by column chromatography using a mixture of pentane/ acetone (volume ratio 3/1), yielding 15 g of an amber oil (90%).

The product was characterized as follows:
$R_f$ 0.31 (pentane/acetone: 3/1);
¹H NMR (300.13 MHz, CDCl₃) δ 0.87 (9H, t, J=7.2 Hz), 0.93-0.98 (6H, m), 1.19 (6H, t, J=7.0 Hz), 1.26-1.35 (6H, m), 1.42-1.52 (6H, m), 3.88-3.95 (4H, m), 4.39-4.41 (2H, m), 5.06 (2H, s), 6.53 (1H, dt, J=62.7 and 5.5 Hz), 7.33-7.35 (5H, m), 7.54 (1H, d, J=7.7 Hz), 7.62 (1H, app t, J=7.6 Hz), 7.71 (1H, app t, J=7.5 Hz), 8.04 (1H, d, J=8.0 Hz);
¹³C NMR (75.47 MHz, CDCl₃) δ 10.8 (—CH₂), 13.6 (—CH₃), 27.3 (—CH₂), 28.8 (—CH₂), 55.2 (—NCH₂, $^3J_{PC}$=13.8 Hz), 61.1 (—OCH₂, $^3J_{PC}$=5.5 Hz), 80.2 (—OCH₂), 123.8 (≡CH), 126.6 (≡C), 128.5 (≡CH), 128.9 (≡CH), 129.6 (≡CH), 131.1 (≡CH), 132.6 (≡CH), 136.2 (≡C), 136.4 (≡C—P, $^1J_{PC}$=247.6 Hz), 149.8 (≡C), 152.1 (≡CH, $^2J_{PC}$=1.7 Hz);
³¹P NMR (121.50 MHz, CDCl₃) δ 21.4;
(ESI-MS): Calculated for C₃₂H₅₁N₂O₈PSSn ([M, ¹²⁰Sn]+ Na⁺) 797.20235. Found 797.19986.

Diethyl (Z)-3-[N-benzyloxy,N-(2-nitrobenzenesulfonyl)amino]-1-(4-nitrophenyl)-Propenylhosphonate (110f)

Tri-(2-furyl)phosphine (12 mg, 0.051 mmol) was added to a solution of tris(dibenzylidenacetone)dipalladium (Pd₂ dba₃·CHCl₃) (6 mg, 0.0065 mmol) in anhydrous N-methylpyrrolidinone (NMP) (2 mL) and the mixture was stirred for one hour at room temperature. A solution of diethyl (E)-3-[N-(benzyloxy),N-(2-nitrobenzenesulfonyl)amino]-1-(tributylstannanyl)-propenylphosphonate (106) (216 mg, 0.280 mmol) and 1-iodo-4-nitrobenzene (62 mg, 0.249 mmol) in anhydrous NMP (5 mL) was added over a time period of 15 min. After subsequent addition of anhydrous copper iodide (CuI; 46 mg, 0.280 mmol), the reaction mixture was stirred overnight while shielded from light. The product was first isolated by extraction: ethylacetate (EtOAc) (100 mL) was added and the organic layer was washed 3 times with 5% NH₄OH (10 mL) and 3 times with saturated aqueous NaCl (10 mL). The organic layer was dried on anhydrous MgSO₄, filtered and the solvents were removed under reduced pressure. The residual oil was then purified by column chromatography using pentane/dichloromethane/acetone (in a volume ratio of 3/1/1) yielding 98 mg of a pale yellow oil (58%). The product was characterized as follows:

$R_f$ 0.48 (pentane/acetone: 1/1);
¹H NMR (300.13 MHz, CDCl₃) δ 1.16 (6H, t, J=7.0 Hz), 3.92 (2H, ddq, J=10.4, 8.4 and 7.1 Hz), 4.01 (2H, ddq, J=10.3, 8.1 and 7.0 Hz), 4.47 (2H, dd, J=5.7 and 3.3 Hz), 5.01 (2H, s), 6.05 (1H, dt, J=46.0 and 6.0 Hz), 7.16-7.33 (7H, m), 7.61 (1H, dd, J=7.7 and 1.4 Hz), 7.72 (1H, app dt, J=7.7 and 1.4 Hz), 7.79 (1H, app dt, J=7.7 and 1.5 Hz), 8.1 (1H, dd, J=8.0 and 1.4 Hz), 8.14 (2H, d, J=8.4 Hz);
¹³C NMR (75.47 MHz, CDCl₃) δ 16.1 (—CH₃, $^3J_{PC}$=6.6 Hz), 53.1 (—NCH₂, $^3J_{PC}$=5.4 Hz), 62.3 (—OCH₂, $^3J_{PC}$=6.0 Hz), 79.6 (—OCH₂), 123.4 (≡CH), 123.9 (≡CH), 126.0 (≡C), 128.5 (≡CH), 128.8 (≡CH, $^3J_{PC}$=1.1 Hz), 129.0 (≡CH), 130.1 (≡CH), 131.3 (≡CH), 132.6 (≡C—P, $^1J_{PC}$=176.2 Hz), 132.7 (≡CH), 134.8 (≡C) 135.2 (≡C), 145.3 (≡C, $^2J_{PC}$=10.2 Hz), 145.8 (≡CH, $^2J_{PC}$=8.2 Hz), 147.3 (≡C, $^5J_{PC}$=1.1 Hz), 149.9 (≡C);
³¹P NMR (121.50 MHz, CDCl₃) δ 13.2;

(ESI-MS): Calculated for $C_{26}H_{28}N_3O_1PS$ ([M]+H$^+$) 606.13113. Found 606.13014.

Diethyl 3-[N-(benzyloxy),N-(2-nitrobenzenesulfonyl)amino]-1-thien-2-yl-propylphosphonate (110 h)

The title compound was obtained as a thick yellow oil according to the same procedure as 110f in 69% yield. The product was characterized as follows:

$R_f$ 0.43 (pentane/$CH_2Cl_2$/acetone: 2/1/1);

$^1$H NMR (300.13 MHz, $CDCl_3$) δ1.18 (6H, t, J=7.2 Hz), 3.93 (2H, ddq, J=10.1, 8.3 and 7.1 Hz), 3.98-4.09 (2H, ddq, J=10.1, 8.3 and 7.1), 4.53 (2H, dd, J=6.3 and 3.2 Hz), 5.06 (2H, s), 6.42 (1H, dt, J=45.7 and 6.3 Hz), 6.96 (1H, dd, J=5.1 and 3.7 Hz), 7.11-7.14 (1H, m), 7.20 (1H, dd, J=5.1 and 1.0 Hz), 7.25-7.37 (5H, m), 7.57 (1H, dd, J=7.8 and 1.5 Hz), 7.68 (1H, app dt, J=7.7 and 1.5 Hz), 7.75 (1H, app dt, 7.7 and 1.6 Hz), 8.08 (1H, dd, J=7.8 and 1.4 Hz);

$^{13}$C NMR (75.47 MHz, $CDCl_3$) δ 16.1 (—$CH_3$, $^3J_{PC}$=6.6 Hz), 52.9 (—$NCH_2$, $^3J_{PC}$=5.0 Hz), 62.3 (—$OCH_2$, $^2J_{PC}$=5.5 Hz), 80.1 (—$OCH_2$), 123.9 (=CH), 125.5 (=CH), 126.0 (=C), 127.0 (=CH, $^3J_{PC}$=3.8 Hz), 127.1 (=C—P, $^1J_{PC}$=175.6 Hz), 127.5 (=CH), 128.5 (=CH), 128.9 (=CH), 130.0 (=CH), 131.2 (=CH), 132.5 (=CH), 134.6 (=C), 135.0 (=CH), 140.1 (=C, $^2J_{PC}$=14.3 Hz), 141.7 (=CH, $^2J_{PC}$=8.8 Hz), 149.8 (=C);

$^{31}$P NMR (121.50 MHz, $CDCl_3$) δ 21.7;

ESMS m/z found: 567 ([M]+H$^+$).

Diethyl (E)-3-[N-acetyl,N-(benzyloxy)amino]-1-(tributylstannanyl)-propenylphosphonate (111)

To a stirred solution of diethyl (E)-3-[N-(benzyloxy),N-(2-nitrobenzene-sulfonyl)amino]-1-(tributylstannanyl)-propenylphosphonate (106) (15 g, 19.4 mmol) and anhydrous $K_2CO_3$ (10.8 g, 77.8 mmol) in acetonitrile (MeCN; 500 mL) and dry dimethylsulfoxide (DMSO; 10 mL) was added thiophenol (PhSH; 6 mL, 58.3 mmol) over a period of 30 min and at 70° C. After stirring for 1 hour at the same temperature, acetic acid anhydride ($Ac_2O$; 18.3 mL, 195 mmol) was added and the reaction was stirred for another 30 min. After cooling down to room temperature, the reaction was quenched by adding saturated $NaHCO_3$ in water. The aqueous layer was extracted with $CH_2Cl_2$. The combined organic fractions were dried on anhydrous $MgSO_4$ and filtered. The solvents were removed under reduced pressure. The residual oil was purified by column chromatography using a mixture of pentane/$CH_2Cl_2$/acetone (in a volume ratio of 2/1/1) yielding 11 g of a yellow oil (90%). The product was characterized as follows:

$R_f$ 0.35 (pentane/$CH_2Cl_2$/acetone: 3/1/1);

$^1$H NMR (300.13 MHz, $CDCl_3$) δ 0.85 (9H, t, J=7.3 Hz), 0.94-0.99 (6H, m), 1.22-1.34 (12H, m), 1.41-1.51 (6H, m), 2.07 (3H, s), 3.94-4.11 (4H, m), 4.86 (2H, s), 4.89-4.99 (2H, m), 6.48 (1H, dt, J=63.5 and 5.9 Hz);

$^{13}$C NMR (75.47 MHz, $CDCl_3$) δ 10.6 (—$CH_2$), 13.6 (—$CH_3$), 16.4 (—$CH_3$, $^3J_{PC}$=6.6 Hz), 20.5 (—$CH_3$), 27.3 (—$CH_2$), 28.7 (—$CH_2$), 57.1 (—$NCH_2$), 61.1 (—$OCH_2$, $^2J_{PC}$=5.5 Hz), 76.0 (—$OCH_2$), 128.6 (=CH), 128.9 (=CH), 129.5 (=CH), 134.4 (=C), 135.1 (=C—P, $^1J_{PC}$=133.4 Hz), 155.0 (=CH), 172.1 (N—C=O);

(ESI-MS): Calculated for $C_{28}H_{50}NO_5PSn$ ([M, $^{120}$Sn]+H$^+$) 632.25269. Found 632.25282.

Diethyl (E)-3-[N-(benzyloxy),N-formylamino)-1-(tributylstannanyl)-propenylphosphonate (115)

To a stirred solution of diethyl (E)-3-[N-(benzyloxy),N-(2-nitrobenzene-sulfonyl)amino]-1-(tributylstannanyl)-propenylphosphonate (106) (3.04 g,) and anhydrous $K_2CO_3$ (728 mg,) in MeCN (100 mL) and dry DMSO (2 mL) was added PhSH (404 μL,) over 30 minutes at 70° C. and the reaction mixture was stirred overnight at the same temperature. A formylating solution was prepared in a separate flask by adding HCOOH (99%, 163 μL, 4.32 mmol) dropwise to a solution of 1,1'-carbonyldiimidazole (702 mg, 4.32 mmol) in dry $CH_2Cl_2$ (6.4 mL) at 0° C. for and stirring 1 h. The formylating solution at 0° C. was added dropwise to the reaction mixture that was first cooled to 0° C. as well. The reaction mixture was stirred for one hour at 0° C. Then the reaction was quenched with saturated $NaHCO_3$ in water and the aqueous layer was extracted with $CH_2Cl_2$. The combined organic fractions were dried on anhydrous $MgSO_4$ and filtered. The solvents were removed under reduced pressure and the resulting oil was purified by column chromatography using a mixture of pentane/$CH_2Cl_2$/acetone (in a volume ratio of 4/1/1) yielding 1.42 g of a yellow oil (59%). The product was characterized as follows:

$R_f$ 0.43 (hexane/acetone: 7/3);

$^1$H NMR (300.13 MHz, $CDCl_3$) δ 0.86 (6H, minor, t, J=7.3 Hz), 0.87 (6H, major, t, J=7.2 Hz), 0.95-1.00 (6H, m), 1.22-1.34 (12H, m), 1.41-1.57 (6H, m), 3.95-4.06 (6H, m), 4.71 (2H, minor, s), 4.87 (4H, major, m), 6.34-6.55 (1H, minor, m), 6.71 (1H, major, dt, J=64.2 and 5.8 Hz), 7.27-7.35 (5H, m), 8.16 (1H, br s);

$^{13}$C NMR (75.47 MHz, $CDCl_3$) δ 10.6 (—$CH_2$, minor), 10.7 (—$CH_2$, major), 13.6 (—$CH_3$, minor), 13.6 (—$CH_3$, major), 16.3 (—$CH_3$, minor, $^3J_{PC}$=6.6 Hz); 16.4 (—$CH_3$, major, $^3J_{PC}$=7.2 Hz), 27.2 (—$CH_2$, minor) 27.3 (—$CH_2$, major), 28.7 (—$CH_2$ minor), 28.8 (—$CH_2$, major), 45.7 (—$NCH_2$, major, $^3J_{PC}$=15.4 Hz), 54.0 (—$NCH_2$, minor, $^3J_{PC}$=13.2 Hz), 61.0 (—$OCH_2$, minor, $^2J_{PC}$=5.5 Hz), 61.1 (—$OCH_2$, major, $^2J_{PC}$=5.5 Hz), 76.1 (—$OCH_2$, minor), 77.0 (—$OCH_2$, major), 127.8 (=CH, minor), 128.2 (=CH, minor), 128.3 (=CH, minor), 128.6 (=CH, major), 129.0 (=CH, major), 129.5 (=CH, major), 133.9 (=C—P, $^1J_{PC}$=133.4 Hz), 137.7 (=C), 153.6 (=CH, minor), 157.8 (=CH, major), 162.6 (N—C=O);

$^{31}$P NMR (121.50 MHz, $CDCl_3$) δ 21.7, 22.4 (minor, major);

(ESI-MS): Calculated for $C_{27}H_{48}NO_5PSn$ ([M, $^{120}$Sn]+H$^+$) 618.23704. Found 618.23725.

Diethyl (Z)-3-[N-acetyl,N-(benzyloxy)amino]-1-(4-trifluoromethylphenyl)-propenylphosphonate (112a)

Tri-(2-furyl)phosphine (27.2 mg, 0.116 mmol) was added to a solution of $Pd_2$ $dba_3$.$CHCl_3$ (13.6 mg, 0.0149 mmol) in anhydrous NMP (3 mL) and the mixture was stirred for one hour at room temperature. A solution of diethyl (E)-3-[N-acetyl,N-(benzyloxy)amino]-1-(tributylstannanyl)-propenylphosphonate (111) (400 mg, 0.634 mmol) and 1-iodo-4-trifluoromethylbenzene (154 mg, 0.566 mmol) in anhydrous NMP (5 mL) was added in 15 min. After the addition of anhydrous CuI (104 mg, 0.634 mmol) the reaction mixture was stirred overnight while secluded from light. EtOAc (200 mL) was added and the organic layer was washed 3 times with 5% $NH_4OH$ in water (24 mL) and 3 times with saturated aqueous NaCl (24 mL). The organic layer was dried on anhydrous $MgSO_4$, filtered and the solvents were removed under reduced pressure. The residual oil was purified by column chromatography using a mixture of pentane/acetone (in a volume ratio of 55/45) yielding 228 mg of a pale yellow oil (88%). The product was characterized as follows:

$R_f$ 0.43 (pentane/acetone: 3/2);

$^1$H NMR (300.13 MHz, CDCl$_3$) δ 1.24 (6H, t, J=7.1 Hz), 2.09 (3H, s), 3.98-4.18 (4H, m), 4.91 (2H, s), 5.06 (2H, dd, J=5.8 and 2.9 Hz), 6.46 (1H, dt, J=47.1 and 6.4 Hz), 7.35-7.41 (5H, m), 7.43 (2H, d, J=8.1 Hz), 7.56 (2H, d, J=8.4 Hz);

$^{13}$C NMR (75.47 MHz, CDCl$_3$) δ 16.2 (—CH$_3$, $^3J_{PC}$=6.6 Hz), 20.5 (—CH$_3$), 45.3 (—NCH$_2$), 62.2 (—OCH$_2$, $^2J_{PC}$=5.5 Hz), 76.4 (—OCH$_2$), 123.9 (—CF$_3$, q, $^1J_{FC}$=286.5 Hz), 128.5 (=CH, q, $^3J_{FC}$=3.4 Hz), 128.7 (=CH), 129.0 (=CH), 129.4 (=CH), 129.8 (=C, dq, $^2J_{FC}$=32.0 Hz, $^5J_{PC}$=1.1 Hz), 132.9 (=C—P, $^1J_{PC}$=196.5 Hz), 134.0 (=C), 142.5 (=C, $^2J_{PC}$=11.5 Hz), 147.4 (=CH, $^2J_{PC}$=10.5 Hz), 172.6 (N—C=O);

$^{31}$P NMR (121.50 MHz, CDCl$_3$) δ 514.3;

(ESMS) m/z found 486 ([M]+H$^+$).

Diethyl 3-[N-acetyl,N-(benzyloxy)amino]-1-(4-cyanophenyl)-propenylphosphonate (112b)

The title compound was obtained according to the same procedure as 112a as a thick yellow oil in 84% yield. The product was characterized as follows:

$R_f$ 0.29 (pentane/acetone: 3/2);

$^1$H NMR (300.13 MHz, CDCl$_3$) δ 1.22 (6H, t, J=7.1 Hz), 2.08 (3H, s), 3.95-4.16 (4H, m), 4.89 (2H, s), 5.03 (2H, dd, J=6.0 and 3.0 Hz), 6.38 (1H, dt, J=46.8 and 6.3 Hz), 7.34-7.39 (5H, m), 7.42 (2H, d, J=7.5 Hz), 7.58 (2H, d, J=8.4 Hz);

$^{13}$C NMR (75.47 MHz, CDCl$_3$) δ 16.2 (—CH$_3$, $^3J_{PC}$=6.6 Hz), 20.5 (—CH$_3$), 45.3 (—NCH$_2$), 62.2, (—OCH$_2$, $^2J_{PC}$=5.5 Hz), 76.4 (—OCH$_2$), 111.5 (=C), 118.5 (—C≡N), 128.6 (=CH), 128.8 (=CH, $^3J_{PC}$=4.4 Hz), 129.0 (=CH), 129.3 (=CH), 131.9 (=CH), 132.5 (=C—P, $^1J_{PC}$=176.8 Hz), 134.1 (=C), 143.5 (=C, $^2J_{PC}$=10.4 Hz), 147.8 (=CH, $^2J_{PC}$=9.3 Hz), 172.6 (N—C=O);

$^{31}$P NMR (121.50 MHz, CDCl$_3$) δ 13.9;

ESMS m/z 443 ([M]+H$^+$).

Diethyl 3-[N-acetyl, N-(benzyloxy)amino]-1-(4-carbamoylhenyl)-PropenVlphosphonate (112c)

The title compound was obtained according to the same procedure as 112a as a thick yellow oil in 79% yield. The product was characterized as follows:

$R_f$ 0.29 (CH$_2$Cl$_2$/MeOH: 95/5);

$^1$H NMR (300.13 MHz, CDCl$_3$) δ 1.21 (6H, t, J=7.1 Hz), 2.08 (3H, s), 3.83-4.03 (4H, m), 4.09 (2H, s), 5.04 (2H, dd, J=5.7 and 2.8 Hz), 6.46 (1H, dt J=47.2 and 6.3 Hz), 7.34-7.40 (7H, m), 7.78 (2H, d, J=8.5);

$^{13}$C NMR (75.47 MHz, CDCl$_3$) δ 16.2 (—CH$_3$, $^3J_{PC}$=6.6 Hz), 20.5 (—CH$_3$), 45.3 (—NCH$_2$), 62.1 (—OCH$_2$, $^2J_{PC}$=5.5 Hz), 76.4 (—OCH$_2$), 127.2 (=CH), 128.3 (=CH, $^3J_{PC}$=5.0 Hz), 128.6 (=CH), 129.0 (=CH), 129.4 (=CH), 132.5 (=C, $^5J_{PC}$=1.1 Hz), 133.0 (=C—P, $^1J_{PC}$=180.6), 134.1 (=C), 142.5 (=C, $^2J_{PC}$=10.4 Hz), 147.0 (=CH, $^2J_{PC}$=9.9 Hz), 165.3 (N—C=O), 172.5 (N—C=O);

$^{31}$P NMR (121.50 MHz, CDCl$_3$) δ 14.5;

ESMS m/z 461 ([M]+H$^+$), 943 (2[M]+H$^+$).

Diethyl 3-[N-acetyl, N-(benzyloxy)amino]-1-(4-sulfamoylphenyl)-propenylphosphonate (112d)

The title compound was obtained according to the same procedure as 112a as a pale yellow oil in 84% yield. The product was characterized as follows:

$R_f$ 0.31 (CH$_2$Cl$_2$/MeOH: 95/5);

$^1$H NMR (300.13 MHz, CDCl$_3$) δ 1.24 (6H, t, JHt, J=7.0 Hz), 2.09 (3H, s), 4.03 (2H, ddq, J=10.2, 8.3 and 7.0 Hz), 4.10 (2H, ddq, J=10.2, 7.2 and 7.2 Hz), 4.90 (2H, s), 5.02 (2H, dd, J=5.8 and 3.0 Hz), 5.14 (2H, br s), 6.45 (1H, dt, J=46.8 and 6.3 Hz), 7.35-7.40 (5H, m), 7.45, (2H, d, J=7.3 Hz), 7.85 (2H, d, J=8.4 Hz);

$^{13}$C NMR (75.47 MHz, CDCl$_3$) δ 16.2 (—CH$_3$, $^3J_{PC}$=6.6 Hz), 20.5 (—CH$_3$), 45.4 (—NCH$_2$), 62.3 (—OCH$_2$, $^2J_{PC}$=5.5 Hz), 76.4 (—OCH$_2$), 126.3 (=CH), 128.6 (=CH), 128.9 (=CH, $^3J_{PC}$=4.4 Hz), 129.1 (=CH), 129.4 (=CH), 132.5 (=C—P, $^1J_{PC}$=176.5 Hz), 134.1 (=C), 141.3 (=C—SO$_2$, $^5J_{PC}$=1.1 Hz), 143.3 (=C, $^2J_{PC}$=11.0 Hz), 147.6 (=CH, $^2J_{PC}$=10.4 Hz), 172.6 (N—C=O);

$^{31}$P NMR (121.50 MHz, CDCl$_3$) δ 14.1;

ESMS m/z 497 ([M]+H$^+$).

Diethyl 3-[N-acetyl, N-(benzyloxy)amino]-1-(3-nitrophenyl)-propenylphosphonate (112e)

The title compound was obtained according to the same procedure as 112a as a thick yellow oil in 78% yield. The product was characterized as follows:

$^1$H NMR (300.13 MHz, CDCl$_3$) δ 1.25 (6H, t, J=7.1 Hz), 2.10 (3H, s), 3.94 (2H, ddq, J=10.1, 8.3 and 7.1 Hz), 4.91 (2H, s), 5.06 (1H, dd, J=5.9 and 2.9 Hz), 6.49 (1H, dt, J=46.8 and 6.3 Hz), 7.33-7.42 (5H, m), 7.48 (1H, app t, J=8.0 Hz), 7.67 (1H, dd, J=7.8 and 1.2 Hz), 8.15 (1H, app dt, J=8.2 and 1.1 Hz), 8.21 (1H, d, J=1.7 Hz);

$^{13}$C NMR (75.47 MHz, CDCl$_3$) δ 16.2 (—CH$_3$, $^3J_{PC}$=6.1 Hz), 20.5 (—CH$_3$), 45.2 (—NCH$_2$), 62.3 (—OCH$_2$, $^2J_{PC}$=6.0 Hz), 76.5 (—OCH$_2$), 122.7 (=CH), 123.1 (=CH, $^3J_{PC}$=4.4 Hz), 128.8 (=CH), 129.1 (=CH), 129.2 (=CH), 129.5 (=CH), 132.0 (=C—P, $^1J_{PC}$=177.3 Hz), 134.2 (=C), 134.3 (=CH, $^3J_{PC}$=4.4 Hz), 140.6 (=C, $^2J_{PC}$=11.0 Hz), 147.9 (=C), 148.0 (=CH), 172.7 (N—C=O);

ESMS m/z 463 ([M]+H$^+$).

Diethyl 3-[N-Acetyl,N-(benzyloxy)amino]-1-(4-nitrophenyl)propenylphosphonate (112f)

The title compound was obtained according to the same procedure as 112a as a thick yellow oil in 79% yield. The product was characterized as follows:

$^1$H NMR (300.13 MHz, CDCl$_3$) δ 1.24 (6H, t, J=7.1 Hz), 2.10 (3H, s), 4.05 (2H, ddq, J=10.2, 8.3 and 7.0 Hz), 4.12 (2H, ddq, J=10.2, 8.0 and 7.1 Hz), 4.91 (2H, s), 5.05 (2H, dd, J=6.0 and 3.0 Hz), 6.50 (1H, dt, J=46.7 and 6.2 Hz), 7.36-7.41 (5H, m), 7.47-7.51 (2H, m), 8.16-8.18 (2H, m);

$^{13}$C NMR (75.47 MHz, CDCl$_3$) δ 16.2 (—CH$_3$, $^3J_{PC}$=6.1 Hz), 20.5 (—CH$_3$), 45.4 (—NCH$_2$), 62.3 (—OCH$_2$, $^2J_{PC}$=5.4 Hz), 76.5 (—OCH$_2$), 123.5 (=CH), 128.8 (=CH), 129.1 (=CH), 129.1 (=CH), 129.5 (=CH), 132.4 (=C—P, $^1J_{PC}$=176.1 Hz), 134.2 (=C), 145.5 (=C, $^2J_{PC}$=10.9 Hz), 147.3 (=C), 148.2 (=CH, $^2J_{PC}$=9.9 Hz), 172.8 (N—C=O);

$^{31}$P NMR (121.50 MHz, CDCl$_3$) δ 13.7;

ESMS m/z 463 ([M]+H$^+$).

Diethyl 3-[N-acetyl,N-(benzyloxy)amino)-1-thiophen-2-yl-propenylphosphonate (112g)

The title compound was obtained according to the same procedure as 112a as a thick yellow oil in 77% yield. The product was characterized as follows:

$R_f$ 0.35 (pentane/CH$_2$Cl$_2$/acetone: 2/1/1);

$^1$H NMR (300.13 MHz, CDCl$_3$) δ 1.25 (6H, t, J=7.1 Hz), 2.09 (3H, s), 4.03 (2H, ddq, J=10.2, 8.2 and 7.1 Hz), 4.11 (2H, ddq, J=10.1, 7.9 and 7.1 Hz), 4.90 (2H, s), 5.07-5.12 (2H, m), 6.68 (1H, dd, J=46.8 and 6.6 Hz), 6.95 (1H, dd, J=5.0 and 3.8 Hz), 7.18-7.20 (2H, m), 7.32-7.41 (5H, m);

$^{13}$C NMR (75.47 MHz, CDCl$_3$) δ 16.2 (—CH$_3$, $^3J_{PC}$=6.4 Hz), 20.5 (—CH$_3$), 44.7 (—NCH$_2$), 62.1 (—OCH$_2$, $^2J_{PC}$=5.0 Hz), 76.3 (—OCH$_2$), 125.4 (=CH), 126.4 (=C—P, $^1J_{PC}$=160.8 Hz), 126.8 (=CH, $^3J_{PC}$=3.8 Hz), 127.4 (=CH), 128.7 (=CH), 129.0 (=CH), 129.4 (=CH), 134.3 (=C), 140.3 (=C, $^2J_{PC}$=12.3 Hz), 144.5 (=CH, $^2J_{PC}$=10.4 Hz), 172.6 (N—C=O);

$^{31}$P NMR (121.50 MHz, CDCl$_3$) δ 14.1;

ESMS m/z 424 ([M]+H$^+$).

Diethyl 3-[N-acetyl, N-(benzyloxy)amino]-1-thiophen-3-yl-propenylphosphonate (112h)

The title compound was obtained according to the same procedure as 112a as a pale yellow oil in 83% yield. The product was characterized as follows:

R$_f$ 0.40 (pentane/acetone: 3/2);

$^1$H NMR (300.13 MHz, CDCl$_3$) δ 1.25 (6H, t, J=7.1 Hz), 2.09 (3H, s), 4.01 (2H, ddq, J=10.1, 8.2 and 7.1 Hz), 4.09 (2H, ddq, J=10.2, 7.7 and 7.2 Hz), 4.91 (2H, s), 5.08 (2H, dd, J=6.1 and 2.9 Hz), 6.62 (1H, dt, J=47.9 and 6.6 Hz), 7.14 (1H, app dt, J=5.1 and 1.2 Hz), 7.24 (1H, ddd, J=5.1, 3.0 and 0.9 Hz), 7.34-7.41 (6H, m);

$^{13}$C NMR (75.47 MHz, CDCl$_3$) δ 16.2 (—CH$_3$, $^3J_{PC}$=6.6 Hz), 20.6 (—CH$_3$), 44.8 (—NCH$_2$), 62.0 (—OCH$_2$, $^2J_{PC}$=5.5 Hz), 76.3 (—OCH$_2$), 123.2 (=CH, $^3J_{PC}$=5.5 Hz), 125.3 (=CH), 127.2 (=CH, J$_{PC}$=4.9 Hz), 127.78 (=C—P, $^1J_{PC}$=174.5 Hz), 128.7 (=CH), 129.0 (=CH), 129.4 (=CH), 134.4 (=C), 138.4 (=CH, $^2J_{PC}$=11.6 Hz), 144.4 (=CH, $^2J_{PC}$=10.5 Hz), 172.5 (N—C=O);

$^{31}$P NMR (121.50 MHz, CDCl$_3$) δ 15.6;

ESMS m/z 424 ([M]+H$^+$).

Diethyl 3-[N-(benzyloxy), N-formylamino]-1-(4-cyanophenyl)-propenylphosphonate (116)

The title compound was obtained according to the same procedure as 112a as a pale yellow oil in 83% yield. The product was characterized as follows:

R$_f$ 0.28 (hexane/acetone: 7/3);

$^1$H NMR (300.13 MHz, CDCl$_3$) δ 1.23 (6H, t, J=7.1 Hz), 4.00-4.14 (4H, m), 4.91 (2H, s), 4.96-4.99 (2H, m), 6.40 (1H, dt, J=46.5 and 6.4 Hz), 7.34-7.36 (5H, m), 7.42 (2H, d, J=7.7 Hz), 7.59 (2H, d, J=8.3 Hz); 8.18 (1H, br s);

$^{13}$C NMR (75.47 MHz, CDCl$_3$) δ 16.2 (—CH$_3$, $^3J_{PC}$=6.6 Hz), 43.7 (—NCH$_2$), 62.3 (—OCH$_2$, $^2J_{PC}$=6.0 Hz), 77.4 (—OCH$_2$), 111.7 (=C), 118.5 (—C≡N), 128.7 (=CH, $^3J_{PC}$=4.3 Hz), 129.1 (=CH), 129.5 (=CH), 132.0 (=CH), 133.4 (=C—P, $^1J_{PC}$=176.2 Hz), 134.0 (=C), 143.2 (=C, $^2J_{PC}$=10.9 Hz), 146.5 (=CH, $^2J_{PC}$=8.2 Hz), 163.0 (N—C=O);

$^{31}$P NMR (121.50 MHz, CDCl$_3$) δ 13.6;

ESMS m/z 429 ([M]+H$^+$).

Diethyl 3-[N-acetyl,N-(hydroxy)amino]-1-(4-trifluoromethylphenyl)-propylphosphonate (113a)

To a solution of diethyl (Z)-3-[N-acetyl,N-(benzyloxy)amino]-1-(4-trifluoromethylphenyl)-propenylphosphonate (112a) (266 mg, 0.547 mmol) dry THF (8.5 mL) was added anhydrous Na$_2$CO$_3$ (174 mg, 1.64 mmol) and Palladium on carbon (Pd/C; 133 mg, 10% Pd). The reaction was placed under H$_2$ (at 1 atmosphere) and was stirred for 4 hours at room temperature. The mixture was filtered over a celite pad and the pad was washed with portions of CH$_2$Cl$_2$. The filtrate was evaporated under reduced pressure and the residual oil was purified by column chromatography using a mixture of CH$_2$Cl$_2$/MeOH (in a volume ratio of 94/6) yielding a colorless oil (85%). The product was characterized as follows:

R$_f$ 0.29 (CH$_2$Cl$_2$/acetone: 1/1);

$^1$H NMR (300.13 MHz, CDCl$_3$) δ 1.19 (3H, t, J=7.1 Hz), 1.23 (3H, t, J=7.1 Hz), 2.12 (3H, s), 2.14-2.61 (2H, m), 3.18 (1H, dt, J=23.1 and 6.1 Hz), 3.36 (1H, dt, J=14.2 and 4.8 Hz), 3.44-4.02 (5H, m), 7.40 (2H, d, J=7.7 Hz), 7.57 (2H, d, J=7.9 Hz), 9.44 (1H, br s);

$^{13}$C NMR (75.47 MHz, CDCl$_3$) δ 16.2 (—CH$_3$, $^3J_{PC}$=6.0 Hz), 20.5 (—CH$_3$), 27.9 (—CH$_2$, $^2J_{PC}$=2.2 Hz), 41.0 (P—CH, minor, $^1J_{PC}$=139.9 Hz), 41.8 (P—CH, major, $^1J_{PC}$=137.2 Hz), 46.2 (—NCH$_2$, major, $^3J_{PC}$=10.4 Hz), 46.5 (—NCH$_2$, minor, $^3J_{PC}$=15.9 Hz), 62.8 (—OCH$_2$, $^2J_{PC}$=7.2 Hz), 63.2 (—OCH$_2$, $^2J_{PC}$=7.7 Hz), 121.3 (—CF$_3$, q, $^1J_{FC}$=273.2 Hz), 125.5 (=CH), 129.5 (=CH, $^3J_{PC}$=6.6 Hz), 129.6 (=C, dq, $^2J_{FC}$=33.2 Hz, $^5J_{PC}$=2.2 Hz), 140.8 (=C, $^2J_{PC}$=7.7 Hz), 172.5 (N—C=O);

$^{31}$P NMR (121.50 MHz, CDCl$_3$) δ 26.6, 28.7 (minor, major);

(ESI-MS): Calculated for C$_{16}$H$_{23}$F$_3$NO$_5$P ([M]+H$^+$) 398.13443. Found 398.13310.

Diethyl 3-[N-acetyl,N-(hydroxy)amino]-1-(4-cyanophenyl)-propylphosphonate (113b)

The title compound was obtained as a colorless oil in 63% yield according to the same procedure as 113a but stating from compound 112b. The compound characterized as follows:

R$_f$ 0.38 (CH$_2$Cl$_2$/acetone: 1/1);

$^1$H NMR (300.13 MHz, CDCl$_3$) δ 1.09-1.31 (6H, m), 2.32 (3H, s), 2.16-2.65 (2H, m), 3.07 (1H, ddd, J=22.9, 7.4 and 5.7 Hz), 3.37 (1H, dt, J=13.8 and 5.3 Hz), 3.45-4.03 (5H, m), 7.12 (2H, minor, d, J=7.9 Hz), 7.16 (2H, minor, d, J=7.9 Hz), 7.41 (2H, major, d, J=7.9 Hz), 7.62 (2H, major, J=7.9 Hz), 9.49 (1H, br s);

$^{13}$C NMR (75.47 MHz, CDCl$_3$) δ 16.2 (—CH$_3$, $^3J_{PC}$=5.5 Hz), 20.6 (—CH$_3$, minor), 21.0 (—CH$_3$, major), 28.1 (—CH$_2$), 41.5 (P—CH, major, $^1J_{PC}$=136.6 Hz), 42.1 (P—CH, minor, $^1J_{PC}$=138.3 Hz), 62.6 (—OCH$_2$, $^2J_{PC}$=7.2 Hz), 63.0 (—OCH$_2$, $^2J_{PC}$=7.1 Hz), 112.7 (=C), 120.8 (—C≡N), 128.9 (=CH, minor, $^3J_{PC}$=6.6 Hz), 129.4 (=CH, minor, $^4J_{PC}$=1.7 Hz), 129.9 (=CH, major, $^3J_{PC}$=6.6 Hz), 132.2 (=CH, $^4J_{PC}$=1.7 Hz), 137.0 (=C, $^2J_{PC}$=2.7 Hz), 172.3 (N—C=O);

$^{31}$P NMR (121.50 MHz, CDCl$_3$) δ 28.1, 30.2 (minor, major);

ESMS m/z 355 ([M]+H$^+$).

Diethyl 3-[N-acetyl, N-(hydroxy)amino]-1-(4-carbamoylphenyl)-propyl-phosphonate (113c)

The title compound was obtained as a grey oil in 43% yield according to the same procedure as 113a but starting from compound 112c and after stirring of the reaction mixture for 2 days. The compound characterized as follows:

R$_f$ 0.10 (CH$_2$Cl$_2$/MeOH: 97/3);

$^1$H NMR (300.13 MHz, CDCl$_3$) δ 1.13 (3H, t, J=7.1 Hz), 1.23 (3H, t, J=7.0 Hz), 2.04 (3H, s), 3.14 (1H, ddd, J=22.9, 9.1 and 4.1 Hz), 3.28-4.04 (6H, m), 6.16 (1H, br s), 7.04 (1H, br s), 7.31 (2H, d, J=7.0 Hz), 7.75 (2H, d, J=7.9 Hz), 9.54 (1H, br s);

$^{13}$C NMR (75.47 MHz, CDCl$_3$) δ 16.2 (—CH$_3$, $^3J_{PC}$=5.5 Hz), 16.3 (—CH$_3$, $^3J_{PC}$=5.4 Hz), 20.4 (—CH$_3$), 27.2 (—CH$_2$, $^2J_{PC}$=2.2 Hz), 41.8 (P—CH, $^1J_{PC}$=137.8 Hz), 45.9 (—NCH$_2$, $^3J_{PC}$=14.2 Hz), 62.8 (—OCH$_2$, $^2J_{PC}$=7.1 Hz), 127.8 (=CH), 129.3 (=CH, $^3J_{PC}$=6.0 Hz), 132.5 (=C, $^5J_{PC}$=2.2 Hz), 140.0 (=C, $^2J_{PC}$=7.7 Hz), 169.6 (N—C=O), 172.2 (N—C=O);

$^{31}$P NMR (121.50 MHz, CDCl$_3$) δ 28.1, 26.8 (major/minor);

ESMS m/z 373 ([M]+H$^+$).

Diethyl 3-[N-acetyl, N-(hydroxy)amino]-1-(4-sulfamoylphenyl)propyl-phosphonate (113d)

The title compound was obtained as grey oil in 72% yield according to the same procedure as 113a but starting from compound 112d and after stirring the reaction mixture for 2 days. The compound characterized as follows:

R$_f$ 0.17 (CH$_2$Cl$_2$/MeOH: 93:7);

$^1$H NMR (300.13 MHz, CDCl$_3$) δ 1.16-1.32 (6H, m), 2.09 (3H, minor, s), 2.16 (3H, major, s), 2.21-2.62 (2H, m), 3.13-3.24 (1H, m), 3.28-4.08 (6H, m), 5.29 (2H, minor, s), 5.41 (2H, major, s), 7.40 (2H, d, J=6.8 Hz), 7.84 (2H, d, J=7.5 Hz); 9.26 (1H, br s);

$^{13}$C NMR (75.47 MHz, CDCl$_3$) δ 15.4 (—CH$_3$, minor, $^3J_{PC}$=7.1 Hz), 15.5 (—CH$_3$, minor, $^3J_{PC}$=7.1 Hz), 16.2 (—CH$_3$, major, $^3J_{PC}$=7.1 Hz), 16.3 (—CH$_3$, major, $^3J_{PC}$=7.1 Hz), 19.4 (—CH$_3$, minor), 20.2 (—CH$_3$, major) 26.8 (—CH$_2$), 40.5 (P—CH, $^1J_{PC}$=135.1 Hz), 44.9 (—NCH$_2$, minor, $^3J_{PC}$=12.6 Hz), 45.4 (—NCH$_2$, major), 62.9 (—OCH$_2$, $^2J_{PC}$=7.1 Hz), 63.2 (—OCH$_2$, $^2J_{PC}$=7.1 Hz), 126.4 (=CH), 129.8 (=CH), 140.2 (=C, minor), 140.5 (=C, major), 141.7 (=C—SO$_2$), 172.2 (N—C=O); $^{31}$P NMR (121.50 MHz, CDCl$_3$) δ 27.1, 30.0 (minor/major).

ESMS m/z 409 ([M]+H$^+$).

Diethyl 3-[N-acetyl,N-(hydroxy)amino]-1-(3-aminophenyl)propylphosphonate (113i)

The title compound was obtained as grey oil in 90% yield according to the same procedure as 113a but starting from compound 112e and after stirring the reaction mixture overnight. The crude viscous grey oil was directly used in the subsequent reaction but first characterized as follows:

R$_f$ 0.31 (CH$_2$Cl$_2$/MeOH: 9/1);

$^1$H NMR (300.13 MHz, CDCl$_3$) δ 1.11 (3H, t, J=7.1 Hz), 1.24 (3H, t, J=7.0 Hz), 2.07 (3H, s), 2.27-2.49 (2H, m), 2.97 (1H, ddd, J=22.7, 8.5 and 4.9 Hz), 3.37 (1H, major, ddd, J=13.6, 7.7 and 5.4 Hz), 3.45-3.56 (1H, minor, m), 3.70-4.03 (5H, m), 6.55 (1H, d, J=7.5 Hz), 6.62-6.64 (2H, m), 7.06 (1H, d, J=7.7 Hz), 9.55 (1H, br s);

$^{13}$C NMR (75.47 MHz, CDCl$_3$) δ 16.2 (—CH$_3$, major, $^3J_{PC}$=6.1 Hz), 16.3 (—CH$_3$, minor, $^3J_{PC}$=6.5 Hz), 20.5 (—CH$_3$), 27.7 (—CH$_2$), 40.9 (P—CH, major, $^1J_{PC}$=137.8 Hz), 42.0 (P—CH, minor, $^1J_{PC}$=138.1 Hz), 46.2 (—NCH$_2$, major, $^3J_{PC}$=14.3 Hz), 46.6 (—NCH$_2$, minor), 62.1 (—OCH$_2$, minor, $^2J_{PC}$=7.7 Hz), 62.4 (—OCH$_2$, major, $^2J_{PC}$=7.1 Hz), 62.9 (—OCH$_2$, minor, $^2J_{PC}$=6.6 Hz), 63.1 (—OCH$_2$, major, $^2J_{PC}$=7.7 Hz), 114.2 (=CH, $^5J_{PC}$=2.2 Hz), 115.4 (=CH, $^3J_{PC}$=6.6 Hz), 119.3 (=CH, $^3J_{PC}$=7.1 Hz), 129.5 (=CH), 136.8 (=C, $^2J_{PC}$=7.1 Hz), 146.8 (=C—N, $^4J_{PC}$=1.7 Hz), 172.1 (N—C=O);

$^{31}$P NMR (121.50 MHz, CDCl$_3$) δ 28.0, 29.5 (major, minor);

ESMS m/z found 345 ([M]+H$^+$), 367 ([M]+Na$^+$), 711 (2[M]+Na$^+$).

Diethyl 3-[N-acetyl, N-(hydroxy)amino]-1-(4-aminophenyl)propylphosphonate (113i)

The title compound was obtained as crude viscous grey oil in 96% yield according to the same procedure as 113a but starting from compound 112f and after stirring the reaction mixture overnight. The compound was directly used in the subsequent reaction but first characterized as follows:

R$_f$ 0.32 (CH$_2$Cl$_2$/MeOH: 9/1);

$^1$H NMR (300.13 MHz, CDCl$_3$) δ 1.08-1.28 (6H, m), 2.11 (3H, s), 1.99-2.58 (2H, m), 2.95-3.03 (1H, m), 3.35 (1H, app dt, J=13.6 and 5.1 Hz), 3.45-4.10 (5H, m), 6.62 (2H, d, J=7.9 Hz), 7.04-7.09 (2H, m);

$^{13}$C NMR (75.47 MHz, CDCl$_3$) δ 16.3 (—CH$_3$, $^3J_{PC}$=5.5 Hz), 20.6 (—CH$_3$), 28.1 (—CH$_2$, $^2J_{PC}$=1.1 Hz), 41.0 (P—CH, major, $^1J_{PC}$=137.6 Hz), 41.6 (P—CH, minor, $^1J_{PC}$=139.5 Hz), 46.4 (—NCH$_2$, $^3J_{PC}$=11.5 Hz), 61.9 (—OCH$_2$, minor, $^2J_{PC}$=7.1 Hz), 62.4 (—OCH$_2$, major, $^2J_{PC}$=7.1 Hz), 62.7 (—OCH$_2$, minor, $^2J_{PC}$=7.2 Hz), 62.9 (—OCH$_2$, major, $^2J_{PC}$=7.7 Hz), 115.3 (=CH), 125.7 (=C, $^2J_{PC}$=6.6 Hz), 129.9 (=CH, $^3J_{PC}$=7.7 Hz), 145.6 (=C—N, major, $^5J_{PC}$=2.2 Hz), 145.7 (=C—N, minor, $^5J_{PC}$=2.2 Hz), 172.3 (N—C=O);

$^{31}$P NMR (121.50 MHz, CDCl$_3$) δ 28.9, 30.4 (minor, major);

ESMS m/z 345 ([M]+H$^+$), 367 ([M]+Na$^+$), 711 (2[M]+Na$^+$).

Diethyl 3-[N-formyl,N-(hydroxy)amino]-1-(4-cyanophenyl)-propenylphosphonate (117)

The title compound was obtained as a colorless oil in 91% yield according to the same procedure as 113a but starting from compound 116. The compound characterized as follows:

R$_f$ 0.16 (hexane/acetone: 1/1);

$^1$H NMR (300.13 MHz, CDCl$_3$) δ 1.14 (3H, minor, t, J=7.1 Hz), 1.23 (6H, t, J=7.0 Hz), 1.27 (3H, major, t, J=7.1 Hz), 2.02-2.35 (2H, minor, m), 2.51-2.66 (2H, major, m), 3.11-3.24 (1H, m), 3.26-3.37 (1H, m), 3.61-3.53 (1H, minor, m), 3.78-4.11 (5H, m), 7.40 (2H, minor, dd, J=8.6 and 2.0 Hz), 7.43 (2H, major, dd, J=8.5 and 2.1 Hz), 7.61-7.65 (2H, m), 8.40 (1H, br s), 9.61 (1H, br s);

$^{13}$C NMR (75.47 MHz, CDCl$_3$) δ 16.2 (—CH$_3$, minor, $^3J_{PC}$=6.6 Hz), 16.3 (—CH$_3$, major, $^3J_{PC}$=6.6 Hz); 26.6 (—CH$_2$, minor, $^2J_{PC}$=1.6 Hz), 27.4 (—CH$_2$, major, $^2J_{PC}$=1.6 Hz), 41.2 (P—CH, minor, $^1J_{PC}$=138.9 Hz), 43.0 (P—CH, major, $^1J_{PC}$=137.8 Hz), 44.7 (—NCH$_2$, minor, $^3J_{PC}$=11.6 Hz); 46.8 (—NCH$_2$, major, $^3J_{PC}$=14.3 Hz), 62.6 (—OCH$_2$, minor, $^2J_{PC}$=7.1 Hz), 63.0 (—OCH$_2$, major, $^2J_{PC}$=6.6 Hz), 63.1 (—OCH$_2$, minor, $^2J_{PC}$=7.7 Hz), 63.3 (—OCH$_2$, major, $^2J_{PC}$=7.7 Hz), 111.4 (=C, minor, $^5J_{PC}$=2.7 Hz), 111.7 (=C, major, $^5J_{PC}$=3.8 Hz), 118.3 (—C≡N, minor), 118.5 (—C≡N, major), 130.0 (=CH, $^3J_{PC}$=6.6 Hz), 132.2 (=CH, minor, $^4J_{PC}$=2.2 Hz), 132.5 (=CH, major, $^4J_{PC}$=2.2 Hz), 140.9 (=C, minor, $^2J_{PC}$=7.1 Hz), 141.9 (=C, major, $^2J_{PC}$=7.7 Hz), 156.2 (N—C=O, minor), 163.2 (N—C=O, major);

$^{31}$P NMR (121.50 MHz, CDCl$_3$) δ 26.1, 28.1 (minor, major);

ESMS m/z found 341 ([M]+H$^+$), 363 ([M]+Na$^+$).

Diethyl 3-[N-acetyl,N-(benzyloxy)amino]-1-thiophen-2-yl-propylphosphonate (114g)

The title compound was obtained as a thick gray oil in 50% yield according to the same procedure as 113a but starting from compound 112g and using 1.2 eq of 10% Pd/C. The compound characterized as follows:

$R_f$ 0.44 (pentane/acetone: 1/1);

$^1$H NMR (300.13 MHz, CDCl$_3$) δ 1.15 (3H, t, J=7.0 Hz), 1.26 (3H, t, J=7.2 Hz), 2.03 (3H, s), 2.12-2.26 (1H, m), 2.40-2.54 (1H, m), 3.39 (1H, ddd, J=22.9, 11.3 and 3.7 Hz), 3.52 (1H, ddd, J=14.3, 8.5 and 4.9 Hz), 3.66-3.73 (1H, m), 3.77-4.12 (4H, m), 4.71 (1H, br s), 4.81 (1H, br s), 6.95-7.00 (2H, m), 7.20-7.23 (1H, m), 7.29-7.27 (5H, m);

$^{13}$C NMR (75.47 MHz, CDCl$_3$) δ 16.3 (—CH$_3$, $^3J_{PC}$=6.0 Hz), 16.4 (—CH$_3$, $^3J_{PC}$=6.0 Hz), 20.5 (—CH$_3$), 28.5 (—CH$_2$, $^2J_{PC}$=1.7 Hz), 33.6 (P—CH, minor, $^1J_{PC}$=139.8 Hz), 37.5 (P—CH, major, $^1J_{PC}$=143.8 Hz), 43.7 (—NCH$_2$), 61.5 (—OCH$_2$, $^2J_{PC}$=6.6 Hz, major), 61.6 (—OCH$_2$, $^2J_{PC}$=6.6 Hz, minor), 62.3 (—OCH$_2$, $^2J_{PC}$=7.1 Hz, major), 62.9 (—OCH$_2$, $^2J_{PC}$=7.1 Hz, minor), 76.2 (—OCH$_2$, major), 76.4 (—OCH$_2$, minor), 124.8 (=CH, $^5J_{PC}$=2.8 Hz), 126.9 (=CH $^{13}J_{PC}$=3.3 Hz), 127.0 (=CH, $^4J_{PC}$=8.2 Hz), 128.7 (=CH), 128.9 (=CH), 129.2 (=CH), 134.4 (=CH), 137.4 (=C, $^2J_{PC}$=8.8 Hz), 171.2 (N—C=O);

$^{31}$P NMR (121.50 MHz, CDCl$_3$) δ 25.9;

ESMS m/z 426 ([M]+H$^+$).

Diethyl 3-[N-acetyl,N-(benzyloxy)-amino]-1-thiophen-3-yl-propylphosphonate (114h)

The title compound was obtained as a thick gray oil in 65% yield according to the same procedure as 113a but starting from compound 112h and using 1.2 eq of 10% Pd/C. The compound characterized as follows:

$R_f$ 0.20 (CH$_2$Cl$_2$/MeOH: 96/4);

$^1$H NMR (300.13 MHz, CDCl$_3$) δ 1.11 (3H, t, J=7.1 Hz), 1.24 (3H, s, J=7.1 Hz), 2.02 (3H, s) 2.10-2.25 (1H, m), 2.34-2.48 (1H, m), 3.22 (1H, ddd, J=22.6, 11.4 and 3.8 Hz), 3.49 (1H, ddd, J=14.3, 8.3 and 4.8 Hz), 3.57-3.66 (1H, m), 3.67-4.09 (4H, m), 4.71-4.83 (2H, m), 7.07-7.09 (1H, m), 7.14-7.16 (1H, m), 7.27-7.37 (6H, m);

$^{13}$C NMR (75.47 MHz, CDCl$_3$) δ 16.3 (—CH$_3$, $^3J_{PC}$=6.0 Hz), 16.4 (—CH$_3$, $^3J_{PC}$=6.0 Hz), 20.5 (—CH$_3$), 27.2 (—CH$_2$, $^2J_{PC}$=2.2 Hz), 36.6 (P—CH, $^1J_{PC}$=141.6 Hz), 43.8 (—NCH$_2$), 62.0 (—OCH$_2$, $^2J_{PC}$=7.1 Hz), 62.6 (—OCH$_2$, $^2J_{PC}$=7.1 Hz), 76.3 (—OCH$_2$), 123.3 (=CH, $^4J_{PC}$=9.9 Hz), 125.7 (=CH, $^3J_{PC}$=1.1 Hz), 128.1 (=CH, $^3J_{PC}$=3.9 Hz), 128.7 (=CH), 128.9 (=CH), 129.2 (=CH), 134.3 (=C), 135.2 (=C, $^2J_{PC}$=7.1 Hz), 173.2 (N—C=O);

$^{31}$P NMR (121.50 MHz, CDCl$_3$) δ 27.3;

ESMS m/z 426 ([M]+H$^+$).

Diethyl 3-[N-acetyl,N-(hydroxy)amino]-1-(thien-2-yl)-propylphosphonate (113g)

A 1 M solution of Boron trichloride (BCl$_3$) in hexanes (1.6 mL, 1.60 mmol) was added dropwise to a stirred solution of 114g (169 mg, 0.397 mmol) in dry CH$_2$Cl$_2$ at –50° C. After stirring for 30 min at –50° C., the reaction was quenched with saturated NaHCO$_3$ in water (10 mL) and the reaction mixture was allowed to warm to room temperature. The aqueous layer was extracted with CH$_2$Cl$_2$. The pooled organic layers were dried on anhydrous MgSO$_4$, filtered and the solvents were removed under reduced pressure. The residual oil was purified by column chromatography using CH$_2$Cl$_2$/MeOH (in a volume ratio of 94/6) yielding a thick grey oil (69%). The product was characterized as follows:

$R_f$ 0.19 (CH$_2$Cl$_2$/Acetone: 1/1);

$^1$H NMR (300.13 MHz, CDCl$_3$) δ 1.15-1.34 (6H, m), 2.14 (3H, s) 2.17-2.60 (2H, m), 3.46 (1H, dt, J=22.8 and 5.3 Hz), 3.61-4.12 (6H, m), 6.95-7.02 (2H, m), 7.20-7.22 (1H, m), 9.42 (1H, br s);

$^{13}$C NMR (75.47 MHz, CDCl$_3$) δ 16.3 (—CH$_3$, $^3J_{PC}$=5.4 Hz), 20.6 (—CH$_3$), 29.6 (—CH$_2$, major, $^2J_{PC}$=3.3 Hz), 29.7 (—CH$_2$, minor, $^2J_{PC}$=3.3 Hz), 37.1 (P—CH, $^1J_{PC}$=142.2 Hz), 46.3 (—NCH$_2$), 62.9 (—OCH$_2$, $^2J_{PC}$=6.0 Hz), 63.4 (—OCH$_2$, $^2J_{PC}$=7.7 Hz), 124.9 (=CH), 127.0 (=CH, $^4J_{PC}$=7.5 Hz), 127.2 (=CH), 138.1 (=C), 172.5 (N—C=O);

$^{31}$P NMR (121.50 MHz, CDCl$_3$) δ 25.6, 28.0 (minor, major);

(ESI-MS): Calculated for C$_{13}$H$_{22}$NO$_5$PS ([M]+Na$^+$) 358.08540. Found 358.08417.

Diethyl 3-[N-acetyl,N-(hydroxy)amino]-1-thiophen-3-yl-propylphosphonate (113h)

The title compound was obtained as a thick gray oil in 86% yield according to the same procedure as 113g but starting from compound 114h. The compound characterized as follows:

$R_f$ 0.22 (CH$_2$Cl$_2$/acetone: 1/1);

$^1$H NMR (300.13 MHz, CDCl$_3$) δ 1.12-1.30 (6H, m), 2.09 (3H, s), 2.19-2.58 (2H, m), 3.27 (1H, ddd, J=22.8, 8.7 and 4.7 Hz), 3.36-3.61 (2H, m), 3.74-4.15 (4H, m), 7.03-7.04 (1H, m), 7.15-7.17 (1H, m), 7.24-7.26 (1H, m), 9.59 (1H, br s);

$^{13}$C NMR (75.47 MHz, CDCl$_3$) δ 16.2 (—CH$_3$, $^3J_{PC}$=5.5 Hz), 16.2 (—CH$_3$, $^3J_{PC}$=5.5 Hz), 20.5 (—CH$_3$), 27.3 (—CH$_2$, minor), 27.8 (—CH$_2$, major), 36.4 (P—CH, minor, $^1J_{PC}$=141.6 Hz) 37.1 (P—CH, major, $^1J_{PC}$=140.5 Hz), 46.1 (—NCH$_2$, major, $^3J_{PC}$=13.2 Hz), 46.7 (—NCH$_2$, minor, $^3J_{PC}$=14.5 Hz), 62.5 (—OCH$_2$, $^2J_{PC}$=7.7 Hz), 63.0 (—OCH$_2$, $^2J_{PC}$=7.2 Hz), 123.2 (=CH, $J_{PC}$=9.9 Hz), 125.8 (=CH), 127.9 (=CH, $J_{PC}$=4.4 Hz), 135.5 (=C, $J_{PC}$=7.7 Hz), 172.2 (N—C=O);

$^{31}$P NMR (121.50 MHz, CDCl$_3$) δ 27.4, 28.8 (minor, major);

ESMS m/z found 336 ([M]+H$^+$), 358 ([M]+Na$^+$).

3-[N-acetyl. N-(hydroxy)amino]-1-(4-trifluoromethylphenyl)-propylphosphonic acid (103a)

To a solution of diethyl 3-[N-acetyl,N-(hydroxy)amino]-1-(4-trifluoromethyl-phenyl)-propylphosphonate (113a) (150 mg, 0.377 mmol) in dry MeCN (3.8 mL) was added dropwise trimethylsilyl bromide (TMSBr; 497 μL, 3.77 mmol) at room temperature and the mixture was stirred for another 2 days at that temperature. The solvents were removed under reduced pressure and the traces of TMSBr were removed under high vacuum (0.05 mbar) overnight. The residual oil was dissolved in 2 mL distilled water and lyophilised. The resulting solid was purified by reversed phase HPLC using a 5 mM NH$_4$OAc solution for 5 min followed by a gradient elution of 5 mM NH$_4$OAc solution to MeCN in 15 min. The appropriate fractions were lyophilised, yielding 23 mg of a colorless hygroscopic solid (23%). The product was characterized as follows:

$^1$H NMR (300.13 MHz, D$_2$O) δ 1.75 (3H, minor, s), 2.01 (3H, major, s), 2.25-2.61 (2H, m), 3.00-3.18 (1H, m), 3.43-3.67 (2H, m), 7.46-7.64 (2H, m), 7.66-7.84 (2H, m);

$^{13}$C NMR (75.47 MHz, CDCl$_3$) δ: 19.3 (—CH$_3$), 26.7 (—CH$_3$, major), 26.9 (—CH$_3$, minor), 43.5 (P—CH, minor, $^1J_{PC}$=131.1 Hz), 44.2 (P—CH, major, $^1J_{PC}$=130.0 Hz), 46.3 (—NCH$_2$, $^3J_{PC}$=17.6 Hz), 121.9 (—CF$_3$, q, $^1J_{FC}$=271.1 Hz) 125.3 (=CH, major), 125.6 (=CH, minor), 128.1 (=C, dq, $^2J_{FC}$=31.8 Hz, $^5J_{PC}$=3.3 Hz), 129.6 (=CH, $^3J_{PC}$=5.5 Hz), 142.8 (=C, minor), 143.0 (=C, major, $^2J_{PC}$=7.2 Hz), 173.7 (N—C=O, major)? 173.8 (N—C=O, minor);

$^{31}$P NMR (121.50 MHz, D$_2$O) δ 21.5;

(ESI-MS): Calculated for $C_{12}H_{15}F_3NO_5P$ ([M]-H$^+$) 340.05617. Found 340.05641.

3-[N-acetyl,N-(hydroxy)amino]-1-(4-sulfamoylphenyl)propylphosphonic acid (103d)

The title compound was obtained as pale yellow hygroscopic solid in 36% yield according to the same procedure as 103a but starting from compound 113d. The compound characterized as follows:

$^1$H NMR (300.13 MHz, D$_2$O) δ 1.74 (3H, minor, s), 1.99 (3H, major, s), 2.27-2.38 (2H, m), 3.03-3.14 (1H, m), 3.52-3.78 (2H, m), 7.51-7.65 (2H, m), 7.83-7.97 (2H, m);

$^{13}$C NMR (75.47 MHz, D$_2$O) δ 19.2 (—CH$_3$), 26.8 (—CH$_2$), 44.5 (P—CH, $^1J_{PC}$=127.3 Hz), 46.4 (—NCH$_2$, $^3J_{PC}$=17.1 Hz), 125.9 (=CH, major), 126.1 (=CH, minor), 130.1 (=CH, $^3J_{PC}$=5.4 Hz), 139.1 (=C—SO$_2$, $^5J_{PC}$=2.8 Hz), 145.0 (=C, $^2J_{PC}$=6.2 Hz), 173.6 (N—C=O);

$^{31}$P NMR (121.50 MHz, D$_2$O) δ 20.6;

ESMS m/z found 351 ([M]-H$^+$), 703 (2[M]-H$^+$).

3-[N-acetyl. N-(hydroxy)amino]-1-(3-aminophenyl) propylphosphonic acid (103i)

The title compound was obtained as an amber hygroscopic solid in 37% yield according to the same procedure as 103a but starting from compound 113i. The compound characterized as follows:

$^1$H NMR (300.13 MHz, D$_2$O) δ 1.74 (3H, major, s), 2.04 (3H, minor, s), 2.15-2.52 (2H, m), 2.94 (1H, ddd, J=22.0, 12.0 and 2.8 Hz), 3.41-3.47 (1H, m), 3.56-3.66 (1H, m), 6.91 (3H, m), 7.29 (1H, t, J=7.4 Hz);

$^{13}$C NMR (75.47 MHz, D$_2$O) δ 21.8 (—CH$_3$), 29.3 (—CH$_2$), 46.4 (P—CH, $^1J_{PC}$=130.2 Hz), 48.8 (—NCH$_2$, $^3J_{PC}$=48.8 Hz), 118.6 (=CH, minor, $J_{PC}$=2.7 Hz), 119.3 (=CH, major, $J_{PC}$=2.8 Hz), 121.1 (=CH, minor, $J_{PC}$=5.0 Hz), 121.7 (=CH, major, $J_{PC}$=6.0 Hz), 125.1 (=CH, minor, $J_{PC}$=6.0 Hz), 126.1 (=CH, major, $J_{PC}$=6.1 Hz), 132.1 (=CH, major, $J_{PC}$=1.6 Hz), 132.2 (=CH, minor, $J_{PC}$=3.9 Hz), 142.7 (=C, $^2J_{PC}$=7.1 Hz), 143.3 (=C), 176.2 (N—C=O);

$^{31}$P NMR (121.50 MHz, D$_2$O) δ 24.5;

ESMS m/z found 287 ([M]-H$^+$), 575 (2[M]-H$^+$).

3-[N-acetyl,N-(hydroxy)amino]-1-(4-aminophenyl) propylphosphonic acid (103i)

The title compound was obtained as an amber hygroscopic solid in 28% yield according to the same procedure as 103a but starting from compound 113j. The compound characterized as follows:

$^1$H NMR (300.13 MHz, D$_2$O) δ 2.05 (3H, s), 2.14-2.51 (2H, m), 2.82-2.96 (1H, m), 3.45-3.62 (2H, m), 7.03-7.28 (4H, m);

$^{13}$C NMR (75.47 MHz, D$_2$O) δ 19.3 (—CH$_3$), 26.8 (—CH$_2$), 43.3 (P—CH, $^1J_{PC}$=131.2 Hz), 46.6 (—NCH$_2$, $^3J_{PC}$=17.3 Hz), 118.9 (=CH), 130.2 (=CH, $^3J_{PC}$=4.9 Hz), 133.2 (=C), 138.7 (=C), 173.7 (N—C=O, major), 173.9 (N—C=O, minor);

$^{31}$P NMR (121.50 MHz, D$_2$O) δ 22.6;

ESMS m/z found 287 ([M]-H$^+$), 575 (2[M]-H$^+$).

Bisammonium 3-[N-acetyl. N-(hydroxy)amino]-1-(4-cyanophenyl)-propylphosphonate (104b)

To a solution of 113b (130 mg, 0.367 mmol) in dry MeCN (3.7 mL) was added dropwise TMSBr (484 μL, 3.67 mmol) at room temperature and the mixture was stirred for another 24 hours. The solvents were removed under reduced pressure and the traces of TMSBr were removed under high vacuum (0.05 mbar) overnight. The residual oil was dissolved in 2 mL of Type I water and the pH of the mixture was adjusted to 8-9 with a 5% NH$_4$OH solution. The solution was lyophilized and the residual solid was purified by column chromatography using Whatman CF11 cellulose and a mixture of MeCN/NH$_4$OH (aqueous, 1 M) (in a volume ratio of 3/1). The different eluted fractions were spotted on cellulose TLC and the spots were visualised under UV-light (365 nm) after dipping the TLC plate in a pinacryptol yellow solution (0.1% in H$_2$O) and drying the plate under a stream of hot air (dark-blue spots on light-blue fluorescent background). The appropriate fractions were lyophilised, yielding 79 mg of a pale amber hygroscopic solid (66%). The product was characterized as follows:

R$_f$ 0.33 (cellulose TLC, MeCN/NH$_4$OH$_{(aq, 1M)}$: 3/1);

$^1$H NMR (300.13 MHz, D$_2$O) δ 1.64 (3H, minor, s), 1.90 (3H, major, s), 2.12-2.49 (2H, m), 2.94 (1H, ddd, J=22.0, 12.1 and 2.8 Hz), 3.35 (1H, app dt, J=14.4 and 5.7 Hz), 3.50 (1H, ddd, J=14.4, 8.4 and 6.1 Hz), 7.39 (2H, dd, J=8.3 and 1.7 Hz), 7.65 (2H, d, J=8.2 Hz);

$^{13}$C NMR (75.47 MHz, D$_2$O) δ 19.1 (—CH$_3$, major), 19.3 (—CH$_3$, minor), 26.5 (—CH$_2$, major), 26.7 (—CH$_2$, minor), 44.0 (P—CH, minor, $^1J_{PC}$=126.8 Hz), 44.5 (P—CH, major, $^1J_{PC}$=127.4 Hz), 46.1 (—NCH$_2$, major, $^3J_{PC}$=17.1 Hz), 49.6 (—NCH$_2$, minor, $^3J_{PC}$=17.0 Hz), 108.8 (=C, $^5J_{PC}$=3.3 Hz), 120.0 (—C≡N), 129.8 (=CH, $^3J_{PC}$=6.1 Hz), 132.3 (=CH, major, $^4J_{PC}$=2.2 Hz), 132.6 (=CH, minor, $^4J_{PC}$=1.6 Hz), 145.1 (=C, $^2J_{PC}$=7.2 Hz), 173.6 (N—C=O);

$^{31}$P NMR (121.50 MHz, D$_2$O) δ 20.0, 20.5 (minor, major)

(ESI-MS): Calculated for $C_{12}H_{21}N_4O_5P$ ([M]−2(NH$_4^+$)+H$^+$) 297.06403. Found 297.06454.

Bisammonium 3-[N-acetyl,N-(hydroxy)amino]-1-(4-carbamoylphenyl) propylphosphonic acid (104c)

The title compound was obtained as a pale yellow hygroscopic solid in 73% yield according to the same procedure as 104b but starting from compound 113c. The compound characterized as follows:

R$_f$ 0.25 (MeCN/NH$_4$OH$_{(aq, 1M)}$: 3/1);

$^1$H NMR (300.13 MHz, D$_2$O) δ 1.59 (3H, minor, s), 1.88 (3H, major, s), 2.27-2.62 (2H, m), 2.89-3.05 (1H, m), 3.28-3.60 (2H, m), 7.36 (2H, br s), 7.70 (2H, br s);

$^{13}$C NMR (75.47 MHz, D$_2$O) δ 19.1 (—CH$_3$), 26.6 (—CH$_2$), 44.2 (P—CH, $^1J_{PC}$=129.5 Hz), 46.2 (—NCH$_2$, $^3J_{PC}$=17.5 Hz), 127.5 (=CH, major), 127.8 (=CH, minor, $^4J_{PC}$=2.2 Hz), 129.4 (=CH, $^3J_{PC}$=5.9 Hz), 130.8 (=C, major), 131.0 (=C, minor), 143.6 (=C, $^2J_{PC}$=6.6 Hz), 173.1 (N—C=O), 173.6 (N—C=O);

$^{31}$P NMR (121.50 MHz, D$_2$O) δ 21.2;

ESMS m/z found 315 ([M]−2(NH$_4^+$)+H$^+$), 631 (2[M]−4(NH$_4^+$)+3H$^+$).

Bisammonium 3-[N-acetyl,N-(hydroxy)amino]-1-thiophen-2-yl-propylphosphonate (104g)

The title compound was obtained as a pale amber hygroscopic solid in 62% yield according to the same procedure as 104b but starting from compound 113g. The compound characterized as follows:

R$_f$ 0.33 (cellulose TLC, MeCN/NH$_4$OH$_{(aq, 1M)}$: 3/1);

$^1$H NMR (300.13 MHz, D$_2$O) δ 1.76 (3H, minor, s), 2.09 (3H, major, s), 1.93-2.51 (2H, m), 3.17 (1H, ddd, J=21.7, 12.1 and 2.6 Hz), 3.32-3.42 (1H, m), 3.64 (1H, ddd, J=14.4, 8.0 and 6.7 Hz), 6.89 (1H, app dt, J=3.3 and 1.0 Hz), 6.96 (1H, dd, J=5.2 and 3.5 Hz), 7.25 (1H, app dt, J=5.3 and 1.2 Hz);

$^{13}$C NMR (75.47 MHz, D$_2$O) δ 19.3 (—CH$_3$, major), 19.4 (—CH$_3$, minor), 28.7 (—CH$_2$, major), 28.7 (—CH$_2$, minor), 38.6 (P—CH, minor, $^1J_{PC}$=134.0 Hz), 39.1 (P—CH, major, $^1J_{PC}$=134.5 Hz), 46.1 (—NCH$_2$, major, $^3J_{PC}$=16.5 Hz), 49.6 (—NCH$_2$, minor, $^3J_{PC}$=17.6 Hz), 124.3 (=CH, minor, J$_{PC}$=3.3 Hz), 124.5 (=CH, minor), 126.3 (=CH, major, J$_{PC}$=8.3 Hz), 126.5 (=CH, minor), 126.9 (=CH, major, $^4J_{PC}$=2.7 Hz), 127.1 (=CH, minor), 141.3 (=C, $^2J_{PC}$=8.8 Hz), 169.8 (N—C=O, minor), 173.8 (N—C=O, major);

$^{31}$P NMR (121.50 MHz, D$_2$O) δ 20.3, 20.8 (minor/major);

ESMS m/z found 278 ([M]−2(NH$_4^+$)+H$^+$), 557 (2[M]−4 (NH$_4^+$)+3H$^+$).

Bisammonium 3-[N-acetyl. N-(hydroxy)amino]-1-thiophen-3-yl-propylphosphonate (104h)

The title compound was obtained as a pale amber hygroscopic solid in 78% yield according to the same procedure as 104b but starting from compound 113h. The compound characterized as follows:

R$_f$ 0.33 (cellulose TLC, MeCN/NH$_4$OH$_{(aq, 1\,M)}$: 3/1);

$^1$H NMR (300.13 MHz, D$_2$O) δ 11.69 (3H, minor, s), 1.98 (3H, major, s), 2.01-2.43 (2H, m), 3.04 (1H, ddd, J=21.6, 12.2 and 2.9 Hz), 3.38 (1H, dt, J=14.3 and 6.0 Hz), 3.60 (1H, ddd, J=14.5, 7.8 and 6.8 Hz), 7.03-7.13 (2H, m), 7.33 (1H, ddd, J=9.9, 4.9 and 3.1 Hz);

$^{13}$C NMR (75.47 MHz, D$_2$O) δ 19.3 (—CH$_3$), 27.2 (—CH$_2$), 38.6 (P—CH, minor, $^1J_{PC}$=132.3 Hz), 39.1 (P—CH, major, $^1J_{PC}$=132.8 Hz), 46.3 (—NCH$_2$, major, $^3J_{PC}$=17.0 Hz), 49.7 (—NCH$_2$, minor, $^3J_{PC}$=17.1 Hz), 122.3 (=CH, $^4J_{PC}$=8.8 Hz), 125.4 (=CH, major), 125.9 (=CH, minor), 128.3 (=CH, $^3J_{PC}$=3.8 Hz), 138.3 (=C, minor, $^2J_{PC}$=7.1 Hz), 138.6 (=C, major, $^2J_{PC}$=7.6 Hz), 173.7 (N—C=O);

$^{31}$P NMR (121.50 MHz, D$_2$O) δ 21.9;

ESMS m/z found: 278 ([M]−2(NH$_4^+$)+H$^+$), 557 (2[M]−4 (NH$_4^+$)+3H$^+$).

3-[N-formyl,N-(hydroxy)amino]-1-(4-cyanophenyl)-propylphosphonic acid (105)

The title compound was obtained as a colorless amorphous solid in 82% yield according to the same procedure as 104b but starting from compound 113j. The compound characterized as follows:

R$_f$ 0.19 (Cellulose TLC, MeCN/NH$_4$OH$_{(aq, 1\,M)}$: 4/1);

$^1$H NMR (300.13 MHz, D$_2$O) δ 2.10-2.47 (2H, m), 2.89-2.99 (1H, m), 3.19-3.48 (2H, m), 7.38-7.39 (2H, m), 7.63-7.65 (2H, m), 8.08 (1H, br s);

$^{13}$C NMR (75.47 MHz, D$_2$O) δ 26.4 (—CH$_2$, major), 26.5 (—CH$_2$, minor), 44.0 (P—CH, major, $^1J_{PC}$=126.8 Hz), 44.1 (P—CH, $^1J_{PC}$=129.5 Hz), 44.7 (—NCH$_2$, minor, $^3J_{PC}$=16.4 Hz), 48.9 (—NCH$_2$, major), 108.9 (=C, minor, $^5J_{PC}$=2.8 Hz), 109.1 (=C, major, $^5J_{PC}$=2.8 Hz), 120.0 (—C=N), 129.7 (=CH, major, $^3J_{PC}$=5.5 Hz), 129.9 (=CH, minor, $^3J_{PC}$=5.5 Hz), 132.4 (=CH, minor), 132.6 (=CH, major), 144.7 (=C, major, $^2J_{PC}$=6.6 Hz), 145.0 (=C, minor, $^2J_{PC}$=6.6 Hz), 159.5 (N—C=O, minor), 163.6 (N—C=O, major), $^{31}$P NMR (121.50 MHz, D$_2$O) δ 19.93;

ESMS m/z found: 283 ([M]−2(NH$_4^+$)+H$^+$), 567 (2[M]−4 (NH$_4^+$)+3H$^+$).

EXAMPLE 2

Biological Evaluation of α-Phenyl Phosphonic Acid Derivatives

The in vitro anti-malarial activity of some of the compounds prepared in example 1 was determined as follows. Intraerythrocytic stages of the *Plasmodium falciparum* strains 3D7 and Dd2 were respectively incubated with serial dilutions of the relevant compounds and the viability of the parasites was assessed by their ability to incorporate [$^3$H] hypoxanthine into DNA. Inhibition results were expressed as IC$_{50}$. Fosmidomycin and FR900098 were included in this experimental procedure as reference compounds.

The tested compounds significantly surpassed the activity of fosmidomycin in the inhibition of parasite growth, as shown in the following table.

Compound 1e emerged as a very promising anti-malarial drug in this series. Its in vitro antimalarial activity indicated that it is twelve-fold more active than fosmidomycin and also exceeds the activity of FR900098, the most potent analogue known to date. Apparently, the lipophilic and electronegative properties of the 3,4-dichloro-substitution pattern on the phenyl ring of compound 1e selectively favours the interaction with the target.

TABLE

| compound | R | R$_1$ | R$_2$ | IC$_{50}$ (μM) Dd2 | IC$_{50}$ (μM) 3D7 |
|---|---|---|---|---|---|
| 1c | 4-OMe | H | OH | 0.20 | 0.36 |
| 2d | 4-Cl | CH$_3$ | OH | 0.095 | 0.35 |
| 1e | 3,4-Cl$_2$ | H | OH | 0.028 | 0.09 |
| 2e | 3,4-Cl$_2$ | CH$_3$ | OH | 0.090 | 0.25 |
| fosmidomycin | | | | 0.36 | 1.1 |
| FR900098 | | | | 0.18 | 0.32 |

Compounds 104b and 105 have been tested under the same conditions within a similar experimental setup in the Dd2 cell line. Both compounds exhibited substantial higher activity in the Dd2 cell line with respect to the reference compounds fosmidomycin and FR900098. Compounds 103a, d, i, j and 104c-d, g, h are also tested according to this protocol and exhibit similar activities.

The invention claimed is:

1. A phosphonic acid compound having the structural formula:

(II)

wherein:
- R$_1$ is selected from the group consisting of hydrogen, C$_{1-7}$ alkyl, C$_{3-10}$ cycloalkyl, aryl, arylalkyl and heterocyclic,
- R$_2$ is selected from the group consisting of hydroxy and hydroxy-protecting groups, and
- Het is 5- or 6-membered heteroaromatic ring which comprises 1, 2 or 3 heteroatoms independently selected from the group consisting of O, N and S; wherein said heteroaromatic ring is optionally substituted with 1 to 3 substituents independently selected from the group consisting of hydrogen, halogen, hydroxy, $C_{1-4}$ alkyl, $C_{1-4}$ alkoxy, nitroso, nitro, amino, trifluoromethyl and cyano; and a stereoisomer thereof, a solvate thereof, or a salt thereof.

2. 3-(N-hydroxyacetamido)-1-(3,4-dichlorophenyl)propylphosphonic acid.

3. A phosphonic acid compound according to claim 1, wherein $R_1$ is methyl or hydrogen.

4. A phosphonic acid compound according to claim 1, wherein $R_1$ is selected from the group consisting of phenyl, benzyl, p-toluyl, 1-naphthyl, 2-naphthyl, 4-morpholinyl, 1-piperidinyl, 1-imidazolidinyl, 1-pyrrolidinyl, 2-thiazolyl, 1-methyl-1H-pyrrole-2-yl, 2-furanyl, 3-furanyl, 3-pyridinyl, 4-pyridinyl, 2-thienyl, 3-thienyl, cyclopropyl, cyclobutyl, cyclopentyl, cyclohexyl, 1-adamantyl, and 2-norbornyl.

5. A phosphonic acid compound according to claim 1, being bisammonium 3-[N-acetyl,N-(hydroxy)amino]-1-thiophen-2-yl)-propylphosphonic acid.

6. Bisammonium 3-[N-acetyl,N-(hydroxy)amino]-1-thiophen-3-yl-propylphosphonate.

7. A non-toxic base addition salt of a phosphonic acid compound according to any of claims 1 to 5.

8. A biologically-active composition comprising a biologically effective amount of a compound according to any of claims 1 to 6, and optionally one or more carriers.

9. A biologically-active composition according to claim 8, further comprising an effective amount of one or more antiparasitic agents.

10. A method of treatment of an infectious disease in a patient, comprising the administration of a therapeutically effective amount of a compound according to claim 1, and optionally an effective amount of one or more anti-infectious agents.

11. A method of treatment of an infectious disease in a patient, comprising the administration of a therapeutically effective amount of a compound according to claim 2, and optionally an effective amount of one or more anti-infectious agents.

12. A method of treatment of an infectious disease in a patient, comprising the administration of a therapeutically effective amount of a compound according to claim 6, and optionally an effective amount of one or more anti-infectious agents.

13. A method of treatment of a parasitic disease in a patient, comprising the administration of a therapeutically effective amount of a compound according to claim 1, and optionally an effective amount of one or more anti-infectious agents.

14. A method of treatment of a parasitic disease in a patient, comprising the administration of a therapeutically effective amount of a compound according to claim 2, and optionally an effective amount of one or more anti-infectious agents.

15. A method of treatment of a parasitic disease in a patient, comprising the administration of a therapeutically effective amount of a compound according to claim 6, and optionally an effective amount of one or more anti-infectious agents.

16. A method of treatment of malaria in a patient, comprising the administration of a therapeutically effective amount of a compound according to claim 1, and optionally an effective amount of one or more anti-infectious agents.

17. A method of treatment of malaria in a patient, comprising the administration of a therapeutically effective amount of a compound according to claim 2, and optionally an effective amount of one or more anti-infectious agents.

18. A method of treatment of malaria in a patient, comprising the administration of a therapeutically effective amount of a compound according to claim 6, and optionally an effective amount of one or more anti-infectious agents.

19. A method for preparing a phosphonic acid compound according to claim 1, comprising the steps of:
(a) reacting an alpha-tributylstannyl propenyl phosphonate intermediate according to the following formula:

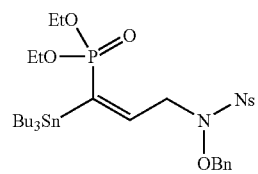

with an heteroaryl iodide to produce a 1-(R-substituted heteroaryl)-3-(N-benzyloxy-2-nitrobenzenesulfonamido)-prop-1-enylphosphonic acid dialkyl ester;
(b) converting the alkenyl moiety of the said 1-(R-substituted heteroaryl)-3-(N-benzyloxy-2-nitrobenzenesulfonamido)-prop-1-enylphosphonic acid dialkyl ester to produce the corresponding N-protected and O-protected propylphosphonic ester intermediate;
(c) removing the N-protecting group, e.g. the nitrobenzenesulfonamido group, of said N-protected and O-protected propylphosphonic ester intermediate followed by acylation thereof
(d) removing the O-protecting group of the acylated product from step (c); and
(e) hydrolysing the resulting phosphonic acid ester.

* * * * *

UNITED STATES PATENT AND TRADEMARK OFFICE
CERTIFICATE OF CORRECTION

| | |
|---|---|
| PATENT NO. | : 7,638,505 B2 |
| APPLICATION NO. | : 12/158973 |
| DATED | : December 29, 2009 |
| INVENTOR(S) | : Van Calenbergh et al. |

It is certified that error appears in the above-identified patent and that said Letters Patent is hereby corrected as shown below:

Column 5, Line 66, replace "pyridinyli" with --pyridinyl--.

Column 11, Line 10, replace "4-methoxy-cinnamaldehyde" with --4-methoxycinnamaldehyde--;

Line 11, replace "4-fluoro-cinnamaldehyde" with --4-fluorocinnamaldehyde--.

Column 23, Lines 51-52, replace "(1H, m, CH=CH$_2$, cis)" with --(1H, m, CH=CH$_{2,cis}$)--.

Column 25, Line 56, replace "134.24 (=Oq)" with --134.24 (=C)--.

Column 27, Lines 41-42, replace "(d, $^3J_{CP}$=6.9 Hz =COH)" with --(d, $^3J_{CP}$ = 6.9 Hz, =C$_o$H)--.

Column 32, Line 17, replace "3.8 HzandJ$_{HH}$" with --3.8 Hz and J$_{HH}$--;

Line 25, replace "=/-40 (d, $^1J_{CP}$==/-140 Hz, CHP)" with --+/- 40 (d, $^1J_{CP}$ = +/- 140 Hz, CHP)--.

Column 39, Lines 9-10, replace "(s, -CH$_2$)" with --(s, ß-CH$_2$)--;

Lines 27-28, replace "(s, -CH$_2$)" with --(s, ß-CH$_2$)--;

Lines 43-44, replace "(s, -CH$_2$)" with --(s, ß-CH$_2$)--.

Column 47, Line 42, replace "carbamoylhenyl" with --carbamoylphenyl--;

Signed and Sealed this
Seventh Day of February, 2012

David J. Kappos
*Director of the United States Patent and Trademark Office*

CERTIFICATE OF CORRECTION (continued)
U.S. Pat. No. 7,638,505 B2

Line 42, replace "PropenVlphosphonate" with --propenylphosphonate--.

Column 51, Lines 33-34, move "$^{31}$P NMR (121.50 MHz, CDCl$_3$)δ 27.1, 30.0 (minor/major)." to a new line.

Column 52, Line 2, replace "(113i)" with --(113j)--.

Column 53, Lines 17-18, replace "(=CH$^{13}$J$_{PC}$=3.3 Hz)" with --(=CH, $^3$J$_{PC}$ = 3.3 Hz)--.

Column 55, Lines 4-5, replace "sulfamovlphenyl" with --sulfamoylphenyl--;

Line 45, replace "(103i)" with --(103j)--.

Column 57, Line 25, replace "11.69" with --1.69--.

Column 60, Line 44, replace "thereof" with "thereof;".